US010919944B2

(12) United States Patent
Makepeace et al.

(10) Patent No.: US 10,919,944 B2
(45) Date of Patent: Feb. 16, 2021

(54) FILARIAL NEMATODE VACCINES, POLYPEPTIDES, AND NUCLEIC ACIDS

(71) Applicants: The University of Liverpool, Liverpool (GB); Edinburgh University, Edinburgh (GB)

(72) Inventors: Ben Makepeace, Liverpool (GB); David Taylor, Edinburgh (GB); Simon Babayan, Glasgow (GB); Stuart Armstrong, Liverpool (GB); Mark Blaxter, Edinburgh (GB)

(73) Assignees: The University of Liverpool, Liverpool (GB); Edinburgh University, Edinburgh (GB)

( * ) Notice: Subject to any disclaimer, the term of this patent is extended or adjusted under 35 U.S.C. 154(b) by 0 days.

(21) Appl. No.: 15/974,290

(22) Filed: May 8, 2018

(65) Prior Publication Data

US 2018/0355002 A1 Dec. 13, 2018

Related U.S. Application Data

(63) Continuation of application No. 15/118,043, filed as application No. PCT/GB2015/050380 on Feb. 11, 2015, now Pat. No. 9,994,624.

(30) Foreign Application Priority Data

Feb. 11, 2014 (GB) .................................. 1402352.7

(51) Int. Cl.
| | | |
|---|---|---|
| *A61K 39/00* | (2006.01) | |
| *C07H 21/02* | (2006.01) | |
| *C07H 21/04* | (2006.01) | |
| *C07K 14/435* | (2006.01) | |
| *A61K 45/06* | (2006.01) | |

(52) U.S. Cl.
CPC .......... *C07K 14/4354* (2013.01); *A61K 39/00* (2013.01); *A61K 39/0003* (2013.01); *A61K 45/06* (2013.01); *A61K 2039/552* (2013.01); *Y02A 50/30* (2018.01)

(58) Field of Classification Search
CPC ......... A61K 39/00; C07H 21/02; C07H 21/04
USPC ........................... 424/184.1, 265.1; 536/23.1
See application file for complete search history.

(56) References Cited

U.S. PATENT DOCUMENTS

| 6,265,198 B1 | 7/2001 | Tripp et al. |
| 8,962,259 B2 | 2/2015 | Noordin et al. |
| 2013/0236490 A1 | 9/2013 | Kalyanasundaram |

FOREIGN PATENT DOCUMENTS

| WO | WO 2010/068084 A1 | 6/2010 |
| WO | WO 2015/121646 A1 | 8/2015 |

OTHER PUBLICATIONS

Written Opinion of the International Searching Authority in PCT/GB2015/050380, dated Aug. 20, 2015, 10 pages.
International Search Report in PCT/GB2015/050380, dated Aug. 20, 2015, 6 pages.
James P. Hewitson et al., "Secretion of Protective Antigens by Tissue-Stage Nematode Larvae Revealed by Proteomic Analysis and Vaccination-Induced Sterile Immunity," dated Aug. 15, 2016, available at http://journals.plos.org/plospathogens/article?id=10.1371/journal.ppat.1003492, 15 pages.
Blaxter, M., "Caenorhabdities elegans is a nematode," Science, vol. 282, dated Dec. 11, 1998, http://www.cell.com/biophysj/fulltext/S0006-3495(13)05332-0, 1 page (abstract only).
Hai M. Nguyen et al., "Kv1.3-Blocking Peptides from Parasitic Worms Exhibit Immunomodulatory Function," Biophysical Journal, vol. 106, Issue 2, Supplement 1, dated Jan. 28, 2014, http://www.cell.com/biophysj/fulltext/S00006-3495(13)05332-0, 1 page.
Ghedin et al. "BMA-NAS-14, isoform b [Brugia malayi]," dated Sep. 21, 2007, http://www.ncbi.nlm.nih.gov/protein/cdp92843, 1 pages.
Nutman et al., "Hypothetical protein LOAG_17826," http://www.ncbi.nlm.nih.gov/protein/ejd74931.1, dated Apr. 11, 2012, 1 page.

*Primary Examiner* — Rodney P Swartz
(74) *Attorney, Agent, or Firm* — Faegre Drinker Biddle & Reath LLP

(57) ABSTRACT

The present invention relates to vaccines comprising a ShK domain of a filarial nematode protein. These vaccines may be used for the prevention and/or treatment of filarial nematode infections. The invention also relates to novel proteins comprising a ShK domain of a filarial nematode protein and pharmaceutical compositions. The invention may be used for the prevention and/or treatment of filarial nematode infections in canine subjects, and also in human subjects.

16 Claims, 19 Drawing Sheets

Specification includes a Sequence Listing.

MSRFILAIINARAKRPDNGISRSRDASSACYDKDPLCSSDICRNYPYTAKERCPKFCGLCSDTVS
GSSARPSSQFLPSSSQRQSLALTSGAVEKERKSLTSCTDKDSLCTAEICRNYPFTARERCAKTCGRCS
DEVAIGSGSTPAAHRSTAFGVEKFRGGSASSSLSPRIGNALISGSLCFDRKFDCSPEICPDFPFTARQ
ECAKTCGFCSVDTSISSSSSNATLRVMSPSVEIGGSSGGTSSHRTAKQDSYEAHHNIPAYPRLSRGEE
LECVDVNILCTQQTCKDYPFTAPEFCAKTCGFCPKGSVVEERHSSLPAAQGNKATAITKECKDEDSQC
SERSCLEHPYKASRKCAKTCGFCGEKSSYGSVIELESPIAASSDEGSVIALDSDGNDGSST■TMTSE
RPLTSGSGDTMSMQKPKHSSIFGFTDPIRSSSSASTAHIQQPTNKQYLGTQRYPGRTGPCTDANQLCF
KADCYKYPNFSQKYCERTCNYC

Fig. 9
(SEQ ID NO.1)

Figure 10:
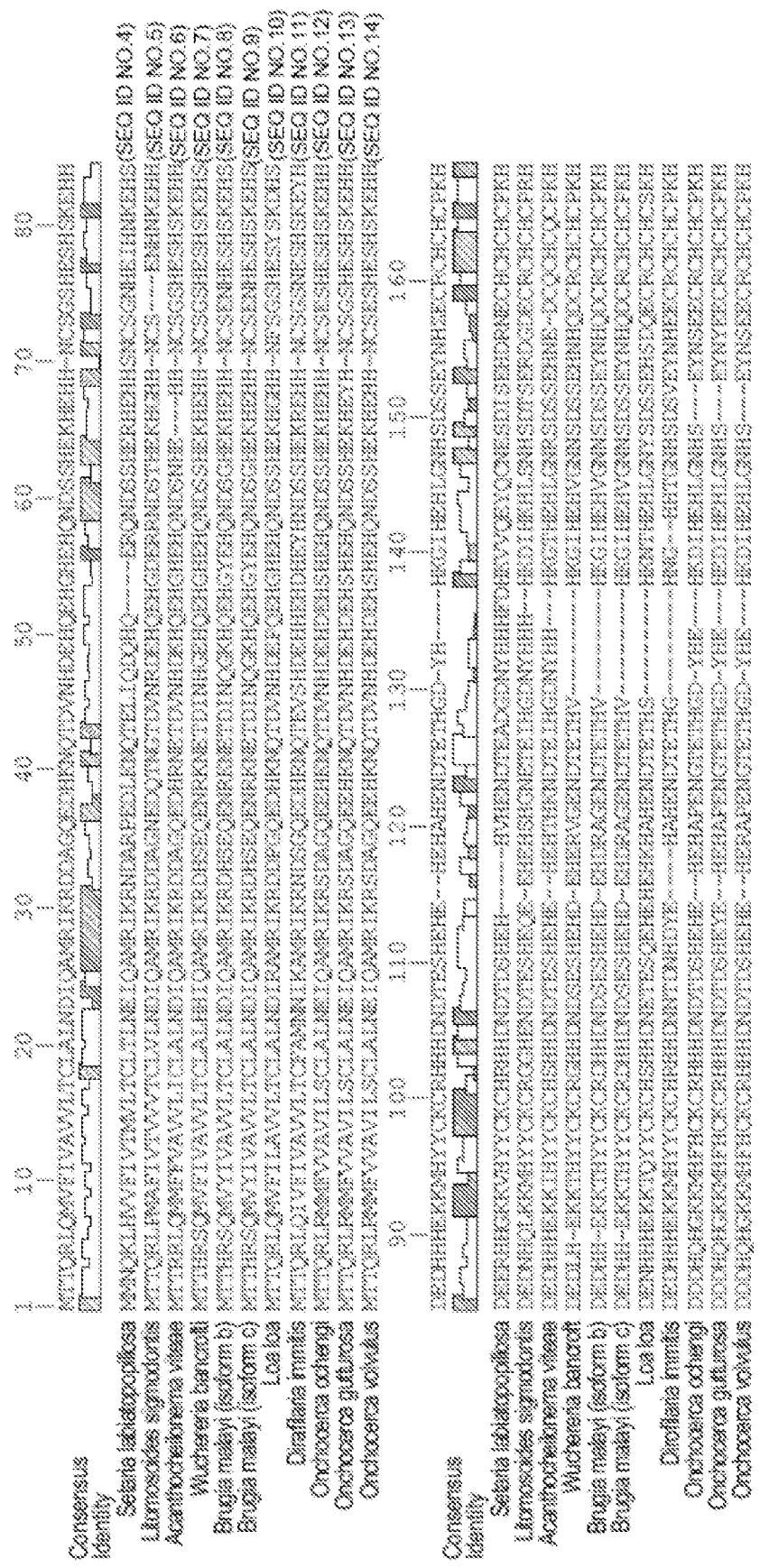

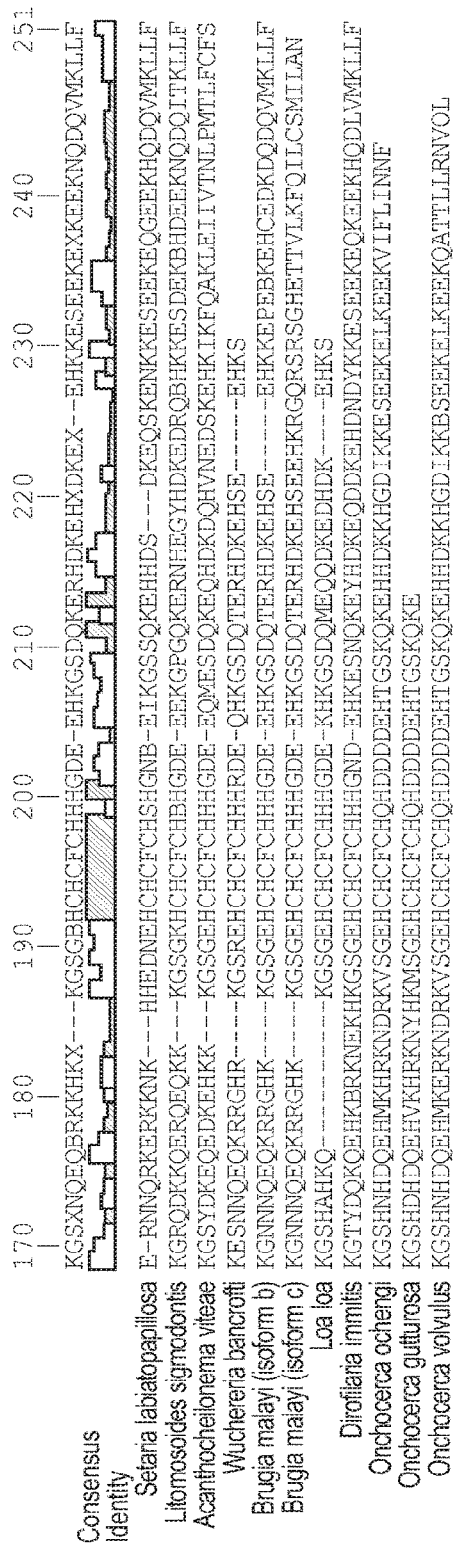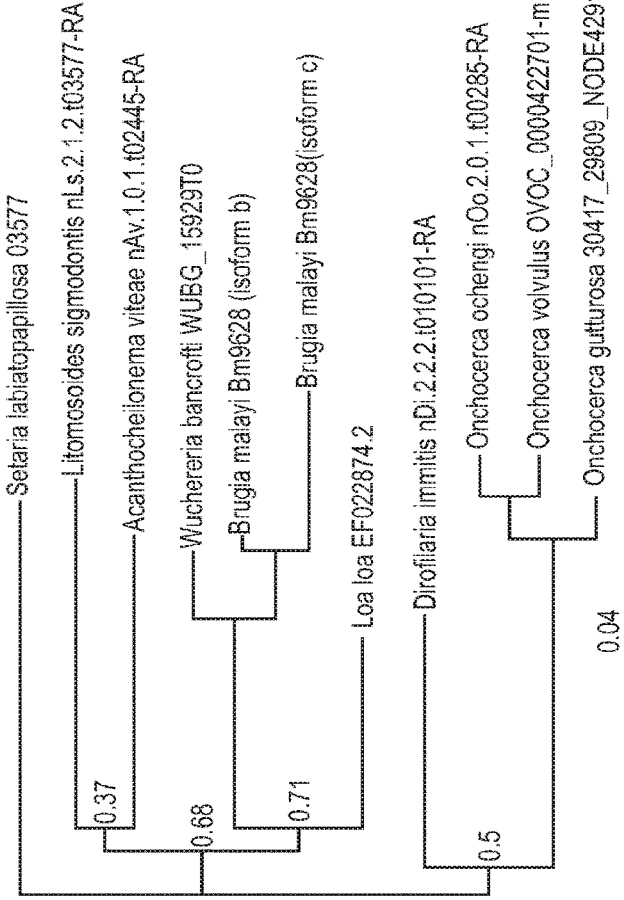
Fig. 10 continued
Fig. 11

FILARIAL NEMATODE VACCINES, POLYPEPTIDES, AND NUCLEIC ACIDS

PRIORITY CLAIM

This application is a continuation of U.S. application Ser. No. 15/118,043, now issued as U.S. Pat. No. 9,994,624, filed Aug. 10, 2016, which is a U.S. National Phase filing of PCT/GB2015/050380, filed Feb. 11, 2015, which claims the benefit of British Application No. GB 1402352.7, filed Feb. 11, 2014, the entire disclosures of all of which are hereby expressly incorporated by reference herein.

FIELD OF THE INVENTION

The present invention relates to vaccines for the prevention and/or treatment of filarial nematode infections, and to methods of prevention and/or treatment using such vaccines. The invention also relates to novel proteins, suitable for use in the prevention and/or treatment of filarial nematode infections. The invention further relates to pharmaceutical compositions comprising proteins of the invention, or nucleic acids encoding such proteins. The various aspects of the present invention are applicable to the prevention and/or treatment of filarial nematode infections in canine subjects, and also in human subjects.

BACKGROUND OF THE INVENTION

Nematodes are frequent infectious agents of both human and veterinary animal subjects. Filarial nematodes (belonging to the superfamily Filarioidea) are responsible for a global health burden of approximately 6.3 million disability-adjusted life-years, which represents the greatest single component of morbidity attributable to helminths affecting humans. No vaccine exists for the major filarial diseases, lymphatic filariasis and onchocerciasis; in part because research on protective immunity against filariae has been hampered by the inability of the human-parasitic species to complete their lifecycles in laboratory mice. However, the rodent filaria *Litomosoides sigmodontis* has become a popular experimental model over the past two decades, as BALB/c mice are fully permissive for its development and reproduction.

Lymphatic filariasis (LF) or "elephantiasis", which is distributed across Africa, South Asia, the Pacific, Latin America and the Caribbean, accounts for 92% of this toll; while the remainder is caused by onchocerciasis or "river blindness", primarily in sub-Saharan Africa. The major human filarial pathogens are *Wuchereria bancrofti* (which is responsible for 90% of LF cases), *Brugia malayi* and *Brugia timori* (geographically restricted causes of LF), and *Onchocerca volvulus* (the sole agent of human onchocerciasis). In addition, *Loa loa* affects ~13 million people in West and Central Africa, generally causing a relatively mild disease, although infection has been associated with severe and sometimes fatal adverse events following chemotherapy. Filarial parasites are primarily drivers of chronic morbidity, which manifests as disabling swelling of the legs, genitals and breasts in LF; or visual impairment and severe dermatitis in onchocerciasis. Furthermore, filarial parasites are also a major problem in small animal veterinary medicine, with ~0.5 million dogs in the USA alone infected with *Dirofilaria immitis*, the cause of potentially fatal heartworm disease.

Currently, control of human filarial diseases is almost entirely dependent on three anthelminthic drugs (ivermectin, diethylcarbamazine and albendazole), while prevention of heartworm also relies on prophylactic treatment of dogs and cats with ivermectin or other macrocyclic lactones. Reports of potential ivermectin resistance in *O. volvulus* and *D. immitis* have highlighted the importance of maintaining research efforts in vaccine development against filarial nematodes. However, rational vaccine design has been constrained for several decades by the intrinsic complexity of these metazoan parasites and their multistage lifecycle, which involves uptake of the first-stage larvae (microfilariae, Mf) by an haematophagous arthropod, two moults in the vector, transmission of third-stage larvae (L3) to a new vertebrate host, and two further moults before the worms mature as dioecious adults in a species-specific, parenteral predilection site. Moreover, the presence of obligate bacterial endosymbionts (*Wolbachia*) in many species of filarial nematodes adds another level of immunogenic stimuli to these pathogens, the impact of which remains incompletely defined. Following the publication of annotated genome sequences for *B. malayi*, *D. immitis* and *L. loa*, our understanding of the protein repertoire in filarial nematodes has been extended considerably by proteomic analyses of both whole body extracts (WBE) and excretory-secretory products (ESP), although only two studies (both of *B. malayi*) have examined stage-specific filarial secretomes to date. In the context of vaccine design, the identification of ESP proteins and determination of their expression in each major lifecycle stage can facilitate the prioritisation of candidates for efficacy screening in animal models.

One of the most popular rodent models for filarial research, which was first used during the 1940s in its natural host (the cotton rat, *Sigmodon hispidus*), is *Litomosoides sigmodontis* which was previously designated as *L. carinii*, though this nomenclature is taxonomically incorrect. The utility of this model for both basic immunological studies and vaccine screening changed radically with the discovery that unlike *B. malayi* and indeed all other filarial species, *L. sigmodontis* can complete its lifecycle in immunocompetent laboratory mice. Consequently, over the past two decades this model has drawn on the full power of murine immunology, including defined knockout strains, to address questions regarding the fundamental immunomodulatory mechanisms employed by filarial parasites, their susceptibility to different modes of vaccination, and most recently, their ability to mitigate proinflammatory pathology and autoimmune disease. In particular, the *L. sigmodontis* model has been central in defining the role of T-regulatory cells in filarial immune evasion, and has enabled the assessment of the impact of various vaccine strategies not only on adult worm burden, but on fecundity as determined by the density of Mf circulating in the bloodstream.

SUMMARY OF THE INVENTION

In a first aspect, the invention provides a polypeptide comprising a ShK domain of a filarial nematode protein, or a variant thereof, for use as a vaccine for the prevention and/or treatment of a filarial nematode infection.

In a second aspect, the invention provides an artificial polypeptide comprising a plurality of ShK domains of a filarial nematode protein, or variants of such domains, and an artificial spacer separating the ShK domains or variants.

In a third aspect, the invention provides a nucleic acid encoding a polypeptide according to the second aspect of the invention.

In a fourth aspect, the invention provides a nucleic acid encoding a polypeptide comprising a ShK domain of a filarial nematode protein, or a variant thereof, for use as a vaccine for the prevention and/or treatment of a filarial nematode infection.

In a fifth aspect, the invention provides a pharmaceutical composition comprising a polypeptide that comprises a ShK domain of a filarial nematode protein, or a variant thereof.

In a sixth aspect, the invention provides pharmaceutical composition comprising a nucleic acid encoding a polypeptide that comprises a ShK domain of a filarial nematode protein, or a variant thereof.

In a seventh aspect, the invention provides a method of preventing and/or treating a filarial nematode infection, the method comprising providing to a subject in need of such prevention and/or treatment a therapeutically effective amount of a polypeptide comprising a ShK domain of a filarial nematode protein, or a variant thereof.

These various aspects of the present invention arise from the inventors' finding that polypeptides containing ShK domains from filarial nematodes, or nucleic acids encoding such polypeptides, are able to confer protective immunity in respect of filarial nematodes associated with the development of diseases.

As discussed below, the various aspects of the invention have utility in the prevention and/or treatment of filarial nematode infections in human subjects, or in veterinary subjects such as dogs.

DETAILED DESCRIPTION OF THE INVENTION

Definitions

For the avoidance of doubt, definitions will now be provided in respect of certain terms used in the description of the present invention.

"ShK Domain of a Filarial Nematode Protein"

Filarial nematodes (those that belong to the superfamily Filarioidea) are those most commonly responsible for diseases in humans, and to a lesser extent, other animal hosts. A good deal of information is available regarding the proteome of filarial nematodes.

ShK domains, which are so called due to their similarity to the *Stichodactyla* toxin produced by the sea anemone *Stichodactyla helianthus*, contain six cysteine residues with a characteristic spacing. ShK domains present in an amino acid sequence are readily identified using a bioinformatics approach. For example, they are defined in the Pfam database by the identifier "PF01549" and in the InterPro database by the identifier "IPR003582".

The inventors have found that proteins from filarial nematode species that vary quite significantly in terms of their sequence across the protein as a whole share notably higher levels of similarity in their ShK domains. This opens the possibility of using polypeptides comprising ShK domains (or variants thereof) derived from a first filarial nematode pathogen in the prevention and/or treatment of diseases caused by infection with a second, different, filarial nematode pathogen.

ShK domains in filarial nematode proteins are illustrated in the sequence information and comparison section of this specification. Here the characteristic arrangement of six cysteines within the ShK domains can be seen, as can the increased degree of sequence identity within ShK domains of different nematodes (as compared to sequence identity shared by the proteins as a whole).

As discussed elsewhere in the specification, the *L. sigmodontis* ShK domain protein nLs_04059 represents an example of a filarial nematode protein; a ShK domain of which may be employed in the various aspects of the invention. ShK domains from this protein or orthologues of this protein, or variants thereof, may be employed in the various aspects of the invention.

nLs_04059 orthologues including suitable ShK domains, or variants thereof, are shown in FIG. 12. These include proteins derived from filarial nematodes such as: *L. sigmodontis* (for example isoform nLS.2.1.2.t04059 (Gene ID nLs.2.1.2.g04059 Species *Litomosoides sigmodontis* (PRJEB3075) Location nLs.2.1.scaf00244:12218-16228), *B. malayi* (for example isoforms Bm8157b (Gene ID WBGene00228418, Species *Brugia malayi* (PRJNA10729), Location Bmal_v3_scaffold110:112156-116304), Bm8157d (Gene ID WBGene00228418 Species *Brugia malayi* (PRJNA10729) Location Bmal_v3_scaffold110:112156-116304), Bm8157c (Gene ID WBGene00228418, Species *Brugia malayi* (PRJNA10729) Location Bmal_v3_scaffold110:112156-116304) and Bm12896a), *A. viteae* (for example isoform nAV.1.0.1.t09742, (Gene ID nAv.1.0.1.g09742, Species *Acanthocheilonema viteae* (PRJEB4306) Location nAv.1.0.scaf00135:58565-62790), *D. immitis* (for example isoforms nDi.2.2.2.t03402 (Gene ID nDi.2.2.2.g03402 Species *Dirofilaria immitis* (PRJEB1797) Location nDi.2.2.scaf00051:142071-145588), and nDi.2.2.2.t04314 (Gene ID nDi.2.2.2.g04314, Species *Dirofilaria immitis* (PRJEB1797) Location nDi.2.2.scaf00083:48251-52806), *L. loa* (for example isoforms EJD74930.1 (Gene ID LOAG_17825, Species *Loa loa* (PRJNA60051) Location JH712199:22673-23334), and EJD74931.1 (Gene ID LOAG_17826, Species *Loa loa* (PRJNA60051) Location JH712199:24313-26569), *O. ochengi* (for example isoforms nOo.2.0.1.t12220 (Gene ID nOo.2.0.1.g12220 Species *Onchocerca ochengi* (PRJEB1809) Location nOo.2.0.Scaf09993:244-1668), nOo.2.0.1.t06172 (Gene ID nOo.2.0.1.g06172, Species *Onchocerca ochengi* (PRJEB1809) Location nOo. 2.0. Scaf01844:10830-11939), and nOo.2.0.1.t06343 (Gene ID nOo.2.0.1.g06343, Species *Onchocerca ochengi* (PRJEB1809) Location nOo.2.0.Scaf01943:3177-7069). *O. volvulus* (for example isoforms OVOC 0000232701.1, and OVOC 000102301.1) and *W. bancrofti* (for example isoforms WUBG 17834T0, and WUBG05152T0).

All Gene ID sequences identified in the preceding paragraph are from WormBase ParaSite database version 1 (September 2014).

For the sake of brevity, the specification will use the terms "ShK domain of a filarial nematode protein" and "Shk domain" interchangeably.

"Variants" of Domains

For the purposes of the present disclosure, a variant of a ShK domain of a filarial nematode protein should be considered to encompass sequences sharing at least 70% identity with a ShK domain of a filarial nematode protein. Optionally, variants may share at least 75% identity, at least 80% identity, at least 85% identity, or at least 90% identity with a ShK protein. In suitable embodiments, variants may share at least 91% identity, at least 92% identity, at least 93% identity, at least 94% identity, at least 95% identity, at least 96% identity, at least 97% identity, at least 98% identity, at least 99% identity with a Shk domain of a filarial nematode protein.

It should be borne in mind that the overall level of identity between *L. sigmodontis* ShK domain protein nLs_04059 (SEQ ID NO: 1) and its orthologues in filarial pathogens ranges from 31% (in *W. bancrofti*) to 51% (in *O. volvulus*).

However, the level of identity between individual ShK domains between species always exceeds 70% and preferably exceeds 85%.

It will be appreciated that, in order to function as a useful vaccine, a polypeptide of the invention should exhibit the ability to induce a protective immune response. Suitably a variant may retain at least 70% of the immunogenic capacity of the ShK domain from which it is derived. Indeed, a variant may retain at least 80%, at least 90%, or even at least 95% of the immunogenic capacity of the ShK domain from which it is derived. Suitably a variant may have a greater immunogenic capacity than the ShK domain from which it is derived.

"Prevention and/or Treatment"

The medical uses, methods of treatment, and pharmaceutical compositions of the invention may be used to establish protective immunity that prevents the establishment of a filarial nematode infection in a subject. This prophylactic use exemplifies the "prevention" of a filarial nematode infection as this term is used in the present disclosure.

The advantages of these various aspects of the invention may also be applicable to subjects that have previously undergone infection with a filarial nematode parasite. For the purposes of the present disclosure, such applications of the invention, in which a disease associated with an existing infection is alleviated, may be considered to represent "treatment" of the filarial nematode infection.

Prevention and/or treatment of a filarial nematode infection brings about a corresponding prevention and/or treatment of the disease associated with the filarial nematode infection.

"Polypeptides of the Invention"

In the context of the present disclosure, references to "a polypeptide of the invention" or to "polypeptides of the invention" should be taken as encompassing not only the artificial polypeptides of the second aspect of the invention, but also the polypeptides for medical use (as vaccines for the prevention and/or treatment of a filarial nematode infection) defined by the first aspect of the invention.

As discussed further below, the medical uses of the first aspect of the invention may employ naturally occurring polypeptides, or may make use of artificial polypeptides such as those of the second aspect of the invention.

For the sake of brevity, the majority of the following embodiments of the invention will be discussed primarily in the context of polypeptides of the invention, whether the polypeptides for medical use of the first aspect of the invention, or the artificial polypeptides of the second aspect of the invention. However, it should be appreciated that the considerations set out herein in respect of polypeptides of the invention will also, except for where the context requires otherwise, be applicable to the other aspects of the invention, such as nucleic acids (where the considerations may be applicable to the polypeptides encoded by such nucleic acids sequences), pharmaceutical compositions, and methods of treatment.

As referred to above, the polypeptide or nucleic acids of the invention are suitable for use as vaccines, where the vaccine is for the prevention and/or treatment of a filarial nematode infection.

In a suitable embodiment, a polypeptide of the invention may comprise an ShK domain from *L. sigmodontis*. As the results set out herein illustrate, the inventors have believe that polypeptides comprising ShK domains from *L. sigmodontis* (and specifically nucleic acids encoding such polypeptides) are surprisingly able to act as vaccines conferring protective immunity in respect of infections by filarial nematodes other than *L. sigmodontis*.

Without detracting from the above, in a suitable embodiment a polypeptide in accordance with the invention comprises an ShK domain from a filarial nematode infection which is to be prevented and/or treated (or a variant of such an ShK domain).

Suitably, a polypeptide for of the invention may be for use in the prevention and/or treatment of canine heartworm. In such an embodiment, the polypeptide may comprise a ShK domain from *D. immitis*, or a variant thereof.

A polypeptide of the invention may be for use in the prevention and/or treatment of a disease in a human subject, the disease being selected from the group consisting of: lymphatic filariasis (also referred to as "elephantiasis"); onchocerciasis (also referred to as "river blindness"); and loiasis.

Suitably a polypeptide of the invention for use in the prevention and/or treatment of lymphatic filariasis will comprise a ShK domain from a filarial nematode selected from the group consisting of: *Wuchereria bancrofti*; *Brugia malayi*; and *Brugia timori*, or a variant thereof. Of these three filarial nematodes, *W. bancrofti* is responsible for approximately 90% of lymphatic filariasis cases, and so polypeptides comprising an ShK domain from *W. bancrofti* may be preferred for use in the prevention and/or treatment of lymphatic filariasis.

In an embodiment in which a polypeptide of the invention is for use in the prevention and/or treatment of onchocerciasis, it may comprise a ShK domain from *Onchocerca volvulus*, or a variant thereof.

A suitable polypeptide for use in the prevention and/or treatment of loiasis, may comprise a ShK domain from *Loa loa*, or a variant thereof.

In a suitable embodiment, a polypeptide of the invention comprises a plurality of ShK domains, or variants thereof. Thus, by way of non-limiting example, a polypeptide of the invention may comprise at least two, at least three, at least four, at least five, or at least six ShK domains or variants thereof. In suitable embodiments, a polypeptide of the invention may comprise two, three, four, five or six ShK domains or variants thereof.

In the event that a polypeptide according to the invention comprises a plurality of ShK domains (or variants thereof), it may comprise a plurality of the same ShK domain (or variants of the same ShK domain). In an embodiment utilising variants of the same ShK domain these variant may be the same variant, or may comprise a plurality of different variants.

Alternatively, a polypeptide of the invention comprising a plurality of ShK domains (or variants thereof), it may comprise a plurality of the different ShK domains (or variants of these different domains). Suitably each one of the plurality of ShK domains may be different, or alternatively the polypeptide may comprise more than one copy of a single ShK domain among a plurality of different domains.

Merely by way of example, in the case of *D. immitis* the naturally occurring ShK domain protein contains six ShK domains, each of which has its own characteristic sequence. A polypeptide of the invention may comprise each of these six ShK domains. Alternatively, a polypeptide of the invention may comprise six ShK domains made up of six copies of the same ShK sequence, such as the sixth of the sequences found in the native protein.

The sixth ShK sequence found in the native ShK domain protein of *D. immitis* may represent a preferred ShK domain to be included (either directly, or in variant form) in a polypeptide of the invention. Thus, in a suitable embodiment a polypeptide of the invention may comprise one or more ShK domains (or variants thereof) selected from ShK domains one to five of the native protein, in addition to the sixth ShK domain (or a variant thereof).

In the event that a polypeptide of the invention comprises only a single ShK domain derived from *D. immitis*, the single ShK domain may be the sixth ShK domain from the ShK domain protein of *D. immitis* (or a variant based upon this domain).

It will be appreciated that the considerations set out in the preceding paragraphs also apply to polypeptides of the invention comprising variants of the ShK domains found in *D. immitis*.

A polypeptide of the invention may be a branched protein. In a suitable embodiment, each branch of the protein may carry an antigenic sequence. Some, and potentially all, of these antigenic sequences may comprise ShK domains, or their variants.

In a suitable embodiment, a polypeptide of the invention may further comprise an additional antigen that is able to confer protective immunity on a subject to whom the additional antigen is provided. Suitably such a polypeptide may comprise an additional antigen that does not comprise an ShK domain.

In a suitable embodiment, the additional antigen incorporated in such a polypeptide may be a further nematode antigen. Suitably the additional antigen capable of conferring protective immunity is derived from the same filarial nematode as the ShK domain incorporated in the polypeptide.

Some of the embodiments referred to above may be provided by naturally occurring polypeptides comprising an ShK domain. In a suitable embodiment a polypeptide to be employed in accordance with the various aspects or embodiments of the invention may be a naturally occurring polypeptide.

Certain of the embodiments referred to above may only be provided by artificial polypeptides comprising an ShK domain. As set out above, the second aspect of the invention provides an artificial polypeptide comprising a plurality of ShK domains of a filarial nematode protein, or variants thereof, and an artificial spacer separating the ShK domains or variants.

A suitable artificial spacer serves to expose the ShK domains to cells of the immune system, thereby allowing the development of protective immunity. The spacer itself need not contribute to the development of the protective immunity and may itself be immunologically inert.

The artificial spacer may be any spacer, other than naturally occurring sequence found between ShK domains in a natural protein, that serves to separate the ShK domains, or variants, within the artificial protein. In a suitable embodiment an artificial spacer suitable for use in the artificial polypeptides of the invention may comprise a sequence of amino acid residues that separates the ShK domains or variant. In a suitable embodiment the spacer may comprise poly-L-lysine.

Artificial polypeptides of the invention may comprise a plurality of artificial spacers, as necessitated by the number of ShK domains (or variants thereof) incorporated in the artificial polypeptide.

In a suitable embodiment a polypeptide to be employed in accordance with the various aspects or embodiments of the invention may be an artificial polypeptide, such as an artificial polypeptide of the $2^{nd}$ aspect of the invention.

Suitably an artificial polypeptide of the invention may be a chimeric polypeptide. Artificial polypeptides of the invention may comprise a ShK domain, or variant thereof, and an additional antigen that is not found in the polypeptide from which the ShK domain is derived. Merely by way of example, an artificial protein of the invention may comprise an ShK domain (or variant thereof) and an additional antigen from a nematode that the ShK domain is derived from, or an additional antigen from a nematode other than that which the ShK is derived from, or an additional antigen that is derived from a source other than a nematode. Chimeric polypeptides of the invention comprising an ShK domain or variant thereof, and an additional antigen from a source other than the filarial nematode from which the ShK domain was derived are able to induce protective immunity against more than one pathogen.

Artificial polypeptides of the invention may comprise a plurality of the same ShK domain, or variants thereof. Alternatively, artificial polypeptides of the invention may comprise a plurality of different ShK domains, or variants thereof.

In a suitable embodiment an artificial polypeptide of the invention further comprises an additional vaccine antigen. Suitably the additional vaccine antigen may be derived from an antigen that does not comprise a ShK domain.

An artificial polypeptide of the invention may comprise an additional vaccine antigen derived from the same filarial nematode (or filarial nematodes) as the ShK domains incorporated in the polypeptide.

Examples of suitable additional vaccine antigens that may be incorporated in artificial polypeptides of the invention include cysteine proteinase inhibitor (CPI) and/or abundant larval transcript (ALT). As discussed elsewhere in the specification, these proteins represent secreted immunomodulators secreted by female filarial nematodes, and targeting of these immunomodulators by vaccination leads to greatly reduced microfilaremial. Accordingly, introduction of these additional vaccine antigens into artificial polypeptides of the invention will be expected to confer therapeutic advantages that go beyond the surprising benefits provided by the polypeptides of the invention. Therapeutic vaccination of *Onchocerca volvulus*-infected hosts with vaccines comprising CPI and/or ALT in combination with the ShK domain-containing polypeptides of the invention may provide further suppression of microfilarial production, prevent the progression of disease, reduce morbidity and block transmission, even if adult worm burden remains unaffected.

Furthermore, it will be appreciated that in a suitable embodiment a polypeptide, medical use, or method of treatment of the invention utilising as a vaccine a polypeptide comprising a ShK domain of a filarial nematode protein, or a variant thereof, may be used in conjunction with a vaccine comprising CPI and/or ALT. Suitably the polypeptide of the invention may be provided in the same vaccine as the CPI and/or ALT. Alternatively the polypeptide of the invention and the CPI and/or ALT may be provided in separate vaccines.

The invention provides a nucleic acid encoding a polypeptide of the invention. The nucleic acid may encode an artificial polypeptide in accordance with the second aspect of the invention.

The invention also provides a vector comprising a nucleic acid of the invention, and such a vector may be adapted for expression in bacteria, such as *E. coli*.

Pharmaceutical compositions of the invention may comprise a polypeptide of the invention and/or a nucleic acid of the invention. The nucleic acid may be provided in the form of a vector.

Suitable pharmaceutical compositions of the invention may be formulated for use as a vaccine, and may be formulated for any appropriate route of administration, including (but not limited to) injection.

That said, suitable routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Pharmaceutical compositions in accordance with the invention may be formulated such that the polypeptide or nucleic acid of the invention is delivered in alum adjuvant, or in virus-like particles.

Figure 1A:
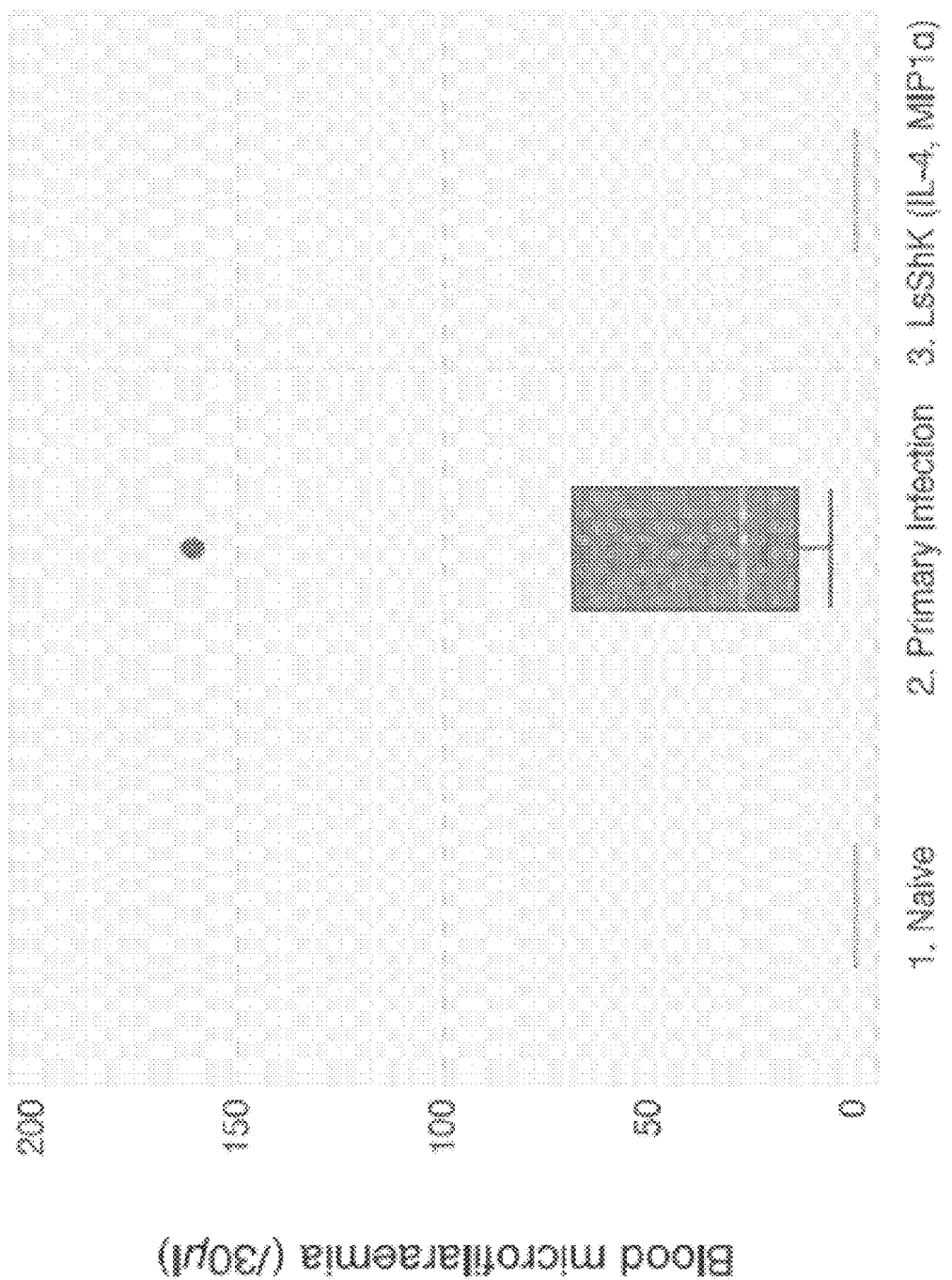
Figure 1B:
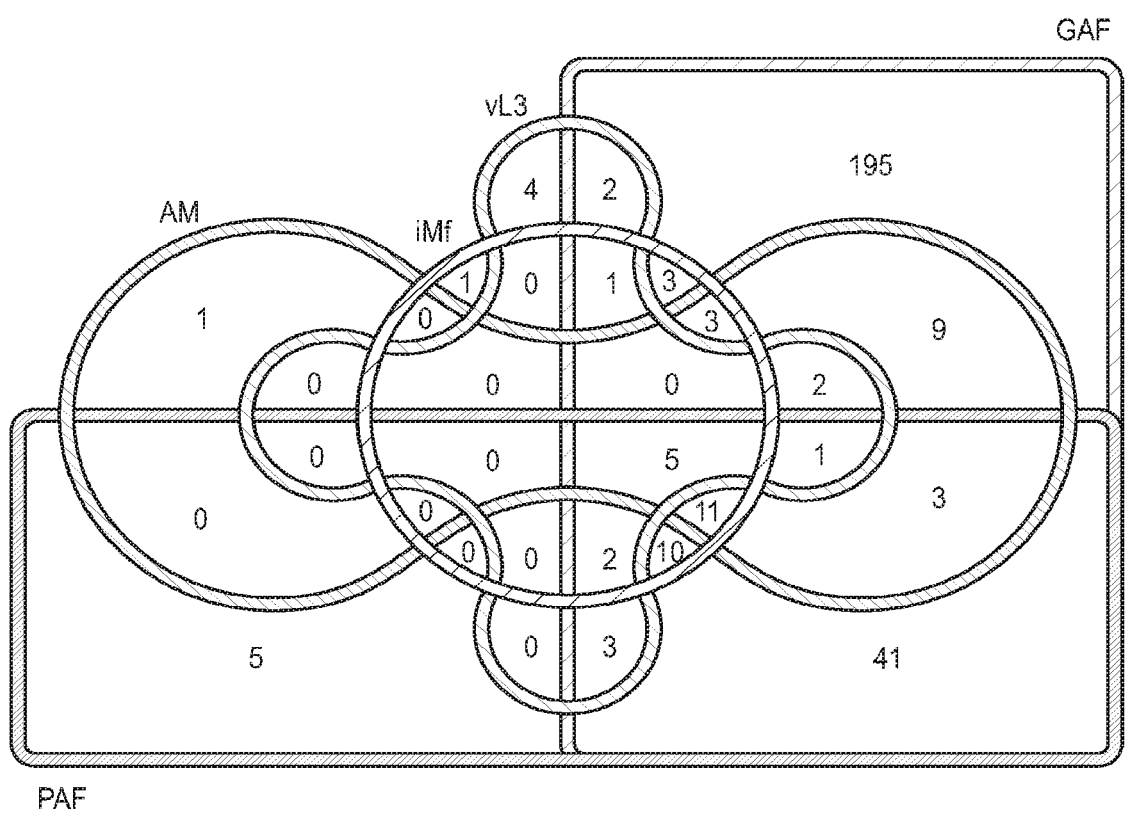

As referred to above, the seventh aspect of the invention provides a method of preventing and/or treating a filarial nematode infection, the method comprising providing to a subject in need of such prevention and/or treatment a therapeutically effective amount of a polypeptide comprising a ShK domain of a filarial nematode protein, or a variant thereof. For brevity, such methods may be referred to in the present disclosure as "methods of treatment", but, unless the context requires otherwise, it should be considered that such methods of treatment also encompass prophylactic use to prevent filarial nematode infections.

It will be appreciated that the various polypeptides of the invention described herein represent suitable polypeptide to be used in such methods of treatment, and the various considerations set out in connection with the nature of such polypeptides will also be applicable to polypeptides for use in such methods of treatment.

The methods of treatment of the invention are applicable to veterinary subjects. In a suitable embodiment of a method of the invention the subject is a dog, and the filarial nematode infection to be prevented and/or treated is heartworm. In a method in which it is desired to prevent and/or treat heartworm, the polypeptide provided in the method suitably comprises a ShK domain from *D. immitis*, or a variant thereof.

The methods of treatment of the invention are also applicable to human subjects. Suitably, when the subject is a human, the filarial nematode infection to be prevented and/or treated is one that causes a disease selected from the group consisting of: lymphatic filariasis; onchocerciasis; and loiasis.

In an embodiment of the invention in which the disease to be prevented and/or treated is lymphatic filariasis, the polypeptide suitably comprises a ShK domain from *Wuchereria bancrofti; Brugia malayi*; and *Brugia timori*, or a variant thereof.

*W. bancrofti* is responsible for approximately 90% of lymphatic filariasis cases, and so it may be preferred that methods for the prevention and/or treatment of lymphatic filariasis make use of polypeptides comprising an ShK domain from *W. bancrofti.*

Suitably a method of the invention in which it is wished to prevent and/or treat onchocerciasis may make use of a polypeptide comprising a ShK domain from *Onchocerca volvulus*, or a variant thereof.

Methods of the invention in which it is desired to prevent and/or treat loiasis may make use of a polypeptide that comprises a ShK domain from *Loa loa*, or a variant of such a domain.

The skilled reader will appreciate that in suitable embodiments of methods of treatment in accordance with the invention, the therapeutically effective amount of the polypeptide is provided by administration of the polypeptide. The therapeutically effective amount may be provided through single or multiple incidences of administration, as required. Suitably such embodiments of the invention may utilise pharmaceutical compositions of the invention for the provision of the required amount of the polypeptide.

The invention also encompasses methods of treatment in which the therapeutically effective amount of the polypeptide is provided by administration of a nucleic acid encoding the polypeptide, for example by provision of the nucleic acid in a suitable vector. In such embodiments expression of the nucleic acid by the cells of the recipient subject leads to the production of the therapeutically effective amount of the protein, thus leading to the development of protective immunity. These embodiments of the methods of treatment may utilise pharmaceutical compositions comprising nucleic acids, which are also aspects of the present invention.

Factors that may be considered in the determination of a therapeutically effective amount of a polypeptide, variant, or nucleic acid of the invention may include: the nature of the agent in question (i.e. whether the agent in question is a polypeptide, a variant thereof, or a nucleic acid); the activity of the agent in question; the severity of the infection to be prevented and/or treated; the size of the subject requiring prevention and/or treatment; and the route by which the agent is to be administered.

Merely by way of example, a therapeutically effective amount of a polypeptide comprising a ShK domain, or a variant thereof, or a nucleic acid encoding such a polypeptide or variant, may be between 1.5 g and 1 μg. A suitable therapeutically effective amount may be between 1500 mg and 1 mg; for example between 1000 mg and 50 mg; such as between 500 mg and 100 mg. Alternatively a suitable therapeutically effective amount may be between 100 mg and 1 mg; for example between 50 mg and 5 mg; such as between 25 mg and 10 mg. In a further suitable embodiment, a suitable therapeutically effective amount may be between 500 μg and 1 μg; for example between 400 μg and 5 μg; such as between 250 μg and 10 μg. Merely by way of example, a suitable therapeutically effective amount may be between 200 μg and 15 μg, such as between 150 μg and 20 μg, between 100 μg and 25 μg, or between 50 μg and 30 μg. Suitably a therapeutically effective amount may be approximately 40 μg.

Within a course of treatment to prevent and/or treat a filarial nematode infection a polypeptide comprising a ShK domain, or a variant thereof, or a nucleic acid encoding such a polypeptide or variant, may be provided in one or more administrations. Incidences of administration may be provided once per 24 hours, once a week, once, a month, or as otherwise required.

The invention will now be further described with reference to the following Experimental Results and Figures in which:

FIG. 1A. Graph illustrating the difference in parasite burden between vaccinated and non-vaccinated mice in Study 1 below;

FIG. 1B. Distribution of ESP proteins between life stages of *L. sigmodontis*. Venn diagram of the shared and stage-specific ESP proteins in each of the life stages examined.

Figure 2:
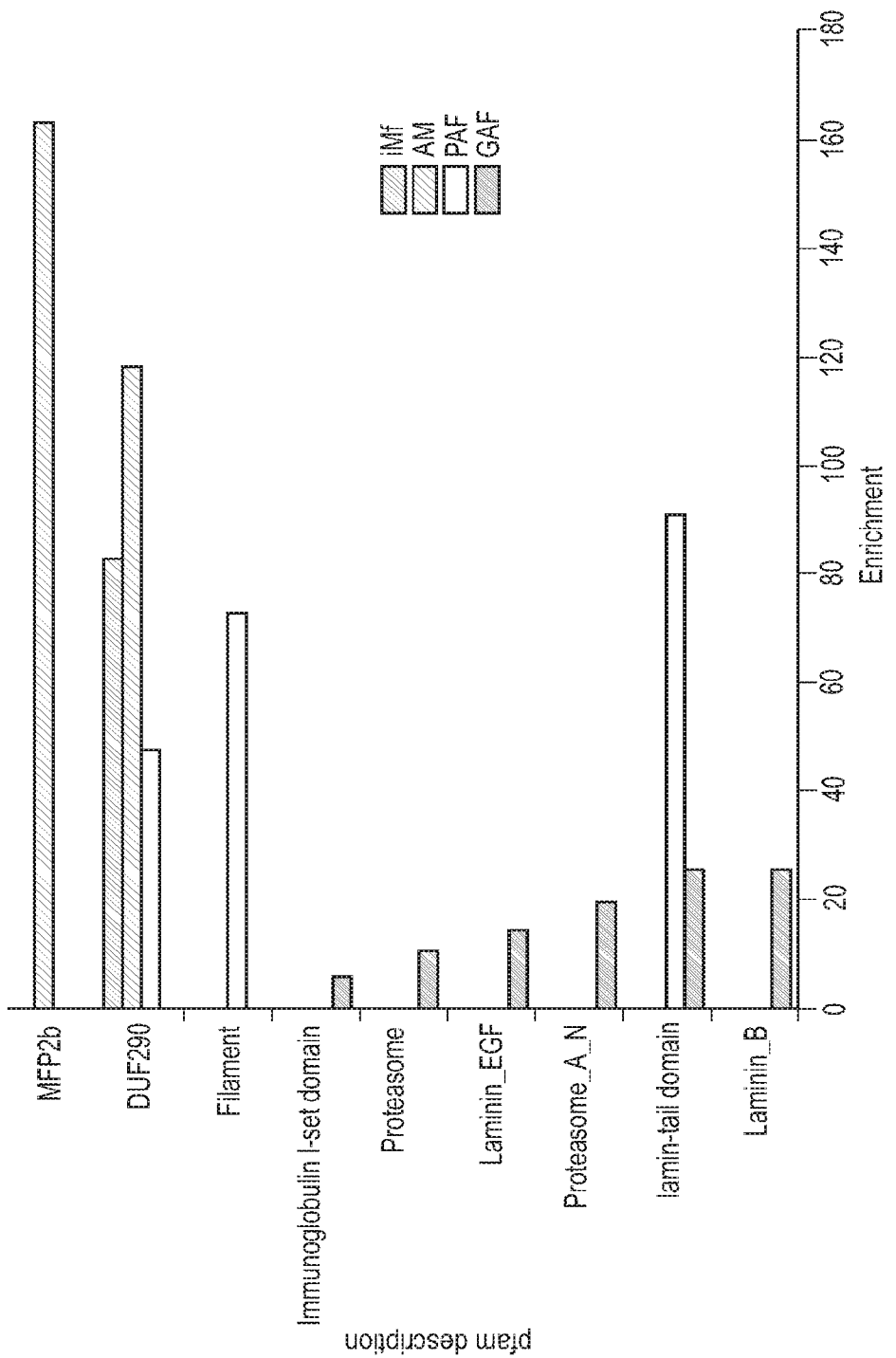

FIG. 2. Pfam enrichment analysis of ESP proteins against the complete theoretical proteome of *L. sigmodontis*. The fold-enrichment is displayed for each lifecycle stage; DUF290 represents the transthyretin-like protein family.

Figure 3:
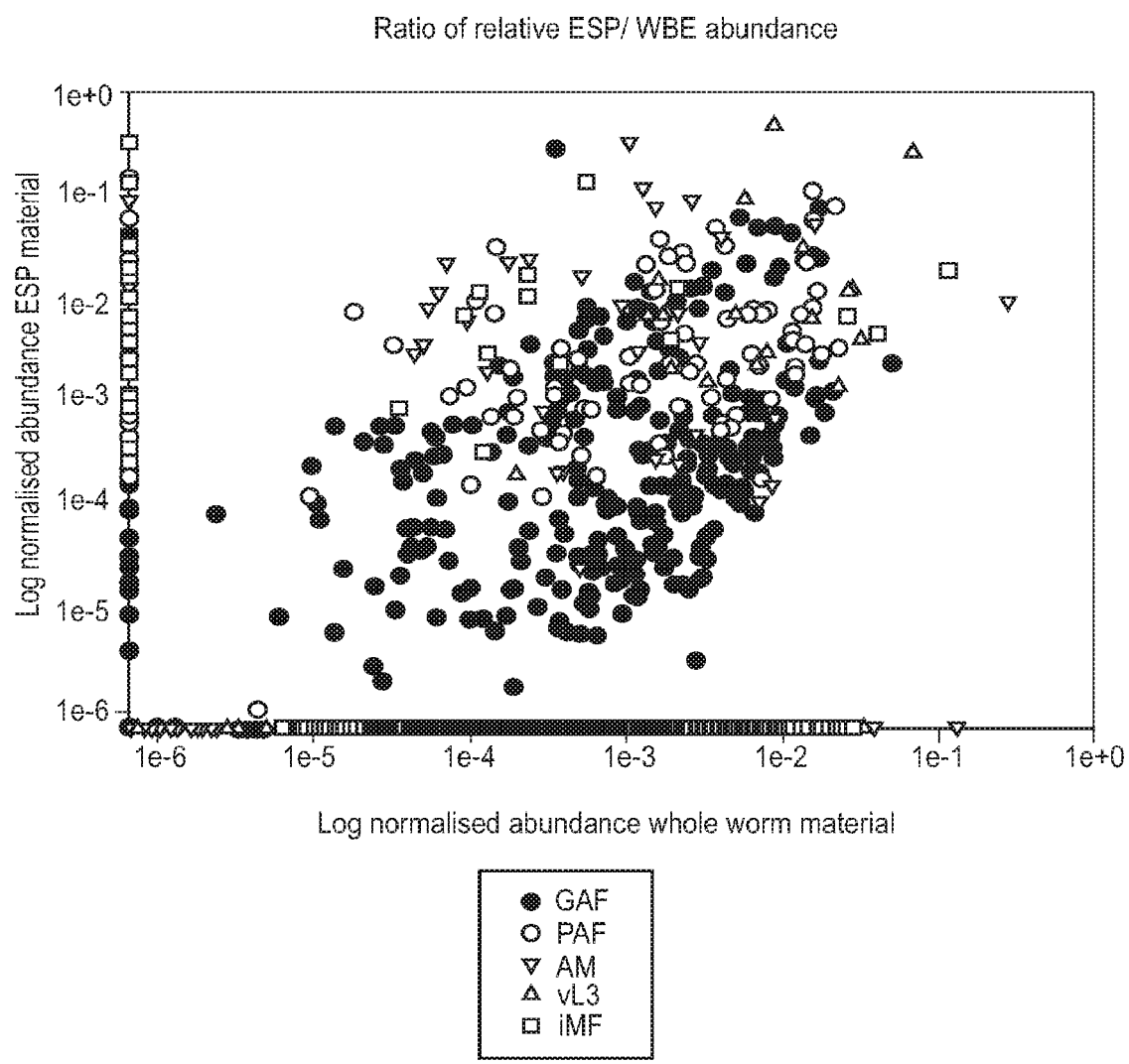

FIG. 3. Relative abundance of *L. sigmodontis* ESP proteins compared to corresponding somatic extracts. ESP proteins (≥2 peptides detected at p<0.05 and <1% FDR, present in ≥2 biological replicates) were quantified by ion intensity (iBAQ) and compared to the iBAQ abundance of the same protein present in somatic extracts of intact nematodes (x-axis). Individual abundance values were normalised by dividing by the summed total abundance of that individual sample (life stage). The normalised abundance ratio was used as a guide to evaluate the enrichment of the protein (ESP/WBE). Note that as the data are normalised within each life stage dataset, comparing protein abundance directly between life stages is not valid.

Figure 4A:
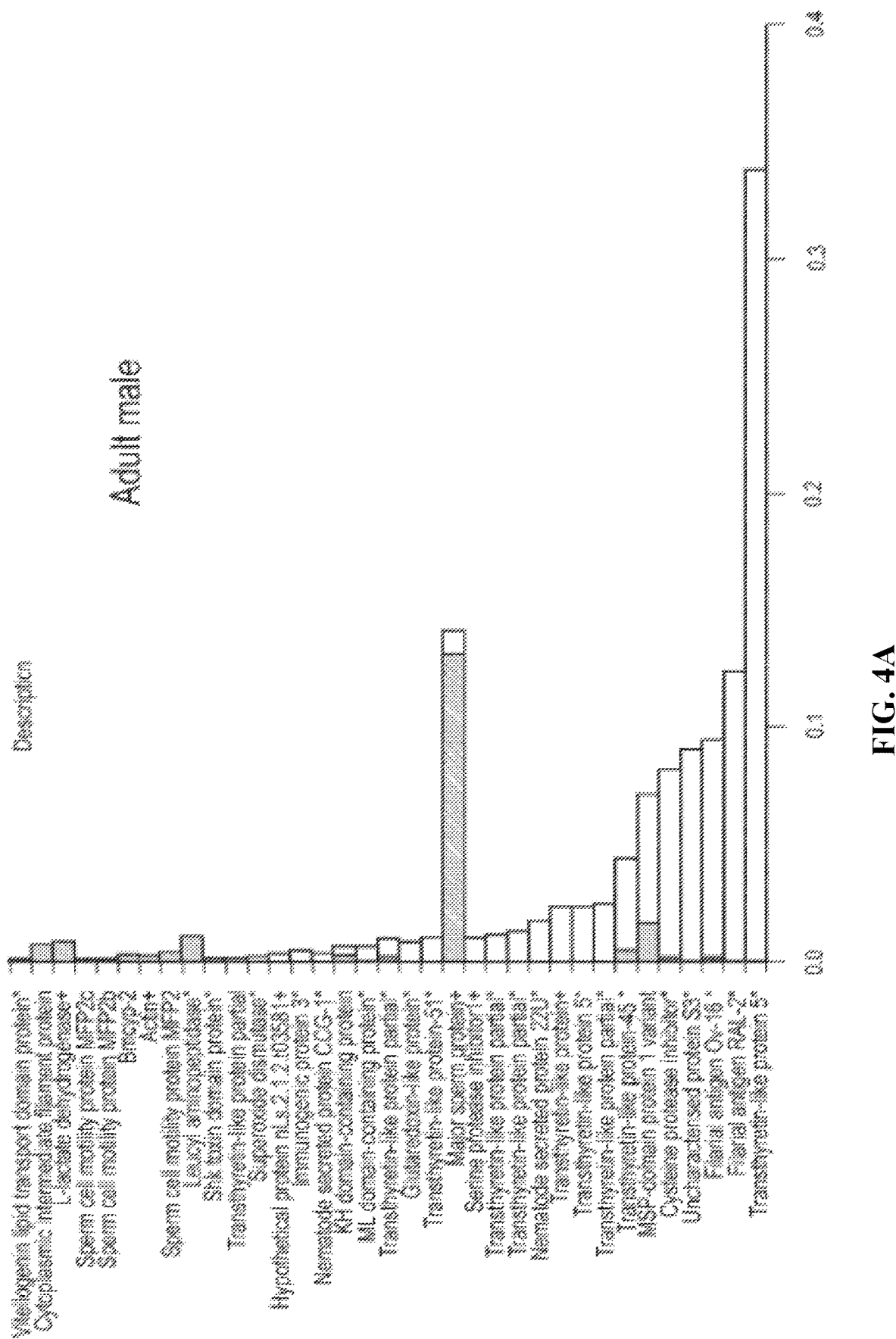

FIG. 4A. Comparison of ESP protein abundance (iBAQ) in adult stages of *L. sigmodontis*. The top 35 most abundant proteins in each ES preparation (adult male, "AM") are ranked by normalised iBAQ abundance (striped bars); the corresponding abundance in WBE is displayed for comparison (white bars) in a stacked format. Individual protein abundance values were normalised by the summed total abundance per sample. An asterisk indicates proteins with a predicted signal peptide, while predicted secretion through the non-classical pathway is indicated by a plus sign.

Figure 4B:
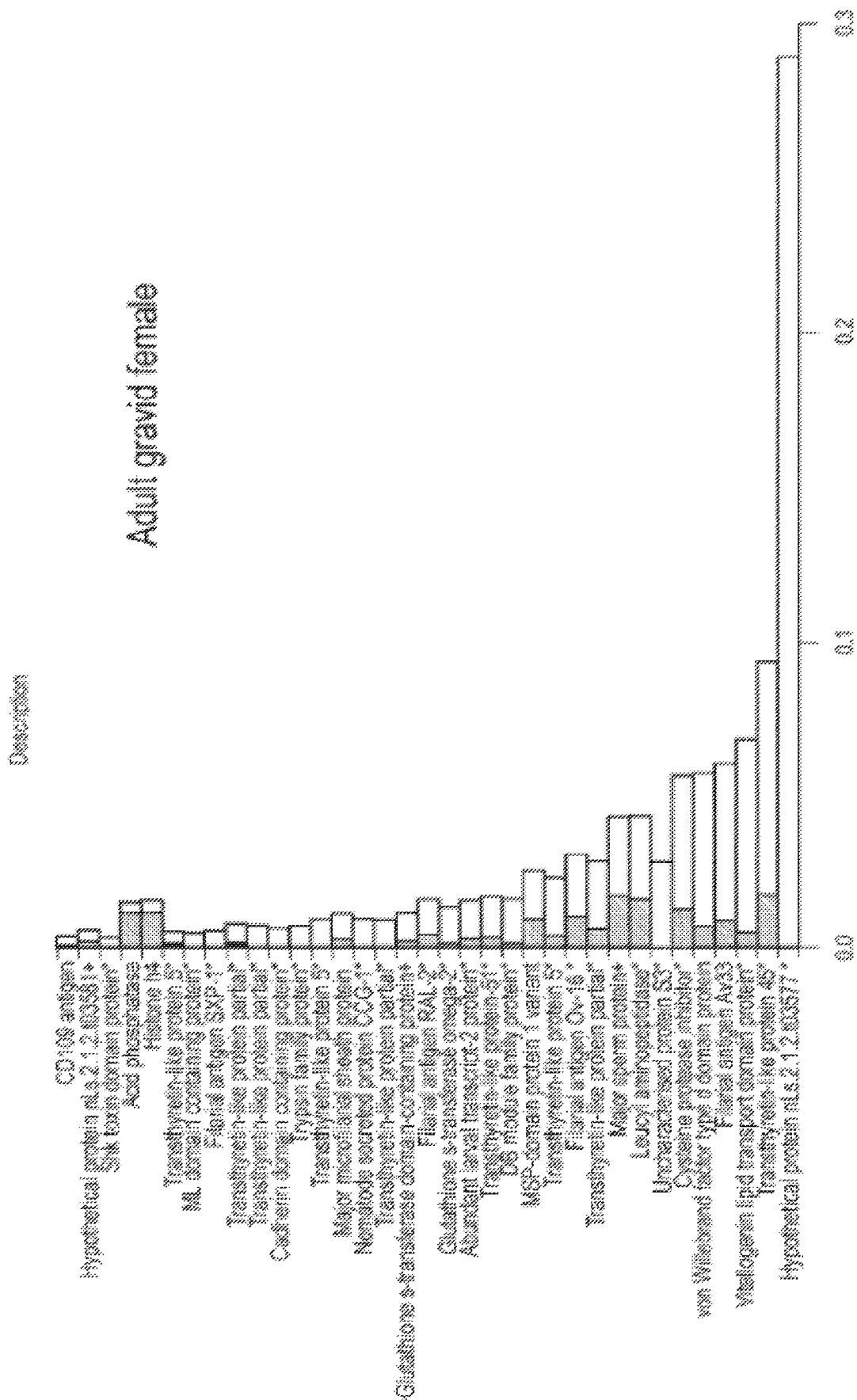

FIG. 4B. Comparison of ESP protein abundance (iBAQ) in adult stages of *L. sigmodontis*. The top 35 most abundant proteins in each ES preparation (adult gravid female, "GAF") are ranked by normalised iBAQ abundance (striped bars); the corresponding abundance in WBE is displayed for comparison (white bars) in a stacked format. Individual protein abundance values were normalised by the summed total abundance per sample. An asterisk indicates proteins with a predicted signal peptide, while predicted secretion through the non-classical pathway is indicated by a plus sign.

Figure 4C:
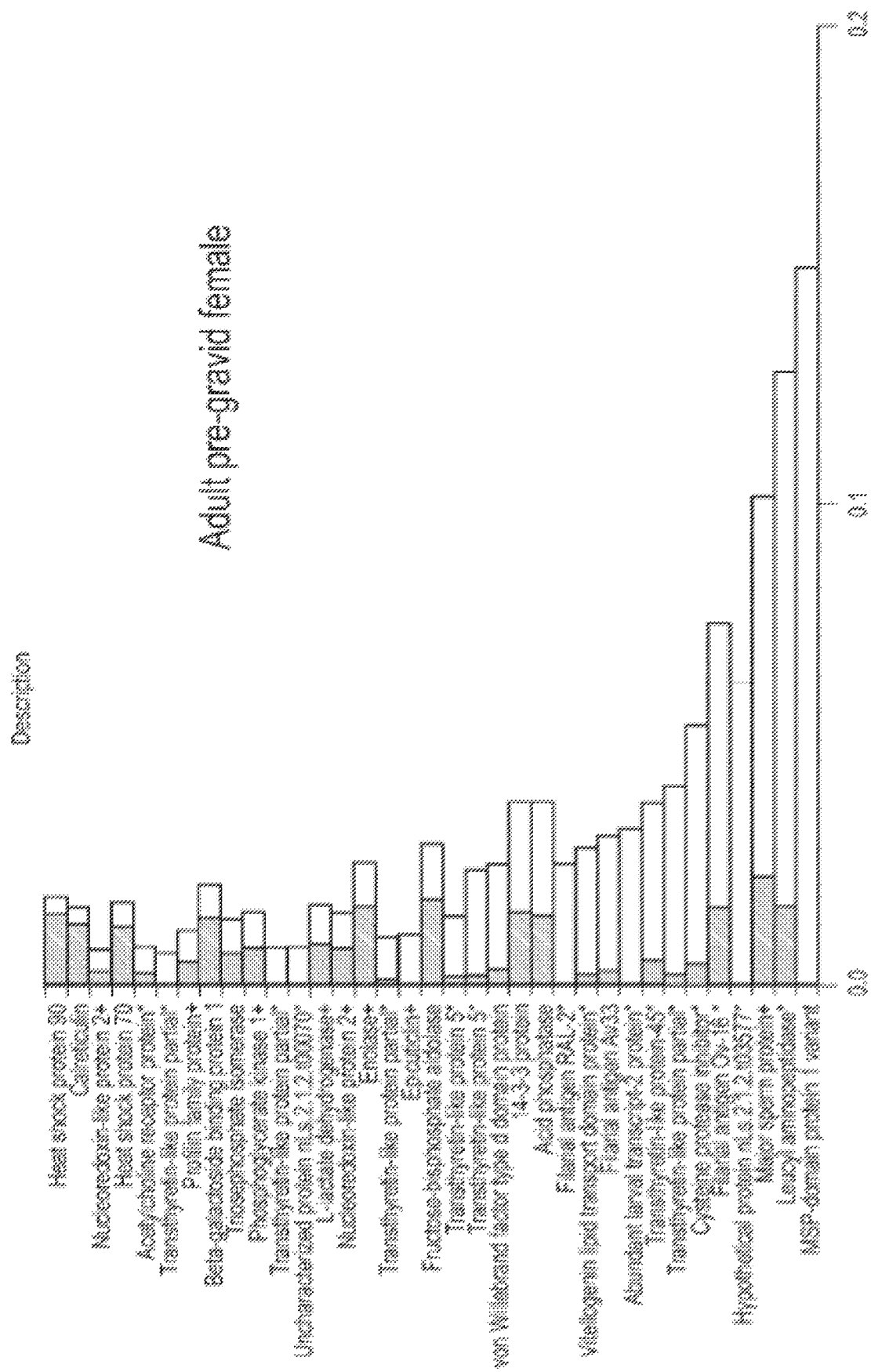

FIG. 4C. Comparison of ESP protein abundance (iBAQ) in adult stages of *L. sigmodontis*. The top 35 most abundant proteins in each ES preparation (adult pre-gravid female, "PAF") are ranked by normalised iBAQ abundance (striped bars); the corresponding abundance in WBE is displayed for comparison (white bars) in a stacked format. Individual protein abundance values were normalised by the summed total abundance per sample. An asterisk indicates proteins with a predicted signal peptide, while predicted secretion through the non-classical pathway is indicated by a plus sign.

Figure 5A:
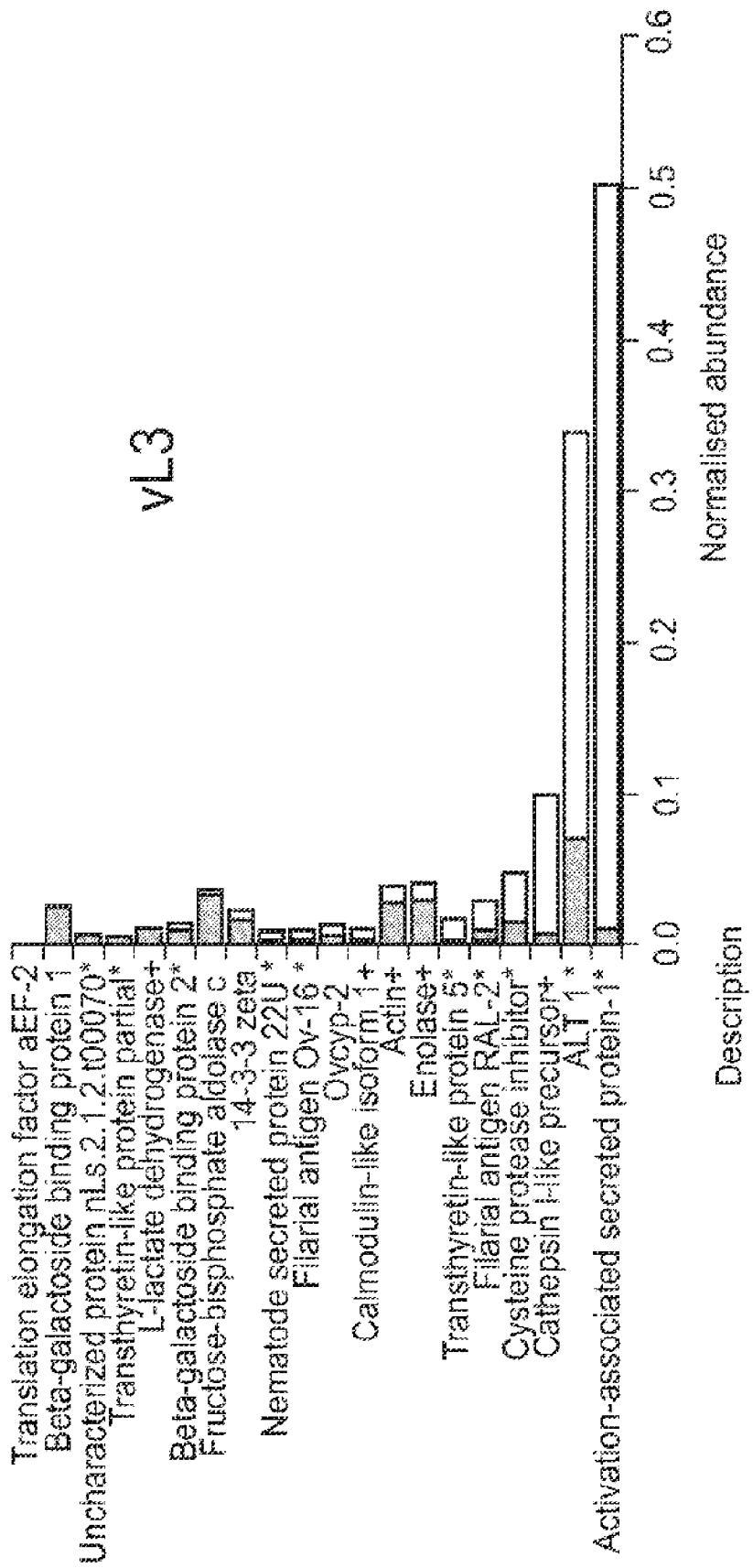

FIG. 5A. Comparison of ESP protein abundance (iBAQ) in larval stages of *L. sigmodontis*. Proteins in each ESP preparation (vL3) are ranked by normalised iBAQ abundance (striped bars); the corresponding abundance in WBE is displayed for comparison (white bars) in a stacked format. Individual protein abundance values were normalised by the summed total abundance per sample. An asterisk indicates proteins with a predicted signal peptide, while predicted secretion through the non-classical pathway is indicated by a plus sign.

Figure 5B:
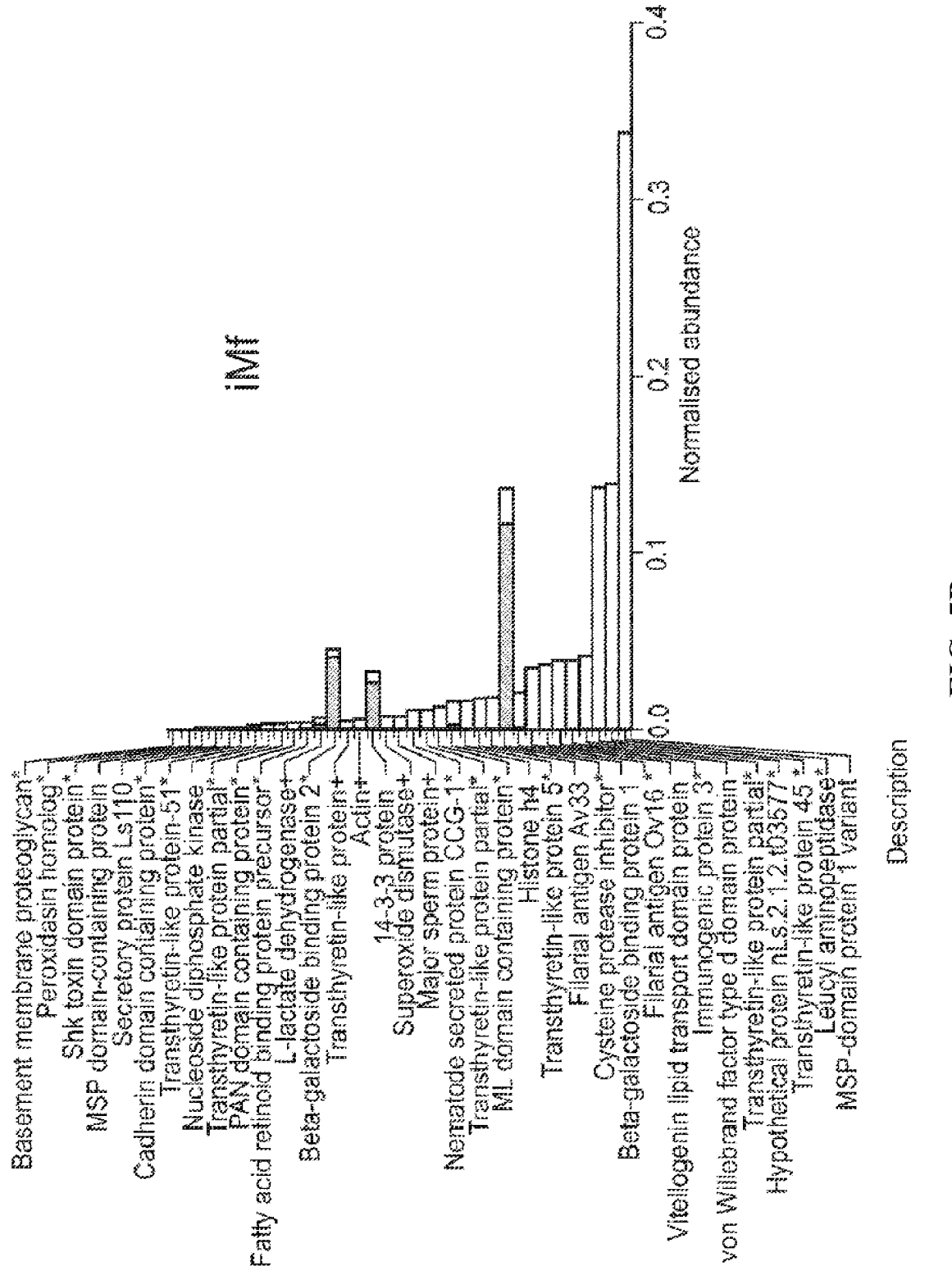

FIG. 5B. Comparison of ESP protein abundance (iBAQ) in larval stages of *L. sigmodontis*. Proteins in each ESP preparation (iMf) are ranked by normalised iBAQ abundance (striped bars); the corresponding abundance in WBE is displayed for comparison (white bars) in a stacked format. Individual protein abundance values were normalised by the summed total abundance per sample. An asterisk indicates proteins with a predicted signal peptide, while predicted secretion through the non-classical pathway is indicated by a plus sign.

Figure 6:
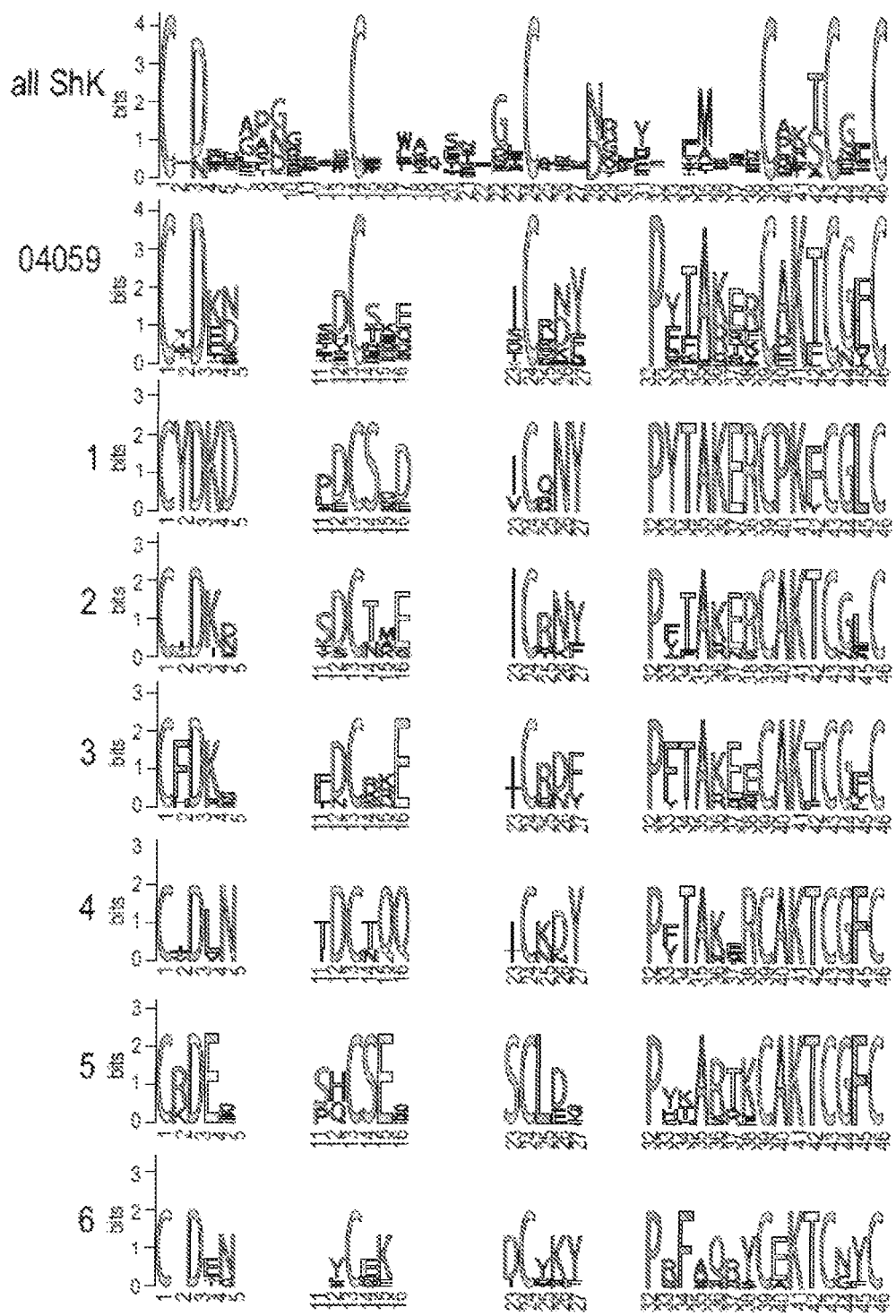

FIG. 6. The ShK domains from *L. sigmodontis* protein nLs_04059 and its orthologues in other filarial species have a distinct sequence signature. All ShK domains identified in the complete theoretical proteomes of *L. sigmodontis, B. malayi, L. loa, W. bancrofti, O. ochengi, D. immitis, Acanthocheilonema viteae* and *Ascaris suum* were extracted and aligned, and sequence logos derived from: (all ShK) all 531 domains, (04059) all domains from nLs_04059 and its orthologues, (1-6) the aligned orthologous domains 1 to 6 from nLs_04059 and its orthologues. No nLs_04059 orthologue was found in *A. suum*. As the nLs_04059 domains are relatively short, there are gaps in the sequence logos for the nLs_04059-derived domains. Numbering in all the panels is based on the full ShK alignment.

Figure 7A:
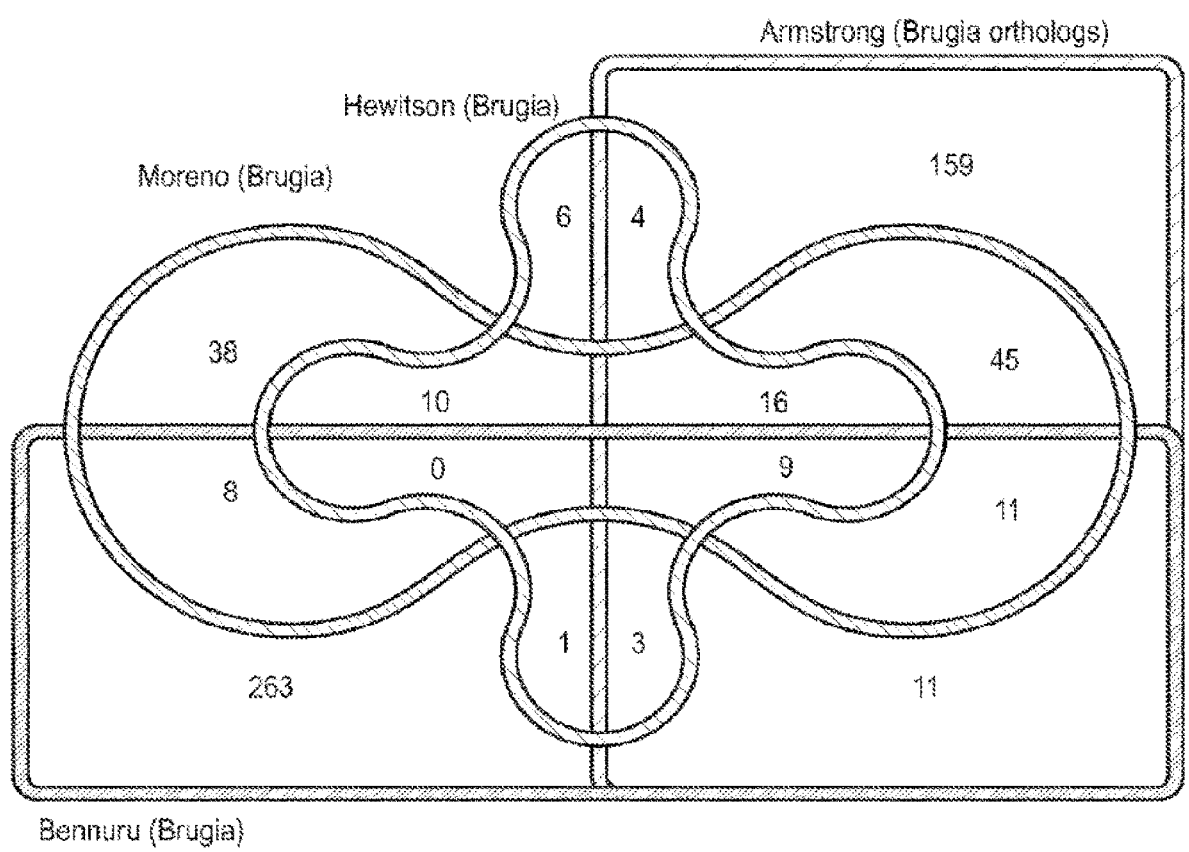

FIG. 7A. Number of adult ES proteins detected in published studies of *B. malayi* adults and comparison with orthologues present in the *L. sigmodontis* adult secretome. The study-specific and shared proteins represent combined data from both adult sexes. Note that protein identifications are those quoted by each individual study and statistical cut-offs have not been standardised. *Brugia malayi* orthologues of *L. sigmodontis* proteins were identified by reciprocal BLAST of the respective theoretical proteomes (bit score >50). The distribution of the orthologues in adult nematode ESP across three previously published studies (*B. malayi*) and the current study (*L. sigmodontis*) is displayed.

Figure 7B:
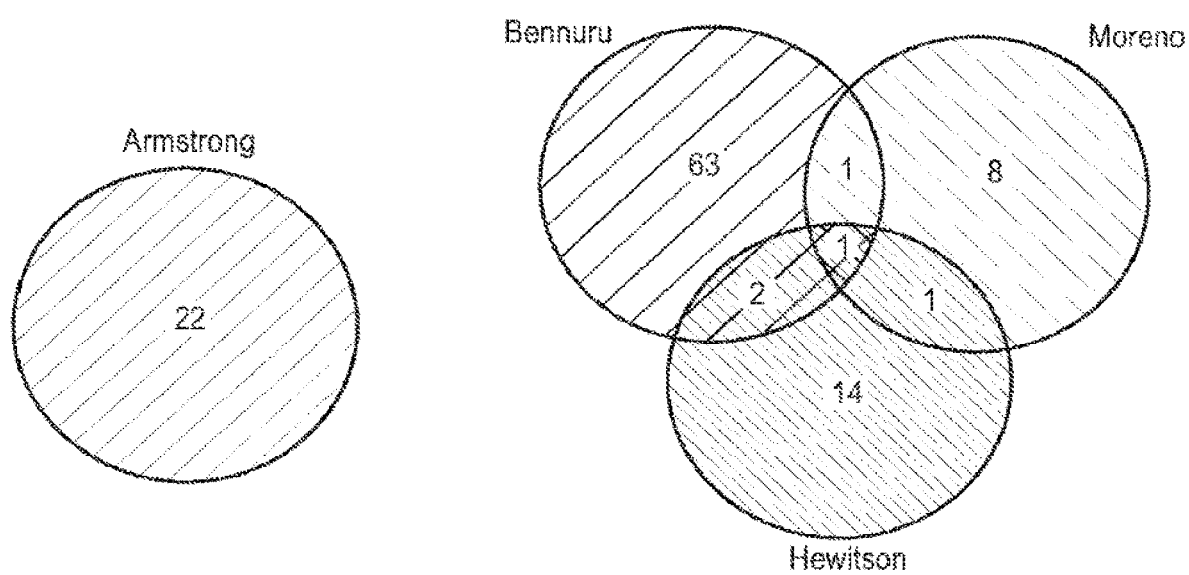

FIG. 7B. Number of adult ES proteins detected in published studies of *B. malayi* adults and comparison with orthologues present in the *L. sigmodontis* adult secretome. The study-specific and shared proteins represent combined data from both adult sexes. Note that protein identifications are those quoted by each individual study and statistical cut-offs have not been standardised. *Brugia malayi* orthologues of *L. sigmodontis* proteins were identified by reciprocal BLAST of the respective theoretical proteomes (bit score >50). The distribution of species-specific (non-orthologous) proteins is summarised.

Figure 8:
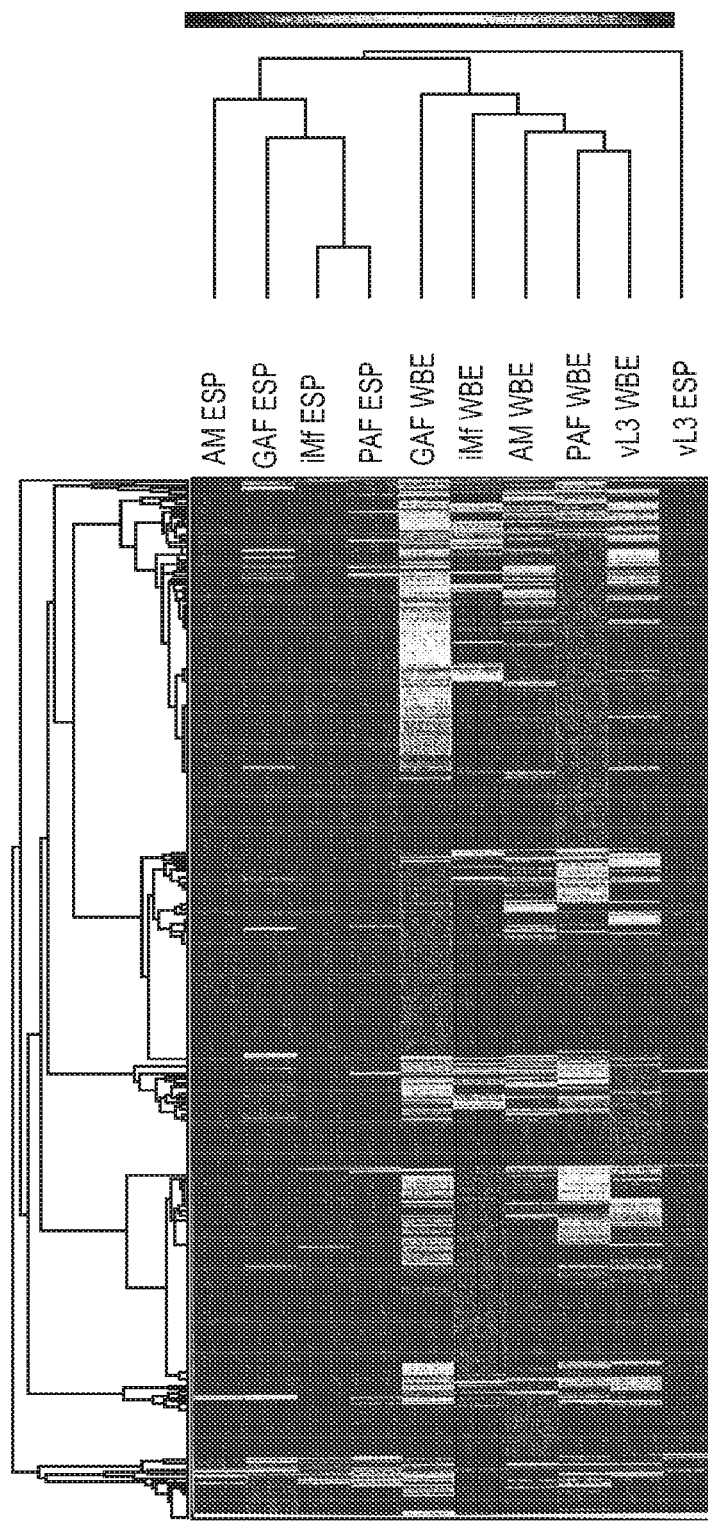

FIG. 8. Heat-map of protein profiles for excretory-secretory preparations and whole body extracts of *Litomosoides sigmodontis*. Dendrograms shown in this Figure were generated by hierarchical clustering based on pair-wise distance. ESP, excretory-secretory products; WBE, whole body extracts; GAF, gravid adult females; PAF, pre-gravid adult females; AM, adult males; iMF, immature microfilariae; vL3, vector-derived third stage larvae.

FIG. 9. Domain organisation of protein nLs_04059 from *Litomosoides sigmodontis*. Linear representation of the amino-acid sequence highlighting the signal peptide (italicised), six ShK toxin-like domains (open rectangles) containing six cysteine residues each (highlighted), and a predicted propeptide cleavage site (underlined). Domain six at the C-terminus is unique in containing two lysyltyrosine dyads (bold).

FIG. 10. Amino-acid sequence alignment of *L. sigmodontis* protein nLs_03577 and its orthologues in other filarial nematodes. Homologues of nLs_03577 were identified by BLASTp search of protein databases from sequenced nematode genomes and a transcriptome assembly for *Setaria labiatopapillosa* (G. Koutsovoulos, B. Makepeace, M. Blaxter; unpublished). No homologues were found outside the filarial nematodes. The protein sequences were aligned with ClustalOmega, and identity is indicated by a coloured scale (high identity is indicated in striped; lower identity is indicated in white).

FIG. 11. Rooted phylogenetic tree of *L. sigmodontis* protein nLs_03577 and its orthologues in other filarial nematodes. Homologues of nLs_03577 were identified by BLASTP search of protein databases from sequenced nematode genomes and a transcriptome assembly for *Setaria labiatopapillosa* (G. Koutsovoulos, B. Makepeace, M. Blaxter; unpublished). No homologues were found outside the filarial nematodes. The protein sequences were aligned with ClustalOmega and the alignment subjected to phylogenetic analysis using MrBayes version 3.2. Every $100^{th}$ generation from the final 1 million generations of a 2 million generation analysis were combined to derive the consensus shown. The tree is rooted with *S. labiatopapillosa*, in accordance with accepted systematics, and nuclear small subunit ribosomal RNA phylogeny.

Figure 12:
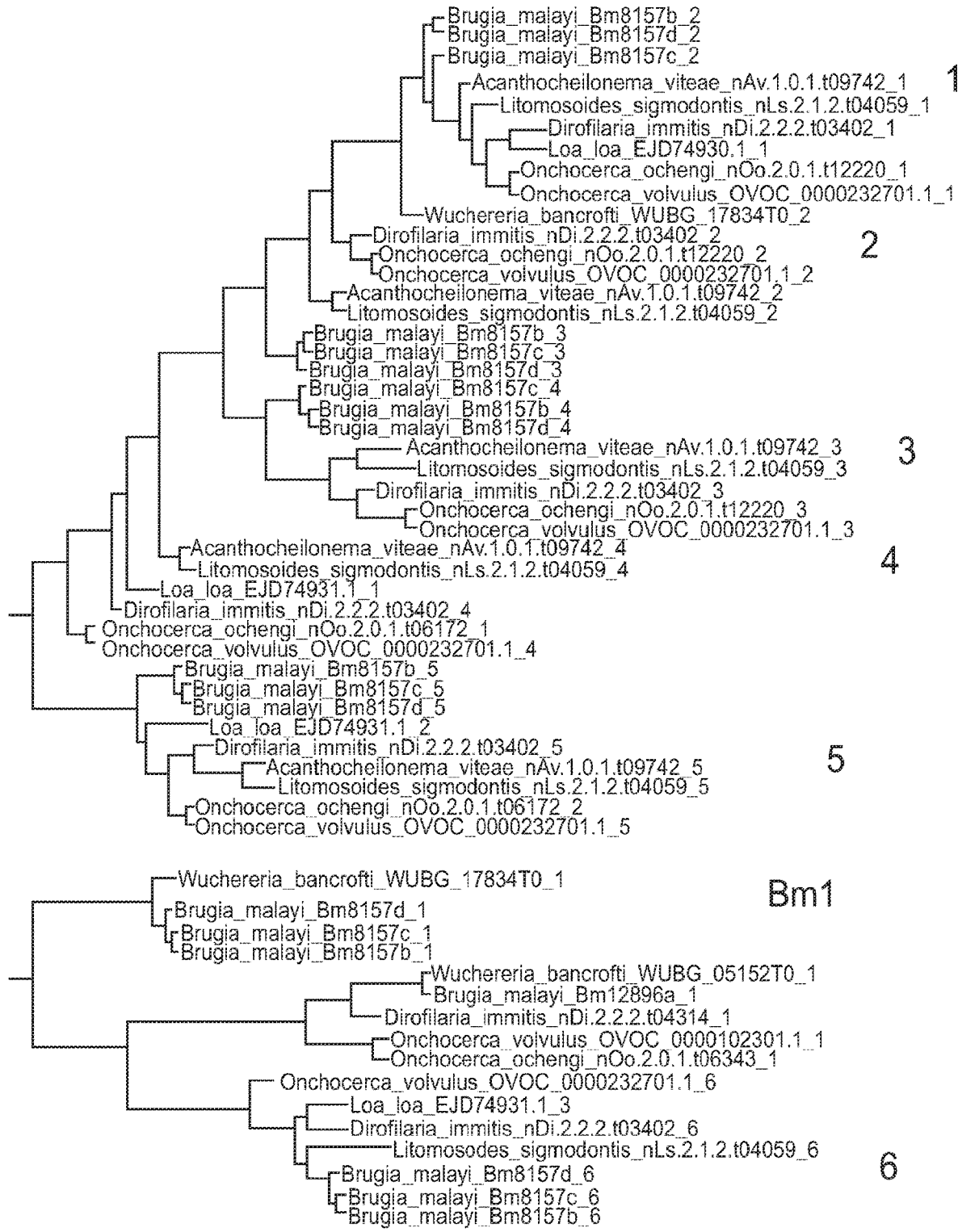

FIG. 12. Rooted phylogenetic tree of ShK domains among predicted proteins in filarial nematodes. The rooted subtrees for the six ShK domains from the nLs_04059 orthologues are shown. In *B. malayi*, domain 1 is represented by two distinct isoform clusters, one of which (Bm1) is found only in this species and in *W. bancrofti*.

Figure 13:
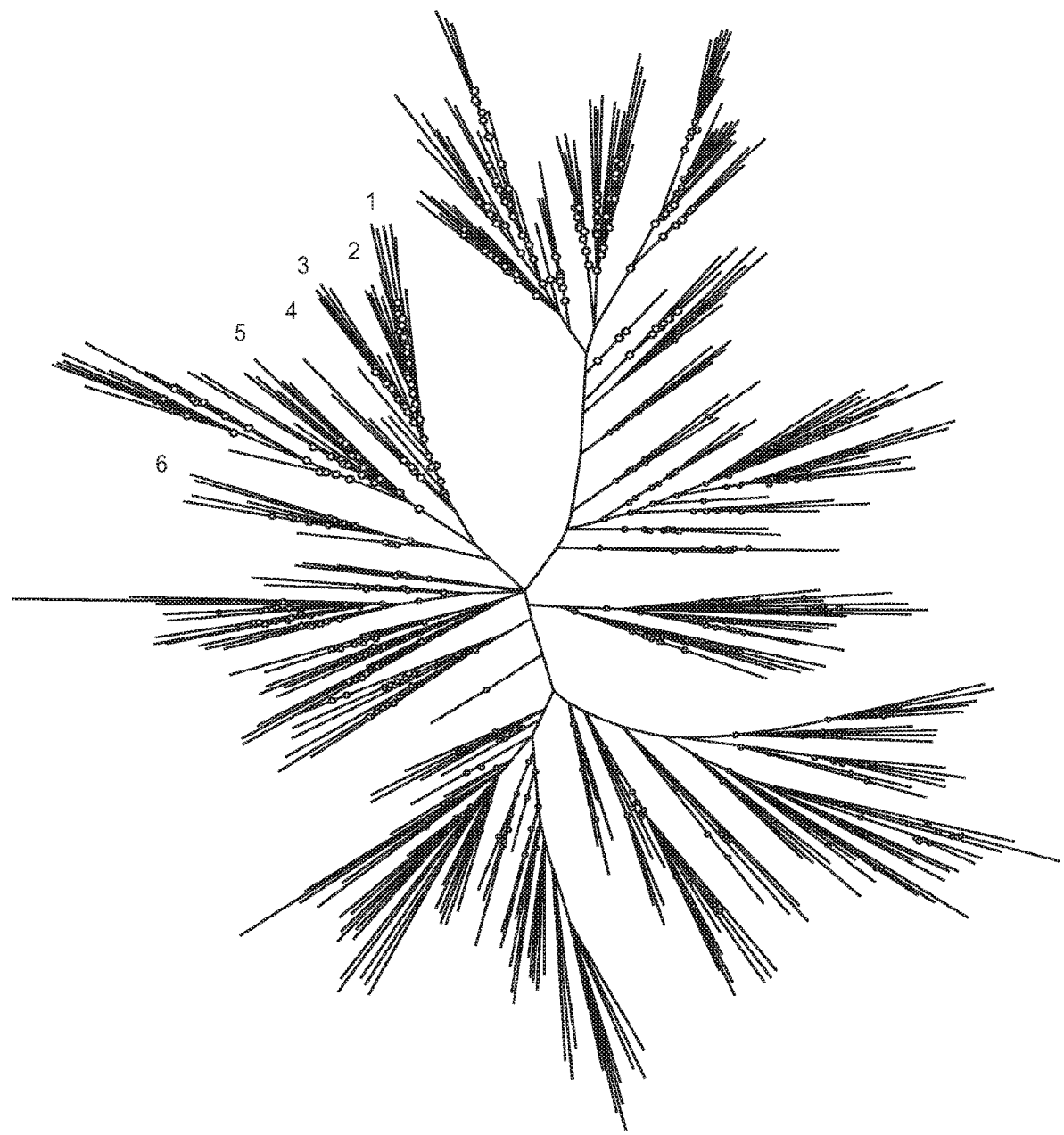

FIG. 13. Unrooted phylogenetic tree of ShK domains among predicted proteins in filarial nematodes and *Ascaris suum*. The numbers 1-6 identify the ShK domains of the *L. sigmodontis* protein nLs_04059.

Figure 14:
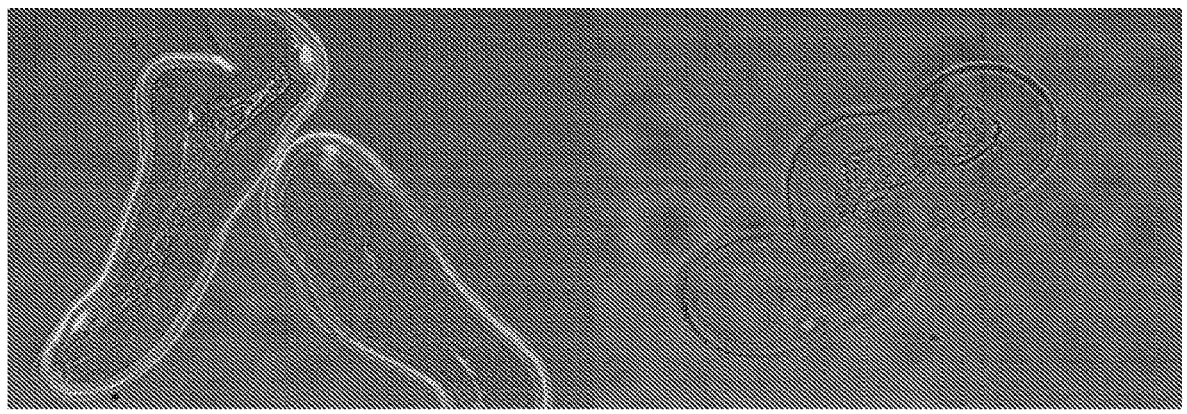

FIG. 14. Distribution of biotin in labelled and unlabelled specimens of adult *Litomosoides sigmodontis*. Fixed worm sections were incubated with streptavidin-FITC. A, Biotin-labelled works. B, An unlabelled control specimen.

EXPERIMENTAL RESULTS

Study 1

The ability of polypeptides comprising ShK domains of filarial nematode proteins to as vaccines conferring protective immunity in respect of filarial nematode infection, and the suitability of nucleic acids encoding such polypeptides to serve as vaccines, was demonstrated by the following study. The *L. sigmodontis* ShK domain containing protein used as an exemplary vaccine was designated LsShK for the purposes of this study.

Immunisations and infections were performed with female BALB/c mice, starting at ages of 6-7 weeks, with five animals per experimental group. Mice were housed in individually ventilated cages and infected subcutaneously with 30 or 40 *L. sigmodontis* infective larvae (iL3). Naïve, uninfected animals were maintained and sampled in parallel as controls for the immunological readouts.

All cloning was carried out following the recommendations of the pcDNA 3.1 Directional TOPO Expression Kit (Invitrogen). LsShK (gene ID nLs.2.1.2.t04059-RA) was amplified from a cDNA preparation of adult *L. sigmodontis* using specific primers. Fusion constructs containing single-chain anti-DEC205 antibody (DEC) upstream of the LsShK sequence were produced from ready-made constructs kindly provided by Dr. Ralph Steinman. Briefly, PCR products of genes of interest were digested with NotI and XbaI (Neb laboratory, UK), then ligated into an NotI and XbaI-digested anti-mouse dec-205 single chain antibody-ovalbumin construct (DEC-OVA) or antibody control Ig-OVA to replace the fragment of OVA gene, respectively. All plasmids were sequenced to confirm identity.

Plasmids were injected in the tibialis anterior muscle of the left leg with a 27 G needle, immediately followed by electroporation with an ECM 830 generator+Tweezertrodes (BTX Harvard Apparatus) using as settings 8 pulses, 200 V/cm, 40 ms duration, 460 ms interval. Each mouse was immunised twice separated by 2 weeks interval with 40 µg of DNA total made up by equal quantities of each plasmid species, delivered in 50 µl PBS. As a consequence, the quantity of each individual plasmid was reduced as the number of different plasmids incorporated into the inoculums increased. However, the quantity of each one remained in excess of the minimal efficient dose.

Parasite survival was determined at experiment endpoint. Adult filariae were isolated from the pleural cavity lavage fluid in 10 ml cold PBS, fixed in hot 70% ethanol and counted. Protection was calculated as:

(mean burden in primary infected animals–mean burden of vaccinated animals)/mean burden in primary infected animals.

Microfilariae were counted in 30 µl of blood after fixation in 570 µl of BD FACS lysing solution (BD Biosciences) under an inverted microscope.

Generalised linear models were used to compare the effects of different vaccine formulations on parasitological parameters as they allow more flexibility in specifying the distribution of response variables and better model fitting through Maximum Likelihood estimation.

The results of this study are illustrated in FIG. 1.

The inventors found that at day 60 post-infection, the LsShK vaccine had a modest effect on adult worm burden (~40% reduction), though this was of borderline statistical significance (p=0.07). However, the vaccinated group had no microfilariae detected in the blood, whereas the primary infection group (which received empty plasmid vector only) exhibited a median microfilaraemia of ~830 parasites per ml (p=0.005). This suggests that the medical use of ShK domains as vaccines achieves its therapeutic use through sterilising the adult female worms, or by killing migrating microfilariae before they can reach the bloodstream.

Study 2

The invention may further be understood by the skilled person on consideration of the following details of a study undertaking quantitative secretome analysis of a model filarial nematode (*Litomosoides sigmodontis*) across the parasite life cycle.

2.1 Summary

Filarial nematodes (superfamily Filarioidea) are responsible for an annual global health burden of approximately 6.3 million disability-adjusted life-years, which represents the greatest single component of morbidity attributable to helminths affecting humans. No vaccine exists for the major filarial diseases, lymphatic filariasis and onchocerciasis; in part because research on protective immunity against filariae has been constrained because the human-parasitic species cannot complete their lifecycles in laboratory mice. However, the rodent filaria *Litomosoides sigmodontis* has become a popular experimental model, as BALB/c mice are fully permissive for its development and reproduction. Here, we provide a comprehensive analysis of excretory-secretory products from *L. sigmodontis* across five lifecycle stages.

Applying intensity-based quantification, we determined the abundance of 302 unique excretory-secretory proteins, of which 64.6% were present in quantifiable amounts only from gravid adult female nematodes. This lifecycle stage, together with immature first-stage larvae (microfilariae), released four proteins that have not previously been evaluated as vaccine candidates: a predicted 28.5 kDa filaria-specific protein, a zonadhesin and SCO-spondin-like protein, a vitellogenin, and a protein containing six metridin-like ShK toxin domains. Female nematodes also released two proteins derived from the obligate *Wolbachia* symbiont. Notably, excretory-secretory products from all parasite stages contained several uncharacterised members of the transthyretin-like protein family. Furthermore, biotin labelling revealed that redox proteins and enzymes involved in purinergic signalling were enriched on the adult nematode cuticle. Comparison of the *L. sigmodontis* adult secretome with that of the human-infective filarial nematode *Brugia malayi* (reported previously in three independent published studies) identified differences that suggest a considerable underlying diversity of potential immunomodulators. The molecules identified in *L. sigmodontis* excretory-secretory products show promise not only for vaccination against filarial infections, but for the amelioration of allergy and autoimmune diseases.

2.2 Introduction

Filarial nematodes are the most important helminth parasites of humans in terms of overall impact on public health, with an annual global burden of ~6.3 million disability-adjusted life-years (1). Lymphatic filariasis (LF) or "elephantiasis", which affects populations across Africa, South Asia, the Pacific, Latin America and the Caribbean, accounts for 92% of this toll. The remainder is caused by onchocerciasis or "river blindness", primarily in sub-Saharan Africa. The major human filarial pathogens are *Wuchereria bancrofti* (responsible for 90% of LF cases), *Brugia malayi* and *Brugia timori* (geographically restricted causes of LF), and *Onchocerca volvulus* (the sole agent of human onchocerciasis). In addition, *Loa loa* affects ~13 million people in West and Central Africa. This parasite usually induces a relatively mild disease, but has been associated with severe and sometimes fatal adverse events following anthelmintic chemotherapy (2). Filarial parasites are primarily drivers of chronic morbidity, which manifests as disabling swelling of the legs, genitals and breasts in LF; or visual impairment and severe dermatitis in onchocerciasis. The filariae are also a major problem in small animal veterinary medicine, with ~0.5 million dogs in the USA alone infected with *Dirofilaria immitis* (3), the cause of potentially fatal heartworm disease. However, in domesticated ungulates, filarial infections are generally quite benign (4).

Currently, control of human filarial diseases is almost entirely dependent on three drugs (ivermectin, diethylcarbamazine and albendazole). Prevention of heartworm also relies on prophylactic treatment of dogs and cats with ivermectin or other macrocyclic lactones. Reports of possible ivermectin resistance in *O. volvulus* (5) and *D. immitis* (6) have highlighted the importance of maintaining research efforts in vaccine development against filarial nematodes. However, rational vaccine design has been constrained for several decades (7) by the intrinsic complexity of these metazoan parasites and their multistage lifecycle. Moreover, many filarial species carry obligate bacterial endosymbionts (*Wolbachia*), which may also stimulate the immune response during infection (8). As part of global efforts to improve prevention and treatment of these diseases, large-scale projects have been undertaken, including sequencing of the nematodes (9-11) and their *Wolbachia* (10, 12, 13), and proteomic analyses of both whole organisms and excretory-secretory products (ESP) (14, 15). Additionally, two studies (both on *B. malayi*) have examined lifecycle stage-specific secretomes (16, 17). In the context of vaccine design, the identification of ESP proteins and determination of their expression in each major lifecycle stage can facilitate the prioritisation of candidates for efficacy screening in animal models.

One barrier to the progression of research in the filarial field is our inability to maintain the full lifecycle of the human parasites in genetically tractable, inbred hosts. The filarial lifecycle involves uptake of the first-stage larvae (microfilariae, Mf) by a haematophagous arthropod, two moults in this vector, followed by transmission of third-stage larvae (L3) to a new vertebrate host. Two further moults occur in the definitive host before the nematodes mature as dioecious adults in a species-specific, parenteral predilection site. However, the complete lifecycle of the New World filaria *Litomosoides sigmodontis* can be maintained in laboratory rodents, including inbred mice (18). This species was first studied in its natural host (the cotton rat, *Sigmodon hispidus*) (19) [the previous designation of these isolates as *L. carinii* is taxonomically incorrect (20)]. Drawing on the full power of murine immunology, including defined knockout strains, this model has been address questions regarding the fundamental immunomodulatory mechanisms employed by filarial parasites (21), their susceptibility to different modes of vaccination, their ability to mitigate proinflammatory pathology and autoimmune disease (22), and the impact of various vaccine strategies on adult nematode burden and fecundity (23) (24). The *L. sigmodontis* model has also been central in defining the role of T-regulatory cells in filarial immune evasion (25).

Using the resource of a newly-determined genome sequence, coupled with a derivative of intensity-based absolute quantification (iBAQ) proteomics, we have examined the stage-specific secretome of *L. sigmodontis* in vector-derived L3 (vL3), adult males (AM), pre-gravid adult females (PAF), gravid adult females (GAF), and immature Mf (iMf). In addition to identifying dynamic changes in the ESP profile through the lifecycle, we show important differences in the adult secretomes of *L. sigmodontis* and *B. malayi*, especially in the abundance of two novel proteins released by female *L. sigmodontis* that lack orthologues in *B. malayi*. As has been observed in other parasitic nematodes, we find transthyretin-like family (TTL) proteins to be particularly dominant in the ESP. Leakage of uterine fluid may account for the remarkable diversity of proteins that we detect in GAF ESP, and we highlight several novel proteins that warrant evaluation in vaccine trials and as anti-inflammatory mediators.

2.3 Experimental Procedures

Ethical Considerations

All experimental procedures on the animals required for vL3 production at the Muséum National d'Histoire Naturelle were approved by the ethical committee "Cuvier" (no 68-002) and carried out in strict accordance with EU Directive 2010/63/UE and the relevant national legislation (French Décret no 2013-118, 1 Feb. 2013). All other parasite stages were harvested from animals maintained at the University of Edinburgh in compliance with a UK Home Office Animals (Scientific Procedures Act) 1986 project license and the recommendations of the local ethical review committee.

Parasites and Protein Preparations

The life cycle of L. sigmodontis was maintained in jirds (Meriones unguiculatus) infected with vL3 harvested from the mite vector Ornithonyssus bacoti. After 70-90 days, GAF and AM were recovered from the pleural cavity by lavage with serum-free RPMI 1640 medium (Life Technologies), whereas PAF were recovered 32 days post-challenge. To harvest iMf liberated in vitro, GAF culture medium was removed after 24 h and centrifuged at 1,900 g for 20 minutes (4° C.). Blood-derived microfilariae (bMf) were obtained by overlay of blood (from cardiac puncture of jirds >75 days post-infection) onto a 25% Percoll suspension, centrifugation at 1,900 g for 20 minutes (4° C.), and passage of the bMf fraction through a PD-10 desalting column (GE Healthcare) prior to culture. The vL3 larvae were dissected directly from the mite vector and washed three times in RPMI 1640 before transfer to culture vessels.

To determine the relative abundance of proteins in the secretome of each parasite stage, ESP and whole body extracts (WBE) were extracted and analysed separately. All parasite stages were incubated in serum-free RPMI 1640 supplemented with 100 U/ml penicillin, 100 µg/ml streptomycin and 1% glucose at 37° C. (5% $CO_2$) in ultra-low attachment flasks (Corning), and were confirmed to be viable during incubation by microscopic examination. The medium was replaced every 24 h, and spent media recovered at 24 h and 48 h were centrifuged at 1,900 g for 20 minutes (4° C.) in low protein-binding Oak Ridge tubes (polypropylene copolymer; Thermo Scientific Nalgene) to remove debris. To purify proteins from the supernatant, hydroxylated silica slurry (StrataClean Resin, Agilent Technologies) was added at 30 µl/ml and vortex-mixed at high speed for 2 min. Resin used for each 24 h incubation sample was reused for the respective 48 h sample to concentrate ESP prior to storage at −80° C. Initial experiments using soluble WBE (used as a proxy for ESP, as limited amounts of the latter were available) displayed no visible differences in protein profiles by SDS-PAGE using resin-bound protein compared to equivalent unbound material (data not shown). Analyses were performed with separate ESP batches in quadruplicate for GAF, triplicate for AM, and duplicate for PAF, iMf and vL3.

Soluble WBE was prepared by homogenisation in 25 mM ammonium bicarbonate, 1% RapiGest SF surfactant (Waters) and cOmplete Protease Inhibitor Cocktail (Roche) using a mini-pestle in a microcentrifuge tube. This was followed by 10 cycles of sonication on ice using a Vibra-Cell VCX130PB sonicator (Sonics & Materials, Inc.) with microprobe (10 sec sonication alternating with 30 sec incubation on ice). Homogenised samples were centrifuged at 13,000 g for 20 minutes (4° C.) and the supernatant retained. The WBE preparations were obtained from single pools of parasites for all stages except GAF and AM, where two biological replicates were available. Protein concentrations were determined using the Pierce Coomassie Plus (Bradford) Protein Assay (Thermo Scientific).

Surface Biotinylation of Live Worms

Samples of 10 adult male and five female nematodes were washed three times with pre-chilled PBS buffer and incubated for 30 min with 1 mM EZ-link Sulfo-NHS-SS-Biotin (Thermo scientific), or PBS only (negative control), at 4° C. with gentle agitation. The biotinylating solution was removed, and the reaction quenched with 100 mM glycine in PBS before washing the nematodes three times in PBS-glycine. Labelled nematodes were stored at −80° C. Surface proteins were extracted by sequential incubations in PBS buffer alone, 1.5% octyl β-D-glucopyranoside (Sigma), 0.5% SDS and then 4 M urea (all in PBS) for 1 h each (room temperature). Proteins released at each step were incubated with 30 µl of high-capacity streptavidin-agarose beads (Thermo Scientific) for 2 h at room temperature with rotary mixing. To recover bound biotinylated proteins, the supernatant was removed and the beads were washed three times in PBS and three times in 25 mM ammonium bicarbonate prior to incubation in 50 mM DTT (Sigma), 25 mM ammonium bicarbonate at 50° C. for 30 min. The supernatant was removed and the DTT diluted tenfold before digestion with 0.2 µg proteomic-grade trypsin (Sigma) overnight at 37° C. The resultant peptides were concentrated using $C_{18}$ reverse-phase spin filters (Thermo Scientific) according to the manufacturer's instructions prior to MS analysis.

To confirm efficient and specific labelling of the parasite surface, AM and GAF were fixed in 70% hot ethanol after subjection to biotin and control labelling as above. Paraffin-embedded sections (4 µm) were deparaffinised, rehydrated and blocked in 1% BSA and 0.3% Triton X-100 in PBS (blocking buffer) for 1 h (room temperature), followed by two 5-min washes in PBS with gentle agitation. The sections were incubated with streptavidin-FITC (Sigma) at a $\frac{1}{1,000}$ dilution in blocking buffer for 1 hr (room temperature), washed three times, and mounted with ProLong Gold anti-fade reagent (Life Technologies). Images were obtained on an Axio Imager.M2 fluorescence microscope (Zeiss) using Zen 2012 software (Zeiss), combining the FITC channel with brightfield illumination.

Sample Preparation for Proteomics

StrataClean Resin containing bound ESP was washed twice with 25 mM ammonium bicarbonate before suspension in 0.1% RapiGest SF, 25 mM ammonium bicarbonate. The resin samples were heated at 80° C. for 10 min, reduced with 3 mM DTT at 60° C. for 10 min, cooled, then alkylated with 9 mM iodoacetamide (Sigma) for 30 min (room temperature) protected from light. All steps were performed with intermittent vortex-mixing. The samples were then digested using 0.2 µg proteomic-grade trypsin at 37° C. overnight with rotation, centrifuged at 13,000 g for 5 min, and the supernatant removed. The resin was washed twice with 0.1% RapiGest SF, 25 mM ammonium bicarbonate and the supernatants pooled. To remove RapiGest SF, the samples were precipitated using TFA (final concentration, 1%) at 37° C. for 2 h and centrifuged at 12,000 g for 1 hr (4° C.). The peptide supernatant was concentrated using $C_{18}$ reverse-phase spin filters according to the manufacturer's instructions. The WBE samples were reduced and alkylated as above, digested with trypsin at a protein:trypsin ratio of 50:1 at 37° C. overnight, and precipitated to remove RapiGest SF as for the ESP preparations.

NanoLC MS ESI MS/MS Analysis

Peptide solutions (2 µl) were analysed by on-line nano-flow LC using the nanoACQUITY-nLC system (Waters) coupled to an LTQ-Orbitrap Velos (Thermo Scientific) MS as previously described (13, 26). Thermo RAW files were imported into Progenesis LC-MS (version 4.1, Nonlinear Dynamics) and spectral data were transformed to MGF files prior to export for peptide identification using the Mascot (version 2.3.02, Matrix Science) search engine as detailed previously (26). Tandem MS data were searched against the protein predictions from the L. sigmodontis genome and its Wolbachia symbiont, wLs [obtained from the online nematode genome of L. sigmodontis, release nLs 2.1.2, 10,246 protein sequences (M. Blaxter, S. Kumar, G. Koutsovoulos; unpublished); and release wLs 2.0, 1,042 protein sequences (27)], together with predicted proteomes for the rodent host (Mus musculus, Uniprot release 2012_08, 16,626 protein sequences; and *Meriones unguiculatus*, Uniprot release 2012_08, 223 protein sequences) and a general contaminant database (GPMDB, cRAP version 2012.01.01, 115 protein sequences). Search parameters, allowable modifications and the false discovery rate were defined as reported previously (13, 26). Mascot search results were imported into Progenesis LC-MS as XML files and analysed according to the following criteria: at least two unique peptides were required for reporting protein identifications, and an individual protein had to be present in ≥2 biological replicates to be included in the ESP dataset. Protein abundance was calculated by the iBAQ method; i.e., the sum of all peak intensities from the Progenesis output was divided by the number of theoretically observable tryptic peptides (28). For ESP and WBE, protein abundance was normalised by dividing the protein iBAQ value by the summed iBAQ values for the corresponding sample, and the reported abundance is the mean of the biological replicates. Normalised peptide intensities rather than iBAQ values were used to calculate fold-changes between control and biotinylated worm surface preparations. Mass spectrometric data have been deposited in the ProteomeXchange Consortium database (http://proteomecentral.proteomexchange.org) via the PRIDE partner repository (29) with the dataset identifier XXXXXXXXX.

In Silico Analyses of Proteins

The domain content of proteins identified in the ESP assessed using Pfam (v. 27.0) with the gathering threshold as a cut-off. A hypergeometric test for enrichment of Pfam domains in ESP proteins compared with the complete predicted proteome of *L. sigmodontis* was performed using the phyper toolkit within the R programming environment (30). The Benjamini & Hochberg step-up FDR-controlling procedure was applied to the calculated, adjusted P-values (31). Structural homologues of abundant uncharacterised proteins were identified through comparison to the National Center for Biotechnology Information non-redundant protein database (DELTA-BLAST search; E-value cut-off $1^{-03}$) and to the UniProt database (PSI-BLAST search) via the Phyre$^2$ protein fold recognition server (32). The conserved domain structure of selected, abundant ESP proteins was also interrogated in InterProScan 4 (33). Venn diagrams were created using VENNTURE (34), while for heat-maps, hierarchical cluster analysis was performed using the (1-r) distance metric in GENE-E. Prediction of classical N-terminal signal peptides, non-classical secretion signatures, mitochondrial targeting sequences, O-glycosylation sites and propeptide cleavage sites was performed using the SignalP 4.0 server (35), the SecretomeP 2.0 server (36), MitoProt (37), the NetOGlyc 4.0 server (38) and the ProP 1.0 server (39), respectively. *Brugia malayi* orthologues of *L. sigmodontis* proteins were determined using reciprocal BLAST with a bit score cut-off of 50.

ShK domains were identified in the complete predicted proteomes of the filariae *B. malayi* (9), *D. immitis* (10), *L. sigmodontis*, *Onchocerca ochengi*, *Acanthocheilonema viteae* (draft unpublished genomes available at http://www.nematodes.org/genomes/; Blaxter et al., unpublished), *W. bancrofti* and *L. loa* (11), plus the ascaridid nematode *Ascaris suum* (40) (which is an outgroup for the filarial species), using the Pfam hidden Markov model for the domain and hmmer (version 3.1b.1). Each domain was excised and a total of 531 distinct domains identified, which were aligned using ClustalOmega (41). Inspection of the alignment revealed that a subset of domains were misaligned (and therefore did not have the six cysteine residues in register with the others); these were corrected manually. The alignment was analysed for phylogenetic signal using MrBayes (version 3.2) (42) and two runs of four chains each were run for two million generations. The first million generations were discarded as burn-in after inspection in Tracer (version 1.5; A. Rambaut, unpublished: http://tree.bio.ed.ac.uk/software/tracer/) and a consensus tree was inferred from the remaining 10,000 samples taken every 100 generations. Sequence logos were generated for all 531 ShK domains, all domains from nLs_04059 and orthologues, and each of the six distinct sets of orthologous domains, using the WebLogo server (http://weblogo.berkeley.edu/) (43).

2.4 Results

Distribution of Proteins in ESP Across Parasite Lifecycle Stages

We searched ~120,000 MS spectra per lifecycle stage against protein sequences predicted from the *L. sigmodontis* and wLs genome assemblies. A total of 302 quantifiable filarial proteins (i.e., represented by ≥2 unique peptides in ≥2 biological replicates) were detected in ESP across the five lifecycle stages. A majority of these (195 proteins, 64.6%) were uniquely identified in GAF (FIG. 1b). Hierarchical clustering of the proteomic profiles clearly separated ESP and WBE (FIG. 8). The vL3 ESP data profile was distinct; not only from that of the other ESP preparations, but also from vL3 WBE (FIG. 8). The closer clustering of iMf with PAF ESP rather than GAF ESP was surprising, but may reflect the much lower complexity of the PAF and iMf ESP datasets. Strikingly, excluding GAF, fewer than six stage-specific proteins each were observed in ESP (Table 1). In vL3, these stage-specific proteins included highly expressed vaccine candidates originally identified from L3 of other filarial species, including activation-associated secreted protein 1 (ASP-1) and abundant larval transcript protein 1 (ALT-1). The functional identities of proteins restricted to other lifecycle stages were unexpected. Thus, PAF released two cuticular proteins and two antioxidant proteins that were not observed in ESP from GAF (Table 1). The only wLs-derived proteins that were quantifiable in any ESP were two components of the GroELS chaperonin complex, which were found solely in preparations from PAF and GAF (Table 3).

We explored functional distinctness of ESP from different lifecycle stages by determining protein domain overrepresentation relative to the complete predicted proteome of *L. sigmodontis*. The greatest fold-enrichment scores were observed in the AM ESP, which contained three proteins with a major sperm protein (MSP) fibre protein 2b (MFP2b) domain and 10 proteins with a TTL family domain (FIG. 2). The TTL family was also overrepresented in iMf (seven proteins) and PAF (nine proteins). Notably, PAF exhibited significant enrichment for intermediate filament and lamin-tail domains (three members each). The ESP from GAF was enriched for lamin-tail and immunoglobulin I-set domains, as well as two proteasome and two laminin families (FIG. 2). Overall, iMf, AM and PAF secreted a greater proportion of proteins with relatively low abundance in WBE than did vL3 and GAF (FIG. 3). However, all of the lifecycle stages exhibited secretomic profiles clearly distinct from WBE, in that proteins which were highly abundant in ESP tended to be rare in WBE and vice-versa (FIG. 4, FIG. 5). Identification of proteins in ESP was strongly correlated with sequence features suggesting secretion: 31.1% of ESP protein sequences were predicted to begin with a classical signal peptide, while a further 30.5% were predicted to contain an internal, non-classical secretion signature.

Abundant Proteins Released by Adult Parasites

The GAF ESP displayed the most complex composition, and the majority of the abundant proteins secreted by this stage were uncharacterised or contained conserved domains associated with very limited functional information (FIG. 4b). The dominant GAF ESP protein (nLs_03577) was unique to filarial nematodes and exhibited only very weak similarity to a bacterial P-type ATPase (Tables 4 and 5). Twelve distinct TTL family proteins were identified in GAF ESP (FIG. 4b), although only two were unique to this lifecycle stage. Another abundant GAF ESP protein (nLs_08836), also well-represented in PAF and iMf ESP, contained von Willebrand factor type-d (VWD) and cysteine-rich (C8) domains in its carboxy-terminal portion. The best match identified for nLs_08836 was an apolipophorin from *A. suum*, but nLs_08836 lacks the expected amino-terminal lipoprotein domain, and the carboxy-terminal portion displayed weak similarity to predicted zonadhesin-like or SCO-spondin proteins (Tables 4 and 5). A protein (nLs_04059) that contained six metridin-like ShK toxin domains, nLs_04059, was moderately abundant in GAF ESP and was also observed in PAF, AM and iMf secretomes (FIG. 9, 11, 12). While the ShK domain has a wide phylogenetic distribution, the particular pattern apparent in nLs_04059 is limited to filariae (Tables 4 and 5; see below for detailed analyses of this protein). Additional proteins present in GAF ESP were homologues of previously described ESP antigens from other filarial species. However, RAL-2 (44), SXP-1 (45), S3 (46) and CCG-1 (47) remain functionally obscure.

Functionally defined components of the ESP included a small cysteine protease inhibitor [CPI (48)], the omega-class glutathione S-transferases [GST (49)], the MSPs (50), and the microfilarial sheath protein (51) (FIG. 4b). Additionally, *L. sigmodontis* homologues of Av33 and ES-62, proteins known to be abundant in the ESP from adult females of other filarial species, were identified. Av33 is similar to an aspartate protease inhibitor from *A. suum* (52), whereas ES-62 is a secreted leucyl aminopeptidase (53). A secreted acid phosphatase, which may be involved riboflavin metabolism and have a role in the hydrolysis of prosthetic groups such as flavin mononucleotide and/or pyridoxal 5-phosphate (54, 55), was prominent in PAF ESP. Three of the GAF ESP proteins had putative lipid-binding regions: ML-domain proteins have been reported to interact with cholesterol and lipid A (56, 57), the conserved filarial antigen Ov16 has a putative phosphatidylethanolamine-binding domain (58), and a novel and highly abundant vitellogenin (nLs_07321) contained an amino-terminal lipid transport domain.

There was extensive overlap in the identities of the most abundant proteins in the ESP of PAF, AM and iMf compared with that of the particularly diverse GAF. These less complex ESP mixtures nevertheless contained dominant components overrepresented in individual stages. In PAF, abundant proteins included several glycolytic enzymes and two heat-shock proteins, as well as a galectin (β-galactoside-binding protein 1) and a highly unusual protein, nLs_03350, containing both C-type lectin and acetylcholine receptor domains (FIG. 4c). Abundant components of AM ESP included three isoforms of MFP2 (59) and proteins known to be highly expressed in sperm or seminal fluid, such as an extracellular superoxide dismutase (60) and a serine protease inhibitor (61) (FIG. 4a). However, AM ESP also contained several previously described but uncharacterised proteins, such as RAL-2 (44), nematode secreted protein 22U (62) and immunogenic protein 3 (63). A novel KH (RNA-binding) domain protein had homologues in other filarial species, but also weak homology to the Vasa DEAD-box helicase GLH-2 from *Caenorhabditis elegans* (Table 4), which is associated with spermatogenic chromatin (64).

Abundant Proteins Released by Larval Parasites

Characterisation of ESP from the bMf stage posed special challenges. Despite the two-stage purification process and prolonged culture in vitro, 92.4% (61 of 66) of proteins robustly quantified in bMf ESP were derived from the rodent host. The dominant serum components identified were fibronectin, complement C3, serum albumin, hemopexin, plasminogen and ceruloplasmin; while lower amounts of IgM were also detected (Table 6). Of the five quantifiable parasite-derived molecules, three were TTL proteins. To obtain characterise Mf-derived ESP in more depth, we harvested iMf from GAF cultures in vitro, separated them from the female nematodes, and proceeded with in vitro incubation. This procedure increased the detection of proteins of nematode origin to 36 (FIG. 5b), although as expected, the dominant proteins in iMf ESP closely mirrored the profile of GAF ESP (FIG. 4b). Interestingly, the two most abundant parasite ESP proteins observed in bMf, a TTL protein and a nematode-specific uncharacterised protein (nLs_03443), were not present in iMf ESP (Table 6). Non-unique but proportionally enriched proteins in iMf included two galectins (β-galactoside-binding proteins 1 and 2), a fatty acid and retinoid-binding protein (FAR-1), and a nucleoside diphosphate kinase (FIG. 5b), all of which are known to be expressed throughout the filarial lifecycle (65, 66). In addition, Ls110, which is secreted from the uterine epithelium during embryonic development (67), was detected in iMf ESP but not iMf WBE. Conversely, the major sheath proteins Shp1a and Shp4 were found in iMf WBE but were not secreted (supplemental Table S1). Another distinctive feature of the iMf ESP was the overrepresentation of two proteoglycan core proteins: a perlecan-like protein that exhibited moderate similarity to UNC-52 from *C. elegans* (Table 4 FIG. 5b) (68); and a chondroitin proteoglycan (CPG) containing six peritrophin-A chitin-binding domains, which was distantly related to *C. elegans* CPG-2 (69) (Tables 3 and 4). However, a large (~250 kDa predicted mass) plasminogen-apple-nematode (PAN) domain protein, which displayed weak similarity (Table 4) to the predicted mucin SRAP-1 from *C. elegans* (70), was more abundant than either of the proteoglycans in iMf ESP (FIG. 5b). Finally, an apparently novel peroxidasin-like protein with orthologues in other filarial nematodes and more distant relatives in *A. suum* and *Caenorhabditis briggsae* (Table 4) was also identified in iMf ESP (FIG. 5b).

Although ESP from the vL3 stage was the least diverse dataset in our study, it showed a distinctive repertoire of highly abundant proteins. Thus, vL3 ESP was composed of previously characterised filarial proteins that are known to be uniquely expressed or enriched in this stage [such as ASP-1 (71), ALT-1 (72), and cathepsin-L-like protease (73)], and other antigens that were well represented in ESP from other stages (RAL-2, CPI-2, Ov16 and β-galactoside-binding proteins) (FIG. 5a). The nematode secreted protein 22U was moderately abundant in the *L. sigmodontis* vL3 ESP preparations (FIG. 5a), but apparently is not expressed in vL3 of other filarial species (62). This stage may be relatively quiescent in terms of secretory activity until they adapt to the mammalian host and undergo the third moult. Analysis of ESP from moulting L3 identified fivefold more proteins than from vL3 ESP in *B. malayi* (17).

Phylogenetics of Novel, Filaria-Specific ESP Proteins

The most abundant protein in GAF ESP, nLs_03577, is an enigmatic, uncharacterised molecule with a predicted MW of 28.5 kDa and a lack of conserved domains, with the exception of a classical N-terminal signal peptide. Downstream of the signal peptide, moderate to high levels of sequence conservation were apparent across the Filarioidea in the N-terminal portion (FIG. 10). However, the C-terminal segment displayed low complexity and was highly variable between filariae, with two isoforms in *B. malayi* diverging in this region only (FIG. 10). The *L. sigmodontis* protein was predicted to contain six potential N-linked and 11 O-linked glycosylation sites, as well as propeptide cleavage sites at positions 31 and 147. The former cleavage site was absolutely conserved within the Filarioidea, despite some variation in the motif, whereas the latter (at position 154 of the consensus) was unique to *L. sigmodontis*. These observations suggest that several processed isoforms of nLs_03577 might be secreted by *L. sigmodontis*. Phylogenetic analysis of nLs_03577 orthologues confirmed that this protein is restricted to the Filarioidea, with no representatives in *A. suum* or other non-filarial nematodes. The base of the tree was poorly resolved due to the lack of signal in the C-terminal portion (FIG. 11). However, nLs_03577 clearly clustered with an orthologue in the rodent filaria, *A. viteae*, while orthologues in *D. immitis* and *Onchocerca* spp. formed the most distant grouping (FIG. 11).

The ShK domain protein nLs_04059 was a particularly distinctive molecule identified in all ESP preparations except vL3. One other *L. sigmodontis* ShK domain protein, the astacin protease nLs_03368, was a rare component of GAF ESP only (Table 3). The ShK domain (or metridin-like toxin domain, also known as the SXC or six-cysteine domain) was first identified in cnidarian venoms, but is particularly abundant in nematode proteomes (74), where it is associated with secreted proteins. The prototypic ShK peptide (from the cnidarian *Stichodactyla helianthus*) is a type 1 toxin that blocks voltage-gated potassium channels, and synthetic analogues are currently under development as a therapy for autoimmune diseases, in which Kv1.3 channels expressed by effector memory T-lymphocytes are specifically targeted (75). Although nLs_04059 was not especially abundant in any ESP preparation, its presence in the secretomes of all mammalian-derived stages and its unusual domain structure (FIG. 9) suggest a potentially immunomodulatory role.

The nLs_04059 protein has the largest number of ShK domains (six) of any protein in *L. sigmodontis*. We identified orthologous genes in all the other filarial nematode genomes, each containing six ShK domains (FIG. 12). The nLs_04059-like ShK domains form a distinct subset of all filarial and *A. suum* ShK domains (I FIGS. 12 and 13), with a striking pattern of conservation particularly around the last three universally-conserved cysteine residues (FIG. 6). A proline residue (at position 32 of the alignment, but residue 17 of the nLs_04095 domains) was also strikingly conserved in the nLs_04059 domains (FIG. 6), but not common in the full set of 531 domains. In nLs_04059 and its orthologues, the six ShK repeats are separated by five low-complexity spacers (27-104 amino acids) (FIG. 9). Some spacer domains were conserved, but others showed variation in the pattern and length of low complexity, serine-rich regions. The spacer domains have no clear similarity to other proteins, but by analogy to the ShK mucins of the ascaridid *Toxocara canis* (76), they could be recipients of O-linked glycan decorations. There are 65 potential O-glycosylation sites on nLs_04059. However, by geLC-MS we found that nLs_04059 migrated exclusively at the expected molecular weight of the unmodified mature protein (~52 kDa), ruling out a mucin-like structure (data not shown). This protein also contained two lysyltyrosine dyads located within the C-terminal ShK domain (FIG. 9). Since a lysyltyrosine dyad is essential for binding of type-1 cnidarian peptide toxins to potassium channels (77), this could be related to Kv1 channel-blocking activity. Notably, one lysyltyrosine dyad in ShK domain 6 is conserved in many (although not all) orthologues in other species (FIG. 6).

Proteins Associated with the Adult Nematode Surface

The nematode cuticle is the critical interface between the parasite and the immune system of its host (78). Surface-associated proteins may simply mirror ESP, perhaps by passive adsorption of released material, or comprise a distinct component of the exoproteome. Live AM and GAF nematodes were surface-labelled incubated with Sulfo-NHS-SS-Biotin and fractionated. Immunofluorescent imaging of fixed nematode sections confirmed that biotin labelling was largely confined to the cuticular layers (FIG. 14). Low levels of endogenous biotin were present within internal structures as expected. We identified five proteins that were present in biotin-labelled AM extracts but not unlabelled controls and 11 proteins in biotin-labelled GAF (Table 2). In addition, a further four (AM) and 39 (GAF) proteins were enriched by more than 50-fold in biotin-labelled samples relative to unlabelled controls (Table 7), suggesting that these molecules were abundant on the parasites' surface but may also be associated with endogenous biotin. There was considerable overlap between ESP and biotin-labelled protein profiles in both sexes. However, AM and GAF displayed two and 12 proteins, respectively, that were uniquely present in surface-labelled extracts (Table 2 Table 7). Conversely, many of the highly abundant ESP proteins, such as nLs_03577, the vitellogenin nLs_07321, uncharacterised protein S3 and ES-62 were not detected in biotin-labelled extracts.

A striking feature of the surface-associated proteins was the presence of two ectoenzymes involved in purinergic signalling. These were an adenylate kinase predominant in AM extracts and a purine nucleoside phosphorylase found exclusively found in GAF extracts (79) (Table 2, Table 7). A homologue of complement component 1, q subcomponent-binding protein was identified in GAF surface-labelled extracts. Like the human homologue, the *L. sigmodontis* protein contained an N-terminal mitochondrial import signal sequence, although the former is expressed in a number of extramitochondrial locations, including on the surface of lymphocytes, endothelial cells, dendritic cells and platelets (80). These proteins may play a role in immunomodulation, as purinergic signalling is known to regulate lymphocyte trafficking (79), while the complement component 1q receptor is involved in vasodilation via the generation of bradykinin (80).

Surface extracts from AM contained a homologue of the actin-binding protein, calponin, which has been localised to both striated muscle and the cuticle in adult *O. volvulus* (81). The GAF surface extracts contained two proteins, protein disulphide isomerase and a leucine-rich repeat family protein, both of which have previously been associated with cuticle synthesis in filariae and *C. elegans* (82, 83). Stress response-related proteins were also well represented on GAF (including thioredoxin peroxidase (84), aldehyde dehydrogenase, a thioredoxin-like protein and heat-shock proteins), as were several enzymes of pyruvate metabolism (Table 2 and Table 7). Notably, the endosymbiont-derived *Wolbachia* surface protein was found to be accessible to surface biotinylation in GAF.

Comparison with the Secretome of Adult *B. malayi*

The ESP from several lifecycle stages of *B. malayi* have been described previously (14, 16, 17). In these three studies, the only common stage was adult [with both sexes cultured together in (14)]. Of 297 proteins identified in adult

*L. sigmodontis* ESP, 92.6% had an orthologue in *B. malayi*. However, the majority (61.6%) of these *B. malayi* orthologues were not observed in the *B. malayi* secretome (FIG. 7a). Analysis of Pfam domains failed to indicate any significant enrichment in this unique dataset (data not shown). Conversely, although each *B. malayi* study revealed a surprising number of study-specific secreted proteins, orthologues of the proteins reported in all three *B. malayi* secretomes were also detected in adult *L. sigmodontis* ESP (FIG. 7a). This common core included leucyl aminopeptidase, enolase, triosephosphate isomerase, β-galactoside-binding protein 1, acetylcholine receptor protein, cyclophilin-5 and macrophage migration inhibitory factor-1. The 22 *L. sigmodontis* adult ESP proteins that lacked *B. malayi* orthologues (FIG. 7b) included two of the most highly abundant GAF ESP molecules (the vitellogenin nLs_07321 and the VWD protein nLs_08836), together with secretory protein Ls110 and two superoxide dismutase isoforms. Although the *B. malayi* secretome studies identified a total of 90 proteins that did not have orthologues in *L. sigmodontis* (FIG. 7b), only one (cuticular glutathione peroxidase) was observed in all three studies. Since standardised quantification methods were not used for our *L. sigmodontis* and the published *B. malayi* studies, it is difficult to determine whether adult *B. malayi* and *L. sigmodontis* differ in their levels of secretion for individual ESP proteins. However, in terms of rank abundance, triosephosphate isomerase, macrophage migration inhibitory factor-1, and γ-glutamyl transpeptidase were reported to be grossly overrepresented in adult *B. malayi*; whereas adult *L. sigmodontis* ESP was enriched for uncharacterised protein nLs_03577 (orthologous to Bm1_38495), TTL protein nLs_09750 (orthologous to Bm1_43635), and homologues of Av33 and S3 (Table 3). Proteins that were apparently equally abundant in relative terms between each species included leucyl aminopeptidase and homologues of CPI-2 and Ov16.

2.5 Discussion

Quantifying the Secretomes of a Model Filarial Nematode

Filarial nematodes exact a significant burden of morbidity in human populations and are important pathogens of companion animals. While efficacious anti-filarial drugs exist, the spectre of the evolution of genetic resistance to these is ever-present (5, 6), and alternative routes to treatment are required. It would be preferable to be able to prevent infection as well as treat patent disease, and thus an anti-filarial vaccine would be an extremely valuable addition to medical and veterinary treatment options (85). The ESP released by parasites into their hosts have been the target of vaccine development for decades, but the understanding of these molecules in filarial nematodes is limited. Whereas previous studies have catalogued the proteins inferred to be present in filarial ESP, quantitative assessments of their abundance have not been explored previously using an intensity-based approach. Using the model rodent filarial nematode *L. sigmodontis*, it is possible to prepare material from across the nematode lifecycle, and thus examine the different vertebrate-parasitic stages in detail. Applying semi-quantitative MS analysis of ESP, we identified secreted proteins and determined their abundance, limiting our analysis to 302 proteins that could be robustly quantified using ≥2 unique peptides.

The Secretome of Adult Nematodes

In *L. sigmodontis*, GAF was responsible for the majority of ESP proteomic diversity. The other four lifecycle stages examined contributed only 11 proteins (3.6% of the total) that were not present in GAF ESP. This finding contrasts with a qualitative analysis of *B. malayi* secretomes comparing adults, Mf and L3, and incorporating data obtained from single-peptide hits, which found that Mf contributed the greatest proportion of unique proteins (17). However, an earlier assessment of the *B. malayi* GAF, AM and Mf secretomes concluded that GAF produced the greatest number of unique hits (16), suggesting that methodological differences may underlie these contrasting results. The diversity of GAF ESP is consistent with the material containing not only somatic adult ESP, but also proteins released from the reproductive tract that derive from the processes of oogenesis, fertilisation and embryonic development in utero (all filarial pathogens are ovoviviparous).

Nematode sperm are acutely sensitive to aerobic damage (86). The AM ESP contained proteins suggestive of roles in protection of sperm against oxidants and other stressors, including superoxide dismutase, a serine protease inhibitor and a glutaredoxin-like protein. Glutaredoxins are thiol-containing antioxidant proteins, and *C. elegans* GLRX-21 plays a key role in mitigating selenium toxicity (87). Mammalian seminal fluid accumulates selenium, which if in excess, can impede sperm motility (88). A homologue of the serine protease inhibitor is secreted by *A. suum* during the acquisition of motility and contributes to sperm competition by inhibiting the activation of surrounding spermatids (89). Lysis of sperm during aerobic culture may account for the high levels of MSPs observed in AM ESP and in ESP obtained from PAF, GAF and iMf. Female nematodes are fertilised some weeks before the first Mf are produced (90), and the dominance of MSPs in PAF ESP indicates that leakage of sperm from the female reproductive tract occurs before parturition.

Several unique antioxidant proteins (nucleoredoxin-like protein-2, glutathione reductase and translationally-controlled tumour protein) were found in PAF ESP, suggesting an enhanced requirement for protection during this stage. In *B. malayi*, homologues of the nucleoredoxin-like proteins, which resemble large thioredoxins (91), are present in ESP but do not exhibit stage-specific expression (92). Two unique cuticle biosynthesis related proteins were also released by PAF, suggesting that cuticular remodelling occurs during their final stages of growth. This may result in increased susceptibility to immune-driven oxidative stress or damage during copulation (93). Heat-shock proteins, which were overrepresented in PAF ESP, were detected previously in *B. malayi* adult nematode ESP (94).

The Mature Microfilarial Secretome is Dominated by Host Proteins

In many filarial nematodes, microfilariae are enclosed in a proteinaceous sheath comprising an inner layer that originates from the eggshell and an outer layer that is produced by secretions in the distal portion of the uterus. Five major structural proteins have been identified in the *L. sigmodontis* sheath, some of which are synthesised in the developing embryo and others in the uterine epithelium (51), but none of these were found in iMf ESP, indicating that they are stable components. Many host serum proteins were released from bMf in culture. These are likely to derive from specific interactions with the parasite surface, perhaps reflecting a tension between the nematode exploiting the host and the host immune system recognising the parasite. The finding of host at the Mf surface is not new, as five serum components were only proteins released by SDS extraction of *L. sigmodontis* Mf sheaths (95), and human serum albumin has been detected on the sheath surface of *W. bancrofti* Mf (96), but is generally not found on *Brugia* spp. Mf (97). The *L. sigmodontis* sheath is permeable to molecules of up to 70 kDa (98), and therefore might retain some host proteins after transfer to culture. However, several abundant serum proteins that we detected in bMf ESP are considerably larger than this (for example, ceruloplasmin and fibronectin) and thus must be either adsorbed onto the sheath surface or proteolytically processed prior to uptake. Hemopexin and ceruloplasmin have roles in heme and copper transport (99), respectively; hence, they may be exploited as a source of essential cofactors by the parasite.

Several parasite-derived products were identified as secreted by iMf, including Ls110 [a protein localised in the uterine lumen and variably present on iMf, but absent from bMf (67)] and two possible proteoglycan core proteins. Accordingly, large glycoproteins (~200 kDa) have been described from *B. malayi* ESP (100). The closest *C. elegans* homologue of the perlecan-like proteoglycan, UNC-52, is a major component of the basement membrane of contractile tissues, including the pharynx and anus in developing embryos and subsequent stages (68). The *L. sigmodontis* iMf-derived CPG-like protein is predicted to have chitin-binding domains and may function in eggshell and sheath development. In *C. elegans*, CPGs form an inner layer that binds to the central chitinous layer of the eggshell, maintaining the perivitelline space around the embryo (101) forming a barrier to prevent polyspermy (102). In *L. sigmodontis*, chitin has been detected in the oocytes and zygotes, although it is absent from the iMf sheath (103). The degradation of chitin during Mf sheath development in utero may release the underlying CPG, which is highly soluble (101), into the surrounding milieu. The origin and roles two of the other novel proteins that were enriched in iMf ESP is less clear. The closest homologue in *C. elegans* of the PAN domain protein is SRAP-1, which is expressed in the hypodermis, central nervous system and vulva of developing larvae and is secreted onto the cuticle surface during moulting (104). In *C. elegans*, peroxidasin PXN-2 is located in the extracellular matrix and is required for late embryonic elongation, muscle attachment, and motoneuron axon guidance choice (105).

The Abundant Uncharacterised Proteins Released by Gravid Adult Female Nematodes

We identified four abundantly secreted or excreted proteins, found predominantly in GAF and iMf ESP, that had not been reported previously. Two have only marginal similarity to other proteins: nLs_03577, which displayed a significant match to a P-type ATPase (but lacked an ATPase domain), and nLs_08836, which showed some similarity to zonadhesin, a VWD protein located in the head of mammalian sperm (106). However, we note that nLs_08836 is not an orthologue of the *C. elegans* zonadhesin-domain protein, DEX-1 (107). The third novel protein, nLs_07321, is a vitellogenin. In *C. elegans*, vitellogenins are expressed exclusively in the intestine, where they bind cholesterol and transport it via the body cavity to the gonad (108). Subsequently, oocytes internalise the protein and its lipid cargo by receptor-mediated endocytosis and store it in yolk granules (108). Several vitellogenins have also been identified in ESP derived from adults of the oviparous gastrointestinal nematode, *Heligmosomoides polygyrus* (109). The fourth protein, the ShK domain protein nLs_04059, was distinct from other proteins containing this motif in nematodes, both in the number of domains and their specific sequence. Its relative abundance, distinctiveness and presence in all the filarial species surveyed suggest that it may be a viable vaccine candidate for both human filarial diseases and canine heartworm. Its role in vivo may be to interfere with the development of acquired immunity by inhibiting the Kv1 channels of memory T-cells in a manner analogous to the activity of cnidarian ShK toxins (75).

The enigmatic TTL family has emerged as one of the most typical and widespread findings in ESP from both zoo- and phytoparasitic nematodes (110). In *C. elegans*, there are 63 transthyretin genes, many of which are secreted and apparently upregulated in response to infectious challenge, but only TTR-52 has been ascribed a physiological function [phagocytosis of apoptotic cells (111)]. In the phytoparasite *Radopholus similis*, Rs-ttl-2, which is closely similar to one of the most abundant *L. sigmodontis* TTL proteins (nLs_07576; found in ESP from all stages except vL3 in our study), was localised to the ventral nerve cord (112). A second *R. similis* TTL family member, Rs-ttl-1, was expressed only in the vulval region (112), and a homologue of this molecule (nLs_07332) was detected in iMf WBE only. Furthermore, in the ruminant parasite *Ostertagia ostertagi*, a TTL family (Oo-TTL-1) was a major component of ESP and could be immunolocalised to the pseudocoelomic fluid of adult worms (113). In our study, a *L. sigmodontis* homologue of Oo-TTL-1 (nLs_09750) was abundant in all ESP preparations except those of vL3.

Uterine Fluid as a Source of Nematode and Endosymbiont Products

Proteins excreted or secreted from filarial nematodes could be derived from a number of routes. In addition to oral secretions from the oesophageal glands and release of faecal material from the anus, nematodes also secrete material from the anterior sensory glands (amphids) (114) and the secretory pore, and may also void material from the genital openings during copulation and release of Mf. Proteins can also be released from the hypodermis through transcuticular secretion (115), especially during moulting, and exosome release may also be important (116). From our data, we suggest that vulval excretion is the main source of ESP proteins in GAF and PAF, and that the iMf are coated with proteins secreted by the uterine epithelium. This interpretation is supported not only by the abundance of MSPs and vitellogenin in GAF and PAF ESP, but by the presence of omega-class secreted GST isoforms exclusively in GAF ESP, which in *O. volvulus* are only produced by embryos at the morula stage (49). Similarly, ESP proteins in the male nematode probably originate primarily from seminal fluid. Immune sera from rodents infected with *A. viteae* react most strongly with male and female gonad tissues, including the fluid channels between developing embryos and on sperm in both the spermatheca and seminal vesicle (117).

The role of the *Wolbachia* endosymbionts of filariae remains unclear: are they nutritional commensals, supporting the nematode through provision of energy or cofactors, or part of the immunological avoidance mechanisms of the parasite, or both (13)? It has been proposed that *Wolbachia* may be present in uterine fluid (118), inside degenerating embryos (119), or exit via the secretory pore (120). Additionally, they may secrete proteins into structures that lack bacterial cells, such as the cuticle (121). *Wolbachia*-derived proteins were present in very low amounts in *B. malayi* secreted products (17). We identified *Wolbachia* GroELS components in ESP of PAF and GAF, but not in other lifecycle stages. GroEL is the most abundant protein in *Wolbachia* (13, 15), and its detection in ESP may be through release of whole bacterial cells, for example in the female uterus from degenerating oocytes or embryos, or through secretion. GroEL, as a chaperonin, would be expected to be confined to the cytosol, although GroEL homologues have been reported to "moonlight" on the surface of some bacterial species (122). We also detected *Wolbachia* surface protein by surface labelling of adult *L. sigmodontis*, as has been reported in *B. malayi* (121). This protein is a putative ligand of Toll-like receptors 2 and 4 (119), and these findings support the hypothesis that *Wolbachia* modifies and perhaps misdirects the immune response to filariae (123). Whether *Wolbachia* GroEL also stimulates proinflammatory Toll-like receptors has not been evaluated, but a precedent exists in other bacteria (124), and antibodies against this protein are associated with pathology in LF (125).

The *L. sigmodontis* Secretome and Vaccine Development for Filariases

For several decades, vaccine development for human and veterinary filariases has focused on the L3 stage because irradiated L3 are highly efficacious at inducing protective immunity (23, 126) and strong anti-L3 immunity may block parasite establishment. *Litomosoides* is an excellent model for L3 vaccine research, as the L3 expresses a very similar repertoire of genes to the human and veterinary pathogens (127). Analyses of ESP from L3 of *L. sigmodontis* aid in defining a stereotypical secretomic profile for this stage. However, no defined parasite antigens (whether alone or in combination) have reproducibly attained an equivalent level of protection to irradiated L3 in any filarial system (7). Furthermore, since a single pair of adult nematodes can generate a patent infection, vaccines directed solely against L3 face a potentially insurmountable challenge.

Targeting of Mf has the potential to block transmission, and in the case of onchocerciasis, to reduce disease pathology. Moreover, the Mf stage has been shown to be more vulnerable to protective immune responses than L3 in several vaccination trials (128-130). Vaccination with a combination of ALT-1 and CPI-2 delivered as a DNA vaccine reduced circulating Mf levels by up to 90% in *L. sigmodontis*. Importantly, this protection was only achieved if immunomodulatory domains of the antigens were ablated (by mutation or deletion of the coding sequence) and was maintained even when the adult nematode burden was not significantly reduced. This phenomenon was probably to be due to the immunomodulatory effects of the native (active) proteins, as transplantation of a single adult female worm is sufficient to prevent clearance of injected Mf in naïve hosts (131). We suggest that it is likely that many of the other abundant molecules secreted by GAF may similarly have roles in facilitating Mf survival and could be targeted in an "anti-fecundity" vaccination strategy. Furthermore, the proteins identified by surface labelling of the GAF cuticle may also participate in generating a permissive environment (79, 80); thus, vaccination against these molecules, if sufficiently divergent from host homologues, might impede parasite establishment.

2.6 Conclusions

We have shown that *L. sigmodontis*, especially the GAF stage, releases a remarkable diversity of proteins into the external milieu and the majority of these molecules are uncharacterised. Although many of these proteins may be involved in fundamental aspects of embryogenesis, a subset are likely to be active immunomodulatory agents that protect the nematodes (and especially the circulating Mf) from the host immune response. The abundant ESP protein, CPI, may represent an archetype for this dual functionality, as it plays fundamental roles in oogenesis and fertilisation not only in parasitic nematodes but also in *C. elegans* (132). This suggests that its immunomodulatory properties are an example of secondary adaptation to a radically different environment. Thus, the pharmacopeia released by GAF may provide the ideal set of molecule(s) to target for immunoprophylaxis and chemotherapy of filariases; moreover, it could provide new compounds to tackle proinflammatory and autoimmune diseases (22)

TABLE 1

Proteins unique to the excretory-secretory products of individual lifecycle stages of *Litomosoides sigmodontis*

| Parasite stage ESp[a] | Locus tag | Annotation |
|---|---|---|
| PAF | nLs_02441 | Epicuticlin |
|  | nLs_07093 | Nucleoredoxin-like protein-2 |
|  | nLs_03968 | Nematode cuticle collagen N-terminal domain containing protein |
|  | nLs_06052 | Translationally controlled tumor protein |
|  | nLs_00526 | Glutathione reductase |
| AM | nLs_07249 | Glutaredoxin-like protein |
| vL3 | nLs_06400 | Activation-associated secreted protein-1 |
|  | nLs_09374 | Abundant larval transcript-1 protein |
|  | nLs_03087 | Cathepsin L-like precursor |
|  | nLs_06524 | Calmodulin |
| iMf | nLs_02254 | MSP domain-containing protein |

[a]Data for excretory-secretory products unique to gravid adult females are not shown due to the large number of proteins (195) in this category (see Table 3).
ESP, excretory-secretory products;
PAF, pre-gravid adult female;
AM, adult male;
vL3, vector-derived third-stage larvae;
iMf, immature microfilariae.

TABLE 2

Putative surface-associated proteins detected in biotin-labelled adult worm whole body extracts that were absent from unlabelled controls

| Parasite stage | Treatment | Peptides used for quantitation | Confidence score | Locus tag | Annotation | Presence in ESP |
|---|---|---|---|---|---|---|
| AM | OG | 7 | 857.06 | nLs_06907 | Adenylate kinase isoenzyme 1 | No |
|  | OG | 4 | 417.27 | nLs_09715 | Major sperm protein | Yes |
|  | OG | 2 | 186.68 | nLs_01742 | Filarial antigen Av33 | No |
|  | OG | 2 | 297.13 | nLs_08458 | Filarial antigen Ov16 | Yes |
|  | SDS | 2 | 308.12 | nLs_07359 | Calponin actin-binding domain containing protein | No |

TABLE 2-continued

Putative surface-associated proteins detected in biotin-labelled adult worm whole body extracts that were absent from unlabelled controls

| Parasite stage | Treatment | Peptides used for quantitation | Confidence score | Locus tag | Annotation | Presence in ESP |
|---|---|---|---|---|---|---|
| GAF | OG | 2 | 233.80 | nLs_09095 | Protein disulphide isomerase | No |
| | SDS | 2 | 86.22 | nLs_08755 | Leucine-rich repeat family protein | No |
| | SDS | 3 | 118.56 | nLs_09715 | Major sperm protein | Yes |
| | SDS | 2 | 99.43 | nLs_02353 | Complement component 1, q subcomponent-binding, mitochondrial-like | No |
| | SDS | 2 | 61.97 | nLs_01344 | Thioredoxin peroxidase 1 | No |
| | SDS | 2 | 108.87 | nLs_07321 | Vitellogenin | Yes |
| | PBS | 2 | 309.24 | nLs_00851 | DNA repair protein Rad4-containing protein | Yes |
| | PBS | 2 | 309.24 | nLs_07061 | Heat shock 70 kDa protein | Yes |
| | PBS | 2 | 309.24 | nLs_09360 | FMN-binding domain protein | No |
| | PBS | 3 | 463.79 | nLs_01364 | Transthyretin-like protein, partial | Yes |
| | PBS | 2 | 309.24 | nLs_03263 | Thioredoxin domain-containing protein | Yes |

ESP, excretory-secretory products; AM, adult male; OG, octyl β-D-glucopyranoside; GAF, gravid adult female; FMN, flavin mononucleotide.

TABLE 3

Protein predictions from the WLS genome

| | | Normalised iBAQ values | | | | |
|---|---|---|---|---|---|---|
| wLs acc | Description | GAF ESP | GAF WBE | PAF ES | PAF WBE | AM ESP |
| wLs_340 | co-chaperonin GroES | 0.001135899 | 0.006317778 | 0.004180529 | 0.008366027 | |
| wLs_2830 | molecular chaperone GroEL | 0.000349505 | 0.001423165 | 0.000279378 | 0.011718142 | |
| wLs_3910 | Outer surface protein Wsp | | 0.001218499 | | 0.005119482 | |
| wLs_4630 | hypothetical protein | | 0.000583035 | | 0.001471999 | |
| wLs_5240 | hypothetical protein Wbm0603 | | 0.000387749 | | 0.001641741 | |
| wLs_1920 | 50S ribosomal protein L7/L12 | | 0.000380102 | | | |
| wLs_9520 | thioredoxin | | 0.000169733 | | | |
| wLs_930 | Outer membrane protein, pal-like | | 0.000133493 | | 0.000208532 | |
| wLs_4010 | molecular chaperone OnaK | | 4.7978E−05 | | 0.000214183 | |
| wLs_1320 | hypothetical protein Wmb0010 | | 3.3069E−05 | | 0.000286269 | |
| wLs_5680 | isoprenoid biosynthesis protein with amidotransferase-like domain | | 9.91181E−06 | | 0.000233577 | |
| wLs_9680 | elongation factor Tu | | | | 0.000638185 | |
| wLs_8450 | hypethetical protein Wbm0655 | | | | 0.000190391 | |
| wLs_5270 | superoxide dismutase, SodA | | | | 0.000182807 | |
| wLs_1650 | nucloeoid DNA-binding protein | | | | 9.97899E−05 | |
| wLs_5000 | heat shock protein 90 | | | | 1.99158E−05 | |

| | | Normalised iBAQ values | | | | |
|---|---|---|---|---|---|---|
| | wLs acc | AM WBE | vL3 ESP | vL3 WBE | IMf ESP | IMF WBE |
| | wLs_340 | 0.000987231 | | 0.004898528 | | 0.007004044 |
| | wLs_2830 | 0.000305902 | | 0.001431935 | | 0.005708963 |

TABLE 3-continued

Protein predictions from the WLS genome

| | | | |
|---|---|---|---|
| wLs_3910 | 0.000169721 | 0.003337764 | 0.002241786 |
| wLs_4630 | 0.000104917 | | |
| wLs_5240 | 2.49886E−05 | 0.00097545 | 0.004069358 |
| wLs_1920 | | | |
| wLs_9520 | | | |
| wLs_930 | | 3.65115E−05 | 0.000291644 |
| wLs_4010 | | | 0.000236783 |
| wLs_1820 | 1.90627E−06 | 1.60884E−05 | 0.000626075 |
| wLs_5680 | | | |
| wLs_9680 | | | |
| wLs_8450 | | | |
| wLs_5270 | | | |
| wLs_1650 | | 0.00025721 | |
| wLs_5000 | | | |

TABLE 4

Homologues of abundant Litomosoides sigmodontis excretory-secretory proteins identified by DELTA-BLAST (National Centre for Biotechnology Information)

| Query | Filter[a] | Top annotated hit[b] [species] and accession | Max. score | Identity (%) | Query cover (%) | E-value |
|---|---|---|---|---|---|---|
| nLs_00113 | AT | PAN domain containing protein [Brugia malayi] XP_001900239.1 | 652 | 37 | 77 | 0.0 |
| | FE | Flagellin [Salmonella enterica] WP_023208887.1 | 134 | 15 | 12 | $2^{-28}$ |
| | CO | Protein SRAP-1, isoform a [C. elegans] NP_496398.3 | 114 | 26 | 56 | $3^{-24}$ |
| nLs_01398 | AT | Protein UNC-52, Isoform m [Caenorhabditis elegans] NP_001254444.1 | 1848 | 52 | 97 | 0.0 |
| nLs_02001 | AT | KH domain-containing protein [Loa loa] EFO27012.2 | 513 | 75 | 58 | $2^{-174}$ |
| | FE | Far upstream element-binding protein 1-like [Setaria italica] XP_004972470.1 | 97.4 | 18 | 65 | $5^{-18}$ |
| | CO | RNA helicase GLH-2 [C. elegans] AAB03337.1 | 72.0 | 25 | 33 | $2^{-12}$ |
| nLs_03577 | AT | Hypothetical protein Bm1_38495 [Brugia malayi] XP_001899152.1 | 128 | 60 | 100 | $2^{-32}$ |
| | FE | Heavy metal translocating P-type ATPase [Dorea sp. 5-2] WP_016217557.1 | 63.5 | 29 | 74 | $2^{-08}$ |
| | CO | Protein THOC-2 [C. elegans] NP_498392.2 | 42.0 | 27 | 55 | $1^{-03}$ |
| nLs_04059 | AT | Hypothetical protein LOAG_17826 [Loa loa] EJD74931.1 | 262 | 51 | 87 | $7^{-80}$ |
| | FE | A disintegrin and metalloproteinase with thrombospondin motifs 3-like [Aplysia californica] XP_005091919.1 | 52.0 | 29 | 68 | $7^{-04}$ |
| | CO | —[c] | — | — | — | — |
| nLs_05850 | AT | Hypothetical protein LOAG_04060 [Loa loa] XP_003139645.1 | 269 | 54 | 94 | $1^{-80}$ |
| | FE | Chondroitin proteoglycan 2 [Ascaris suum] EBRG86992.1 | 247 | 25 | 98 | $1^{-68}$ |
| | CO | CBR-CPG-2 protein [C. briggsae] XP_002633936.1 | 218 | 20 | 93 | $8^{-65}$ |
| nLs_08836 | AT | Apolipophorin [Ascaris suum] ERG86007.1 | 1535 | 42 | 99 | 0.0 |
| | FE | Zonadhesin-like [Saccoglossus kowolevskii] XP_002738323.1 | 256 | 19 | 44 | $4^{-65}$ |
| | CO | Protein VIT-4 [C. elegans] NP_508612.1 | 97.1 | 21 | 8 | $9^{-20}$ |
| nLs_01626 | AT | Animal heme peroxidase [Loa loa] XP_003141164.1 | 1367 | 84 | 98 | 0.0 |
| | FE | Peroxidasin-like protein [Ascaris suum] ERG87495.1 | 1308 | 72 | 98 | 0.0 |
| | CO | CBR-PXN-2 protein [C. briggsae] XP_002644069.1 | 1093 | 47 | 99 | 0.0 |

AT, all taxa; FE, Filarioidea excluded; CO, Caenorhabditis only.
[a]Filters were applied only where the top hit was to taxa othe than Caenorhabditis spp.
[b]Only annotated hits are shown for non-filarial proteins.
[c]The only hits were to hypothetical proteins containing ShK domains.

TABLE 5

Homologues of obondont Litomosoides sigmodontis excretory-secretory proteins identified by PSt-BLAST (Phyre$^2$)

| Query | Tap annotated hit [species] | UniRef50 ID | Bits | Normalised identity (%) | E-value |
|---|---|---|---|---|---|
| nLs_02001 | Transcription elongation factor SPT5 [Cryptococcus neoformans var. neoformans serotype D] | POCR70 | 135 | 14.9 | $3^{-30}$ |
| nLs_04059 | Sortilin-related receptor [Homo sapiens] | Q92673 | 210 | 10.0 | $1^{-52}$ |
| nLs_08836 | SCO-spondin [Dania rerio] | B3LF39 | 351 | 10.4 | $1^{-94}$ |

TABLE 6

Quantifiable proteins present in the excretory-secretory products of blood-derived microfilarie

| Accession\|Gene name | Peptides used for quantification | Confidence score | Description (species) | Normalised iBAQ |
|---|---|---|---|---|
| Q91X72\|HEMO_MOUSE | 7 | 898.19 | Hemopexin (*Mus musculus*) | $1.44^{-02}$ |
| Q8VCM7\|FIBG_MOUSE | 8 | 1040.62 | Fibrinogen γ chain (*Mus musculus*) | $1.15^{-01}$ |
| Q8KDE8\|FIBB_MOUSE | 9 | 1594.25 | Fibrinogen β chain (*Mus musculus*) | $9.56^{-02}$ |
| O35090\|ALBU_MERUN | 29 | 5013.66 | Serum albumin (*Meriones unguiculatus*) | $6.09^{-02}$ |
| P70274\|SEPP1_MOUSE | 3 | 203.64 | Selenoprotein P (*Mus musculus*) | $5.76^{-02}$ |
| Q61147\|CERU_MOUSE | 12 | 2215.19 | Ceruloplasmin (*Mus musculus*) | $5.56^{-02}$ |
| P29788\|VTNC_MOUSE | 6 | 1035.62 | Vitronectin (*Mus musculus*) | $5.43^{-02}$ |
| Q61702\|ITIH1_MOUSE | 7 | 1236.34 | Inter-α-trypsin inhibitor heavy chain H1 (*Mus musculus*) | $5.32^{-02}$ |
| P11276\|FINC_MOUSE | 49 | 8184.33 | Fibronectin (*Mus musculus*) | $3.80^{-02}$ |
| P01027\|CO3_MOUSE | 28 | 3368.39 | Complement C3 (*Mus musculus*) | $3.63^{-02}$ |
| P01942\|HBA_MOUSE | 2 | 149.76 | Hemoglobin subunit α (*Mus musculus*) | $3.60^{-02}$ |
| P97515\|PETUA_MERUN | 6 | 665.57 | α-2-HS-glycoprotein (*Meriones unguiculatus*) | $3.24^{-02}$ |
| P20918\|PLMN_MOUSE | 13 | 2062.8 | Plasminogen (*Mus musculus*) | $3.13^{-02}$ |
| P13020\|GELS_MOUSE | 5 | 1587.22 | Gelsolin (*Mus musculus*) | $2.83^{-02}$ |
| Q62577\|AMBP_MERUN | 6 | 1120.89 | Protein AMBP (*Meriones unguiculatus*) | $2.33^{-02}$ |
| P01029\|CO4B_MOUSE | 11 | 1814.14 | Complement C4-B (*Mus musculus*) | $1.52^{-02}$ |
| P05367\|SAA2_MOUSE | 4 | 820.91 | Serum amyloid A-2 protein (*Mus musculus*) | $1.34^{-02}$ |
| Q61703\|ITIH2_MOUSE | 7 | 1223.42 | Inter-α-trypsin inhibitor heavy chain H2 (*Mus musculus*) | $9.20^{-03}$ |
| nLs.2.1.2.t10069-RA | 4 | 264.21 | Transthyretin-like protein, partial (*Litomosoides sigmodontis*) | $9.11^{-03}$ |
| P04186\|CFAB_MOUSE | 6 | 361.74 | Complement factor B (*Mus musculus*) | $8.08^{-03}$ |
| P52430\|PON1_MOUSE | 2 | 166.19 | Serum paraoxonase/arylesterase 1 (*Mus musculus*) | $7.36^{-03}$ |
| Q02105\|C1QC_MOUSE | 2 | 292.88 | Complement C1q subcomponent subunit C (*Mus musculus*) | $6.31^{-03}$ |
| P06909\|CFAH_MOUSE | 2 | 156.16 | Complement factor H (*Mus musculus*) | $5.81^{-06}$ |
| P05017\|IGF1_MOUSE | 2 | 458.52 | Insulin-like growth factor I (*Mus musculus*) | $5.69^{-06}$ |
| P14106\|C1QB_MOUSE | 2 | 62.86 | Complement C1q subcomponent subunit B (*Mus musculus*) | $3.94^{-03}$ |
| A6X935\|ITIH4_MOUSE | 4 | 301.36 | Inter α-trypsin inhibitor, heavy chain 4 (*Mus musculus*) | $3.94^{-03}$ |
| E7D4P4\|E7D4P4_MERUN | 9 | 1172.7 | Apolipoprotein E (*Meriones unguiculatus*) | $3.78^{-03}$ |
| P97298\|PEDF_MOUSE | 5 | 420.63 | Pigment epithelium-derived factor (*Mus musculus*) | $3.31^{-03}$ |
| P47878\|IBP3_MOUSE | 5 | 520.36 | Insulin-like growth factor-binding protein 3 (*Mus musculus*) | $3.10^{-03}$ |
| P46412\|GPX3_MOUSE | 3 | 275.46 | Glutathione peroxidase 3 (*Mus musculus*) | $2.99^{-03}$ |
| Q8BH35\|CO88_MOUSE | 4 | 586.84 | Complement component C8 β chain (*Mus musculus*) | $2.99^{-03}$ |
| Q64118\|A1AT_MERUN | 3 | 183.98 | α-1-antitrypsin (*Meriones unguiculotus*) | $2.89^{-03}$ |
| Q06890\|CLUS_MOUSE | 5 | 427.41 | Clusterin (*Mus musculus*) | $1.91^{-03}$ |
| P70389\|ALS_MOUSE | 3 | 471.58 | Insulin-like growth factor-binding protein complex acid labile subunit (*Mus musculus*) | $1.88^{-03}$ |
| P35441\|TSP1_MOUSE | 8 | 853.9 | Thrombospondin-1 (*Mus musculus*) | $1.81^{-03}$ |
| P68033\|ACTC_MOUSE | 2 | 978.66 | Actin, α cardiac muscle 1 (*Mus musculus*) | $1.64^{-03}$ |
| Q00724\|RET4_MOUSE | 4 | 335.66 | Retinol-binding protein 4 (*Mus musculus*) | $1.63^{-03}$ |
| P26262\|KLKB1_MOUSE | 5 | 625.92 | Plasma kallikrein (*Mus musculus*) | $1.52^{-03}$ |
| Q61704\|ITIH3_MOUSE | 4 | 422.55 | Inter-α-trypsin inhibitor heavy chain H3 (*Mus-musculus*) | $1.52^{-03}$ |
| P19221\|THRB_MOUSE | 7 | 587.54 | Prothrombin (*Mus musculus*) | $1.45^{-03}$ |
| P33434\|MMP2_MOUSE | 3 | 283.7 | 72 kDa type IV collagenase (*Mus musculus*) | $1.42^{-03}$ |
| Q9JHH6\|CBPB2_MOUSE | 3 | 367.6 | Carboxypeptidase B2 (*Mus musculus*) | $1.38^{-03}$ |
| P32261\|ANT3_MOUSE | 2 | 306.33 | Antithrombin-III (*Mus musculus*) | $1.30^{-03}$ |
| nLs.2.1.2.t03443-RA | 3 | 366.35 | Hypothetical protein, Bm1_50630 homolog (*Litomosoides sigmodontis*) | $1.18^{-03}$ |
| nLs.2.1.2.t01366-RA | 2 | 269.78 | Transthyretin-like protein, partial (*Litomosoides sigmodontis*) | $9.56^{-04}$ |
| P11680\|PROP_MOUSE | 2 | 36.41 | Properdin (*Mus musculus*) | $9.27^{-04}$ |
| Q61646\|HPT_MOUSE | 3 | 236.91 | Haptoglobin (*Mus musculus*) | $8.65^{-04}$ |
| Q9JM99\|PRG4_MOUSE | 5 | 683.96 | Proteoglycan 4 (*Mus musculus*) | $8.57^{-04}$ |
| Q92111\|TRFE_MOUSE | 4 | 728.55 | Serotransferrin (*Mus musculus*) | $8.09^{-04}$ |
| P28798\|GRN_MOUSE | 2 | 300.7 | Granulins (*Mus musculus*) | $7.86^{-04}$ |
| P26928\|HGFL_MOUSE | 4 | 375.93 | Hepatocyte growth factor-like protein (*Mus musculus*) | $7.43^{-04}$ |
| Q9UN5\|CBPN_MOUSE | 3 | 219.53 | Carboxypeptidase N catalytic chain (*Mus musculus*) | $7.01^{-04}$ |
| P47879\|IBP4_MOUSE | 2 | 211.08 | Insulin-like growth factor-binding protein 4 (*Mus musculus*) | $6.96^{-04}$ |
| Q07968\|F136_MOUSE | 3 | 410.66 | Coagulation factor XIII B chain (*Mus musculus*) | $6.89^{-04}$ |
| Q9D6DD\|ICA_MOUSE | 6 | 787.37 | Inhibitor of carbonic anhydrase (*Mus musculus*) | $5.99^{-04}$ |
| P97290\|IC1_MOUSE | 4 | 387.11 | Plasma protease C1 inhibitor (*Mus musculus*) | $5.94^{-04}$ |
| Q8K182\|CO8A_MOUSE | 2 | 332.91 | Complement component C8 α chain (*Mus musculus*) | $5.78^{-04}$ |
| O70362\|PHLD_MOUSE | 2 | 100.55 | Phosphatidylinositol-glycan-specific phospholipase D (*Mus musculus*) | $4.92^{-04}$ |
| P01872\|IGHM_MOUSE | 2 | 174.92 | Ig μ chain C region secreted form (*Mus musculus*) | $4.48^{-04}$ |
| P06684\|CO5_MOUSE | 2 | 338.69 | Complement C5 (*Mus musculus*) | $4.07^{-04}$ |
| Q8K0D2\|HABP2_MOUSE | 2 | 60.74 | Hyaluronan-binding protein 2 (*Mus musculus*) | $3.53^{-04}$ |
| nLs.2.1.2.t01870-RA | 2 | 196.87 | ML domain-containing protein (*Litomosoides sigmodontis*) | $3.44^{-04}$ |
| nLs.2.1.2.t01365-RA | 2 | 188.68 | Transthyretin-like protein, partial (*Litomosoides sigmodontis*) | $2.74^{-04}$ |
| P28665\|MUG1_MOUSE | 3 | 312.94 | Murinoglobulin-1 (*Mus musculus*) | $2.05^{-04}$ |
| Q08879\|FBLN1_MOUSE | 2 | 305.64 | Fibulin-1 (*Mus musculus*) | $1.90^{-04}$ |
| Q8CG16\|C1RA_MOUSE | 2 | 102.86 | Complement C1r-A subcomponent (*Mus musculus*) | $1.04^{-04}$ |

IBAQ, intensity-based absolute quantification;
AMBP, α-1-microglobulin/bikunin precursor.

TABLE 7

Putative surface-associated proteins exhibiting >50-fold enrichment in biotin-labelled adult worm whole body extracts relative to unlabelled contols

| Parasite stage | Treatment | Peptides used for quantification | Confidence score | Fold-difference | Locus tag | Annotation | Presence in ESP |
|---|---|---|---|---|---|---|---|
| AM | SDS | 4 | 316.19 | 1,769.5 | nLs_09715 | Major sperm protein | Yes |
|  | SDS | 2 | 249.88 | 341.7 | nLs_01747 | Filarial antigen RAL-2 | Yes |
|  | SDS | 6 | 873.95 | 62.2 | nLs_06907 | Adenylate kinase isoenzyme 1 | No |
|  | PBS | 4 | 172.54 | 50.6 | nLs_09625 | Transthyretin-like protein 5 | Yes |
| GAF | Urea | 2 | 306.56 | 430.9 | nLs_02969 | Cysteine protease inhibitor-2 | Yes |
|  | Urea | 2 | 180.49 | 149.4 | nLs_08458 | Filarial antigen Ov16 | Yes |
|  | Urea | 2 | 302.26 | 65.2 | nLs_09625 | Transthyretin-like protein 5 | Yes |
|  | OG | 2 | 233.80 | 60,617.8 | nLs_09890 | Purine nucleoside phosphorylase | Yes |
|  | OG | 2 | 183.22 | 336.5 | nLs_00852 | Proliferating cell nucteur antigen domain protein | No |
|  | OG | 2 | 224.62 | 271.9 | nLs_04749 | 60S ribosomal protein L18 | No |
|  | OG | 2 | 191.67 | 168.3 | nLs_01364 | Transthyretin-lite protein, partial | Yes |
|  | OG | 3 | 194.25 | 156.3 | nLs_02023 | Tetratricopeptide-repeat domain protein | Yes |
|  | OG | 2 | 159.32 | 139.9 | nLs_02001 | KH domain-containing protein | Yes |
|  | OG | 2 | 188.56 | 118.1 | nLs_08084 | Type 1 inositol-trisphosphate 5-phosphatase | Yes |
|  | OG | 3 | 367.83 | 79.9 | nLs_02969 | Cysteine protease ihibitor-2 | Yes |
|  | OG | 3 | 367.26 | 66.6 | nLs_02463 | FKBP-type peptidyl-prolyl cis-trans isomerase | Yes |
|  | OG | 3 | 220.00 | 65.6 | nLs_00523 | KH domain centaining protein | Yes |
|  | OG | 3 | 376.34 | 59.0 | nLs_3910 | *Wolbachia* surface protein | No |
|  | OG | 2 | 258.28 | 52.2 | nLs_05241 | Tetratricopeptide-repeat domain protein | No |
|  | SDS | 2 | 50.67 | 1,059.7 | nLs_07759 | Cyclophlin Ovcyp-2 homologue | Yes |
|  | SDS | 6 | 306.80 | 328.9 | nLs_08458 | Filarial antigen Ov16 | Yes |
|  | SDS | 7 | 488.42 | 304.1 | nLs_01747 | Filarial antigen RAL-2 | Yes |
|  | SDS | 4 | 156.74 | 262.8 | nLs_05279 | HSP20/α-crystallin family protein | No |
|  | SDS | 2 | 144.16 | 242.7 | nLs_08696 | Lysozyme protein 8, partial | Yes |
|  | SDS | 2 | 87.95 | 235.6 | nLs_09890 | Purine nucleoside phosphorylase | Yes |
|  | SDS | 7 | 432.37 | 216.4 | nLs_09625 | Transthyretin-like protein 5 | Yes |
|  | SDS | 2 | 82.06 | 202.7 | nLs_2001 | KM domain-containing protein | Yes |
|  | SDS | 6 | 332.26 | 193.2 | nLs_08148 | Papilin | Yes |
|  | SDS | 2 | 122.31 | 162.4 | nLs_06907 | Adenylate kinase isoenzyme 1 | Yes |
|  | SDS | 2 | 44.96 | 162.1 | nLs_00117 | L-lactate dehydrogenase | Yes |
|  | SOS | 3 | 344.30 | 148.4 | nLs_05914 | Pyruvate dehydrogenase E1 component, α-subunit | Yes |
|  | SDS | 2 | 77.92 | 115.1 | nLs_09750 | Transthyretin-like protein 45 | Yes |
|  | SDS | 7 | 329.76 | 86.5 | nLs_03034 | p27 heat shock protein homologue | Yes |
|  | SDS | 5 | 166.70 | 82.3 | nLs_08836 | von Willebrand factor type-d domain protein | Yes |
|  | SDS | 3 | 138.70 | 71.7 | nLs_03328 | Myosin | No |
|  | SDS | 2 | 89.16 | 67.5 | nLs_01364 | Transthyretin-like protein, partial | Yes |
|  | SDS | 6 | 560.89 | 52.8 | nLs_08415 | Enolase | Yes |
|  | PBS | 5 | 631.96 | 111.4 | nLs_02378 | Aldo/keta reductase family protein | No |
|  | PBS | 2 | 309.24 | 104.0 | nLs_03070 | Atypical RIO/RIO2 protein kinase | Yes |
|  | PBS | 3 | 572.59 | 93.5 | nLs_00473 | Aldehyde dehydrogenase 11 | Yes |
|  | PBS | 6 | 1058.57 | 89.2 | nLs_06488 | Acid phosphatase | Yes |
|  | PBS | 9 | 1570.87 | 68.9 | nLs_01747 | Filarial antigen RAL-2 | Yes |
|  | PBS | 4 | 647.70 | 62.5 | nLs_03174 | Nematode secreted protein 22U | Yes |

ESP, ecretory-secretory products; AM, adult male; OG, octyl β-D glucopyranoside; GAF, gravid adult female; FKBP, FK506-binding protein; HSP, heat-shock protein.

REFERENCES

1. Mathers, C. D., Ezzati, M., and Lopez, A. D. (2007) Measuring the burden of neglected tropical diseases: the global burden of disease framework. *PLoS Negl. Trop. Dis.* 1, e114
2. Gardon, J., Gardon-Wendel, N., Demanga, N., Kamgno, J., Chippaux, J. P., and Boussinesq, M. (1997) Serious reactions after mass treatment of onchocerciasis with ivermectin in an area endemic for *Loa loa* infection. *Lancet* 350, 18-22
3. McCall, J. W., Genchi, C., Kramer, L. H., Guerrero, J., and Venco, L. (2008) Heartworm disease in animals and humans. *Adv. Parasitol.* 66, 193-285
4. Wahl, G., Achukwi, M. D., Mbah, D., Dawa, O., and Renz, A. (1994) Bovine onchocercosis in north Cameroon. *Vet. Parasitol.* 52, 297-311
5. Osei-Atweneboana, M. Y., Eng, J. K., Boakye, D. A., Gyapong, J. O., and Prichard, R. K. (2007) Prevalence and intensity of *Onchocerca volvulus* infection and efficacy of ivermectin in endemic communities in Ghana: a two-phase epidemiological study. *Lancet* 369, 2021-2029
6. Bourguinat, C., Keller, K., Bhan, A., Peregrine, A., Geary, T., and Prichard, R. (2011) Macrocyclic lactone resistance in *Dirofilaria immitis*. *Vet. Parasitol.* 181, 388-392
7. Morris, C. P., Evans, H., Larsen, S. E., and Mitre, E. (2013) A comprehensive, model-based review of vaccine and repeat infection trials for filariasis. *Clin. Microbiol. Rev.* 26, 381-421
8. Tamarozzi, F., Halliday, A., Gentil, K., Hoerauf, A., Pearlman, E., and Taylor, M. J. (2011) Onchocerciasis: the role of *Wolbachia* bacterial endosymbionts in parasite biology, disease pathogenesis, and treatment. *Clin. Microbiol. Rev.* 24, 459-468
9. Ghedin, E., Wang, S., Spiro, D., Caler, E., Zhao, Q., Crabtree, J., Allen, J. E., Delcher, A. L., Guiliano, D. B., Miranda-Saavedra, D., Angiuoli, S. V., Creasy, T., Amedeo, P., Haas, B., El-Sayed, N. M., Wortman, J. R., Feldblyum, T., Tallon, L., Schatz, M., Shumway, M., Koo, H., Salzberg, S. L., Schobel, S., Pertea, M., Pop, M., White, O., Barton, G. J., Carlow, C. K., Crawford, M. J., Daub, J., Dimmic, M. W., Estes, C. F., Foster, J. M., Ganatra, M., Gregory, W. F., Johnson, N. M., Jin, J., Komuniecki, R., Korf, I., Kumar, S., Laney, S., Li, B. W., Li, W., Lindblom, T. H., Lustigman, S., Ma, D., Maina, C. V., Martin, D. M., McCarter, J. P., McReynolds, L., Mitreva, M., Nutman, T. B., Parkinson, J., Peregrin-Alvarez, J. M., Poole, C., Ren, Q., Saunders, L., Sluder, A. E., Smith, K., Stanke, M., Unnasch, T. R., Ware, J., Wei, A. D., Weil, G., Williams, D. J., Zhang, Y., Williams, S. A., Fraser-Liggett, C., Slatko, B., Blaxter, M. L., and Scott, A. L. (2007) Draft genome of the filarial nematode parasite *Brugia malayi*. *Science* 317, 1756-1760

10. Godel, C., Kumar, S., Koutsovoulos, G., Ludin, P., Nilsson, D., Comandatore, F., Wrobel, N., Thompson, M., Schmid, C. D., Goto, S., Bringaud, F., Wolstenholme, A., Bandi, C., Epe, C., Kaminsky, R., Blaxter, M., and Maser, P. (2012) The genome of the heartworm, *Dirofilaria immitis*, reveals drug and vaccine targets. *FASEB J.* 26, 4650-4661

11. Desjardins, C. A., Cerqueira, G. C., Goldberg, J. M., Dunning Hotopp, J. C., Haas, B. J., Zucker, J., Ribeiro, J. M., Saif, S., Levin, J. Z., Fan, L., Zeng, Q., Russ, C., Wortman, J. R., Fink, D. L., Birren, B. W., and Nutman, T. B. (2013) Genomics of *Loa loa*, a *Wolbachia*-free filarial parasite of humans. *Nat. Genet.* 45, 495-500

12. Foster, J., Ganatra, M., Kamal, I., Ware, J., Makarova, K., Ivanova, N., Bhattacharyya, A., Kapatral, V., Kumar, S., Posfai, J., Vincze, T., Ingram, J., Moran, L., Lapidus, A., Omelchenko, M., Kyrpides, N., Ghedin, E., Wang, S., Goltsman, E., Joukov, V., Ostrovskaya, O., Tsukerman, K., Mazur, M., Comb, D., Koonin, E., and Slatko, B. (2005) The *Wolbachia* genome of *Brugia malayi*: endosymbiont evolution within a human pathogenic nematode. *PLoS Biol.* 3, e121

13. Darby, A. C., Armstrong, S. D., Bah, G. S., Kaur, G., Hughes, M. A., Kay, S. M., Koldkjaer, P., Rainbow, L., Radford, A. D., Blaxter, M. L., Tanya, V. N., Trees, A. J., Cordaux, R., Wastling, J. M., and Makepeace, B. L. (2012) Analysis of gene expression from the *Wolbachia* genome of a filarial nematode supports both metabolic and defensive roles within the symbiosis. *Genome Res.* 22, 2467-2477

14. Hewitson, J. P., Harcus, Y. M., Curwen, R. S., Dowle, A. A., Atmadja, A. K., Ashton, P. D., Wilson, A., and Maizels, R. M. (2008) The secretome of the filarial parasite, *Brugia malayi*: proteomic profile of adult excretory-secretory products. *Mol. Biochem. Parasitol.* 160, 8-21

15. Bennuru, S., Meng, Z., Ribeiro, J. M., Semnani, R. T., Ghedin, E., Chan, K., Lucas, D. A., Veenstra, T. D., and Nutman, T. B. (2011) Stage-specific proteomic expression patterns of the human filarial parasite *Brugia malayi* and its endosymbiont *Wolbachia*. *Proc. Natl. Acad. Sci. U.S.A* 108, 9649-9654

16. Moreno, Y., and Geary, T. G. (2008) Stage- and gender-specific proteomic analysis of *Brugia malayi* excretory-secretory products. *PLoS Negl. Trop. Dis.* 2, e326

17. Bennuru, S., Semnani, R., Meng, Z., Ribeiro, J. M., Veenstra, T. D., and Nutman, T. B. (2009) *Brugia malayi* excreted/secreted proteins at the host/parasite interface: stage- and gender-specific proteomic profiling. *PLoS Negl. Trop. Dis.* 3, e410

18. Petit, G., Diagne, M., Marechal, P., Owen, D., Taylor, D., and Bain, O. (1992) Maturation of the filaria *Litomosoides sigmodontis* in BALB/c mice; comparative susceptibility of nine other inbred strains. *Ann. Parasitol. Hum. Comp* 67, 144-150

19. Hoffmann, W., Petit, G., Schulz-Key, H., Taylor, D., Bain, O., and LeGoff, L. (2000) *Litomosoides sigmodontis* in mice: reappraisal of an old model for filarial research. *Parasitol. Today* 16, 387-389

20. Bain, O., Petit, G., and Diagne, M. (1989) [*Litomosoides*, parasites of rodents; taxonomic consequences]. *Ann. Parasitol. Hum. Comp* 64, 268-289

21. Pfaff, A. W., Schulz-Key, H., Soboslay, P. T., Taylor, D. W., MacLennan, K., and Hoffmann, W. H. (2002) *Litomosoides sigmodontis* cystatin acts as an immunomodulator during experimental filariasis. *Int. J. Parasitol.* 32, 171-178

22. Hubner, M. P., Shi, Y., Torrero, M. N., Mueller, E., Larson, D., Soloviova, K., Gondorf, F., Hoerauf, A., Killoran, K. E., Stocker, J. T., Davies, S. J., Tarbell, K. V., and Mitre, E. (2012) Helminth protection against autoimmune diabetes in nonobese diabetic mice is independent of a type 2 immune shift and requires TGF-beta. *J. Immunol.* 188, 559-568

23. LeGoff, L., Martin, C., Oswald, I. P., Vuong, P. N., Petit, G., Ungeheuer, M. N., and Bain, O. (2000) Parasitology and immunology of mice vaccinated with irradiated *Litomosoides sigmodontis* larvae. *Parasitology* 120 (Pt 3), 271-280

24. Babayan, S. A., Luo, H., Gray, N., Taylor, D. W., and Allen, J. E. (2012) Deletion of parasite immune modulatory sequences combined with immune activating signals enhances vaccine mediated protection against filarial nematodes. *PLoS Negl. Trop. Dis.* 6, e1968

25. Taylor, M. D., LeGoff, L., Harris, A., Malone, E., Allen, J. E., and Maizels, R. M. (2005) Removal of regulatory T cell activity reverses hyporesponsiveness and leads to filarial parasite clearance in vivo. *J. Immunol.* 174, 4924-4933

26. Darby, A. C., Christina, G. A., Armstrong, S. D., Hartley, C. S., Xia, D., Wastling, J. M., and Makepeace, B. L. (2013) Integrated transcriptomic and proteomic analysis of the global response of *Wolbachia* to doxycycline-induced stress. *ISME. J.* doi:10.1038/ismej.2013.192

27. Comandatore, F., Sassera, D., Montagna, M., Kumar, S., Koutsovoulos, G., Thomas, G., Repton, C., Babayan, S. A., Gray, N., Cordaux, R., Darby, A., Makepeace, B., and Blaxter, M. (2013) Phylogenomics and analysis of shared genes suggest a single transition to mutualism in *Wolbachia* of nematodes. *Genome Biol. Evol.* 5, 1668-1674

28. Schwanhausser, B., Busse, D., Li, N., Dittmar, G., Schuchhardt, J., Wolf, J., Chen, W., and Selbach, M. (2011) Global quantification of mammalian gene expression control. *Nature* 473, 337-342

29. Vizcaino, J. A., Cote, R. G., Csordas, A., Dianes, J. A., Fabregat, A., Foster, J. M., Griss, J., Alpi, E., Birim, M., Contell, J., O'Kelly, G., Schoenegger, A., Ovelleiro, D., Perez-Riverol, Y., Reisinger, F., Rios, D., Wang, R., and Hermjakob, H. (2013) The PRoteomics IDEntifications (PRIDE) database and associated tools: status in 2013. *Nucleic Acids Res.* 41, D1063-D1069

30. R Development Core Team. (2013) *R: A Language and Environment for Statistical Computing*, The R Foundation for Statistical Computing, Vienna, Austria 31. Benjamini, Y., and Hochberg, Y. (1995) Controlling the False Discovery Rate—A Practical and Powerful Approach to Multiple Testing. *Journal of the Royal Statistical Society Series B-Methodological* 57, 289-300

32. Kelley, L. A., and Sternberg, M. J. (2009) Protein structure prediction on the Web: a case study using the Phyre server. *Nat. Protoc.* 4, 363-371

33. Quevillon, E., Silventoinen, V., Pillai, S., Harte, N., Mulder, N., Apweiler, R., and Lopez, R. (2005) InterProScan: protein domains identifier. *Nucleic Acids Res.* 33, W116-W120
34. Martin, B., Chadwick, W., Yi, T., Park, S. S., Lu, D., Ni, B., Gadkaree, S., Farhang, K., Becker, K. G., and Maudsley, S. (2012) VENNTURE—a novel Venn diagram investigational tool for multiple pharmacological dataset analysis. *PLoS One* 7, e36911
35. Petersen, T. N., Brunak, S., von, H. G., and Nielsen, H. (2011) SignalP 4.0: discriminating signal peptides from transmembrane regions. *Nat. Methods* 8, 785-786
36. Bendtsen, J. D., Jensen, L. J., Blom, N., von, H. G., and Brunak, S. (2004) Feature-based prediction of non-classical and leaderless protein secretion. *Protein Eng Des Sel* 17, 349-356
37. Claros, M. G., and Vincens, P. (1996) Computational method to predict mitochondrially imported proteins and their targeting sequences. *Eur. J. Biochem.* 241, 779-786
38. Steentoft, C., Vakhrushev, S. Y., Joshi, H. J., Kong, Y., Vester-Christensen, M. B., Schjoldager, K. T., Lavrsen, K., Dabelsteen, S., Pedersen, N. B., Marcos-Silva, L., Gupta, R., Bennett, E. P., Mandel, U., Brunak, S., Wandall, H. H., Levery, S. B., and Clausen, H. (2013) Precision mapping of the human O-GalNAc glycoproteome through SimpleCell technology. *EMBO J.* 32, 1478-1488
39. Duckert, P., Brunak, S., and Blom, N. (2004) Prediction of proprotein convertase cleavage sites. *Protein Eng Des Sel* 17, 107-112
40. Jex, A. R., Liu, S., Li, B., Young, N. D., Hall, R. S., Li, Y., Yang, L., Zeng, N., Xu, X., Xiong, Z., Chen, F., Wu, X., Zhang, G., Fang, X., Kang, Y., Anderson, G. A., Harris, T. W., Campbell, B. E., Vlaminck, J., Wang, T., Cantacessi, C., Schwarz, E. M., Ranganathan, S., Geldhof, P., Nejsum, P., Sternberg, P. W., Yang, H., Wang, J., Wang, J., and Gasser, R. B. (2011) *Ascaris suum* draft genome. *Nature* 479, 529-533
41. Sievers, F., and Higgins, D. G. (2014) Clustal Omega, accurate alignment of very large numbers of sequences. *Methods Mol. Biol.* 1079, 105-116
42. Ronquist, F., Teslenko, M., van der Mark, P., Ayres, D. L., Darling, A., Hohna, S., Larget, B., Liu, L., Suchard, M. A., and Huelsenbeck, J. P. (2012) MrBayes 3.2: efficient Bayesian phylogenetic inference and model choice across a large model space. *Syst. Biol.* 61, 539-542
43. Crooks, G. E., Hon, G., Chandonia, J. M., and Brenner, S. E. (2004) WebLogo: a sequence logo generator. *Genome Res.* 14, 1188-1190
44. Gallin, M. Y., Tan, M., Kron, M. A., Rechnitzer, D., Greene, B. M., Newland, H. S., White, A. T., Taylor, H. R., and Unnasch, T. R. (1989) *Onchocerca volvulus* recombinant antigen: physical characterization and clinical correlates with serum reactivity. *J. Infect. Dis.* 160, 521-529
45. Dissanayake, S., Xu, M., and Piessens, W. F. (1992) A cloned antigen for serological diagnosis of *Wuchereria bancrofti* microfilaremia with daytime blood samples. *Mol. Biochem. Parasitol.* 56, 269-277
46. Hunter, S. J., Thompson, F. J., Tetley, L, and Devaney, E. (2001) Temperature is a cue for gene expression in the post-infective L3 of the parasitic nematode *Brugia pahangi*. *Mol. Biochem. Parasitol.* 112, 1-9
47. Gare, D., Boyd, J., and Connolly, B. (2004) Developmental regulation and secretion of nematode-specific cysteine-glycine domain proteins in *Trichinella spiralis*. *Mol. Biochem. Parasitol.* 134, 257-266
48. Lustigman, S., Brotman, B., Huima, T., Prince, A. M., and McKerrow, J. H. (1992) Molecular cloning and characterization of onchocystatin, a cysteine proteinase inhibitor of *Onchocerca volvulus*. *J. Biol. Chem.* 267, 17339-17346
49. Liebau, E., Hoppner, J., Muhlmeister, M., Burmeister, C., Luersen, K., Perbandt, M., Schmetz, C., Buttner, D., and Brattig, N. (2008) The secretory omega-class glutathione transferase OvGST3 from the human pathogenic parasite *Onchocerca volvulus*. *Febs Journal* 275, 3438-3453
50. Scott, A. L., Dinman, J., Sussman, D. J., and Ward, S. (1989) Major sperm protein and actin genes in free-living and parasitic nematodes. *Parasitology* 98 Pt 3, 471-478
51. Zahner, H., Hobom, G., and Stirm, S. (1995) The Microfilarial Sheath and Its Proteins. *Parasitology Today* 11, 116-120
52. Willenbucher, J., Hofle, W., and Lucius, R. (1993) The filarial antigens Av33/Ov33-3 show striking similarities to the major pepsin inhibitor from *Ascaris suum*. *Mol. Biochem. Parasitol.* 57, 349-351
53. Harnett, W., Houston, K. M., Tate, R., Garate, T., Apfel, H., Adam, R., Haslam, S. M., Panico, M., Paxton, T., Dell, A., Morris, H., and Brzeski, H. (1999) Molecular cloning and demonstration of an aminopeptidase activity in a filarial nematode glycoprotein. *Mol. Biochem. Parasitol.* 104, 11-23
54. Makinen, P. L., and Makinen, K. K. (1981) Purification and properties of rat skin acid phosphatases. *Int. J. Pept. Protein Res.* 18, 352-369
55. Fukushige, T., Goszczynski, B., Yan, J., and McGhee, J. D. (2005) Transcriptional control and patterning of the pho-1 gene, an essential acid phosphatase expressed in the *C. elegans* intestine. *Dev. Biol.* 279, 446-461
56. Ao, J. Q., Ling, E., Rao, X. J., and Yu, X. Q. (2008) A novel ML protein from Manduca sexta may function as a key accessory protein for lipopolysaccharide signaling. *Mol. Immunol.* 45, 2772-2781
57. Storch, J., and Xu, Z. (2009) Niemann-Pick C2 (NPC2) and intracellular cholesterol trafficking. *Biochim. Biophys. Acta* 1791, 671-678
58. Erttmann, K. D., and Gallin, M. Y. (1996) *Onchocerca volvulus*: identification of cDNAs encoding a putative phosphatidyl-ethanolamine-binding protein and a putative partially processed mRNA precursor. *Gene* 174, 203-207
59. Grant, R. P., Buttery, S. M., Ekman, G. C., Roberts, T. M., and Stewart, M. (2005) Structure of MFP2 and its function in enhancing MSP polymerization in *Ascaris* sperm amoeboid motility. *J. Mol. Biol.* 347, 583-595
60. Ou, X., Tang, L., McCrossan, M., Henkle-Dührsen, K., and Selkirk, M. E. (1995) *Brugia malayi*: localisation and differential expression of extracellular and cytoplasmic CuZn superoxide dismutases in adults and microfilariae. *Exp. Parasitol.* 80, 515-529
61. Ford, L., Guiliano, D. B., Oksov, Y., Debnath, A. K., Liu, J., Williams, S. A., Blaxter, M. L., and Lustigman, S. (2005) Characterization of a novel filarial serine protease inhibitor, Ov-SPI-1, from *Onchocerca volvulus*, with potential multifunctional roles during development of the parasite. *J. Biol. Chem.* 280, 40845-40856
62. Frank, G. R., Wisnewski, N., Brandt, K. S., Carter, C. R., Jennings, N. S., and Selkirk, M. E. (1999) Molecular cloning of the 22-24 kDa excretory-secretory 22U protein of *Dirofilaria immitis* and other filarial nematode parasites. *Mol. Biochem. Parasitol.* 98, 297-302

63. Gnanasekar, M., Padmavathi, B., and Ramaswamy, K. (2005) Cloning and characterization of a novel immunogenic protein 3 (NIP3) from *Brugia malayi* by immuno screening of a phage-display cDNA expression library. *Parasitol. Res.*
64. Chu, D. S., Liu, H., Nix, P., Wu, T. F., Ralston, E. J., Yates, J. R., III, and Meyer, B. J. (2006) Sperm chromatin proteomics identifies evolutionarily conserved fertility factors. *Nature* 443, 101-105
65. Joseph, G. T., Huima, T., Klion, A., and Lustigman, S. (2000) A novel developmentally regulated galectin of *Onchocerca volvulus*. *Mol. Biochem. Parasitol.* 106, 187-195
66. Garofalo, A., Klager, S. L., Rowlinson, M. C., Nirmalan, N., Klion, A., Allen, J. E., Kennedy, M. W., and Bradley, J. E. (2002) The FAR proteins of filarial nematodes: secretion, glycosylation and lipid binding characteristics. *Mol. Biochem. Parasitol.* 122, 161-170
67. Dafa'alla, T. H., Taubert, A., Hobom, G., Beck, E., and Zahner, H. (2000) Molecular characterization of a *Litomosoides sigmodontis* protein involved in the development of the microfilarial sheath during embryogenesis. *Mol. Biochem. Parasitol.* 106, 37-50
68. Rogalski, T. M., Mullen, G. P., Bush, J. A., Gilchrist, E. J., and Moerman, D. G. (2001) UNC-52/perlecan isoform diversity and function in *Caenorhabditis elegans*. *Biochem. Soc. Trans.* 29, 171-176
69. Olson, S. K., Bishop, J. R., Yates, J. R., Oegema, K., and Esko, J. D. (2006) Identification of novel chondroitin proteoglycans in *Caenorhabditis elegans*: embryonic cell division depends on CPG-1 and CPG-2. *J. Cell Biol.* 173, 985-994
70. Jones, M. R., Rose, A. M., and Baillie, D. L. (2012) Oligoarray comparative genomic hybridization-mediated mapping of suppressor mutations generated in a deletion-biased mutagenesis screen. *G3. (Bethesda.)* 2, 657-663
71. Murray, J., Gregory, W. F., Gomez-Escobar, N., Atmadja, A. K., and Maizels, R. M. (2001) Expression and immune recognition of *Brugia malayi* VAL-1, a homologue of vespid venom allergens and *Ancylostoma* secreted proteins. *Mol. Biochem. Parasitol.* 118, 89-96
72. Gregory, W. F., Blaxter, M. L., and Maizels, R. M. (1997) Differentially expressed, abundant trans-spliced cDNAs from larval *Brugia malayi*. *Mol. Biochem. Parasitol.* 87, 85-95
73. Guiliano, D. B., Hong, X., McKerrow, J. H., Blaxter, M. L., Oksov, Y., Liu, J., Ghedin, E., and Lustigman, S. (2004) A gene family of cathepsin L-like proteases of filarial nematodes are associated with larval molting and cuticle and eggshell remodeling. *Mol. Biochem. Parasitol.* 136, 227-242
74. Blaxter, M. (1998) *Caenorhabditis elegans* is a nematode. *Science* 282, 2041-2046
75. Beeton, C., Pennington, M. W., and Norton, R. S. (2011) Analogs of the sea anemone potassium channel blocker ShK for the treatment of autoimmune diseases. *Inflamm. Allergy Drug Targets.* 10, 313-321
76. Loukas, A., Hintz, M., Linder, D., Mullin, N. P., Parkinson, J., Tetteh, K. K., and Maizels, R. M. (2000) A family of secreted mucins from the parasitic nematode *Toxocara canis* bears diverse mucin domains but shares similar flanking six-cysteine repeat motifs. *J. Biol. Chem.* 275, 39600-39607
77. Yamaguchi, Y., Hasegawa, Y., Honma, T., Nagashima, Y., and Shiomi, K. (2010) Screening and cDNA cloning of Kv1 potassium channel toxins in sea anemones. *Mar. Drugs* 8, 2893-2905
78. Blaxter, M. L., and Robertson, W. M. (1998) The cuticle, In: Perry, R. N., and Wright, D. J. (eds), The physiology and biochemistry of free-living and plant-parasitic nematodes, pp. 25-48, CABI Publishing, Wallingford, Oxon.
79. Yegutkin, G. G. (2008) Nucleotide- and nucleoside-converting ectoenzymes: Important modulators of purinergic signalling cascade. *Biochim. Biophys. Acta* 1783, 673-694
80. Peerschke, E. I., and Ghebrehiwet, B. (2007) The contribution of gC1qR/p33 in infection and inflammation. *Immunobiology* 212, 333-342
81. Irvine, M., Huima, T., Prince, A. M., and Lustigman, S. (1994) Identification and characterization of an *Onchocerca volvulus* cDNA clone encoding a highly immunogenic calponin-like protein. *Mol. Biochem. Parasitol.* 65, 135-146
82. Wilson, W. R., Tuan, R. S., Shepley, K. J., Freedman, D. O., Greene, B. M., Awadzi, K., and Unnasch, T. R. (1994) The *Onchocerca volvulus* homologue of the multifunctional polypeptide protein disulfide isomerase. *Mol. Biochem. Parasitol.* 68, 103-117
83. Mancuso, V. P., Parry, J. M., Storer, L., Poggioli, C., Nguyen, K. C., Hall, D. H., and Sundaram, M. V. (2012) Extracellular leucine-rich repeat proteins are required to organize the apical extracellular matrix and maintain epithelial junction integrity in *C. elegans*. *Development* 139, 979-990
84. Lu, W., Egerton, G. L., Bianco, A. E., and Williams, S. A. (1998) Thioredoxin peroxidase from *Onchocerca volvulus*: a major hydrogen peroxide detoxifying enzyme in filarial parasites. *Mol. Biochem. Parasitol.* 91, 221-235
85. Babayan, S. A., Allen, J. E., and Taylor, D. W. (2012) Future prospects and challenges of vaccines against filariasis. *Parasite Immunol.* 34, 243-253
86. Sepsenwol, S., and Taft, S. J. (1990) In vitro induction of crawling in the amoeboid sperm of the nematode parasite, *Ascaris suum*. *Cell Motil. Cytoskeleton* 15, 99-110
87. Morgan, K. L., Estevez, A. O., Mueller, C. L., Cacho-Valadez, B., Miranda-Vizuete, A., Szewczyk, N. J., and Estevez, M. (2010) The glutaredoxin GLRX-21 functions to prevent selenium-induced oxidative stress in *Caenorhabditis elegans*. *Toxicol. Sci.* 118, 530-543
88. Hawkes, W. C., and Turek, P. J. (2001) Effects of dietary selenium on sperm motility in healthy men. *J. Androl* 22, 764-772
89. Zhao, Y., Sun, W., Zhang, P., Chi, H., Zhang, M. J., Song, C. Q., Ma, X., Shang, Y., Wang, B., Hu, Y., Hao, Z., Huhmer, A. F., Meng, F., L'hernault, S. W., He, S. M., Dong, M. Q., and Miao, L. (2012) Nematode sperm maturation triggered by protease involves sperm-secreted serine protease inhibitor (Serpin). *Proc. Natl. Acad. Sci. U.S.A* 109, 1542-1547
90. Johnson, M. H., Orihel, T. C., and Beaver, P. C. (1974) *Dipetalonema viteae* in the experimentally infected jird, *Meriones unguiculatus*. I. Insemination, development from egg to microfilaria, reinsemination, and longevity of mated and unmated worms. *J. Parasitol.* 60, 302-309
91. Funato, Y., and Miki, H. (2007) Nucleoredoxin, a novel thioredoxin family member involved in cell growth and differentiation. *Antioxid. Redox. Signal.* 9, 1035-1057
92. Kunchithapautham, K., Padmavathi, B., Narayanan, R. B., Kaliraj, P., and Scott, A. L. (2003) Thioredoxin from *Brugia malayi*: defining a 16-kilodalton class of thioredoxins from nematodes. *Infect. Immun.* 71, 4119-4126

93. Gems, D., and Riddle, D. L. (1996) Longevity in *Caenorhabditis elegans* reduced by mating but not gamete production. *Nature* 379, 723-725
94. Kumari, S., Lillibridge, C. D., Bakeer, M., Lowrie, R. C., Jr., Jayaraman, K., and Philipp, M. T. (1994) *Brugia malayi*: the diagnostic potential of recombinant excretory/secretory antigens. *Exp. Parasitol.* 79, 489-505
95. Bardehle, G., Hintz, M., Linder, D., Schares, G., Schott, H. H., Stirm, S., and Zahner, H. (1992) *Litomosoides carinii*: extraction of the microfilarial sheath components and antigenicity of the sheath fractions. *Parasitol. Res.* 78, 501-508
96. Maizels, R. M., Philipp, M., Dasgupta, A., and Partoni, F. (1984) Human serum albumin is a major component on the surface of microfilariae of *Wuchereria bancrofti*. *Parasite Immunol.* 6, 185-190
97. Shenoy, R. K., Rakesh, P. G., Baldwin, C. I., and Denham, D. A. (1996) The sheath of the microfilaria of *Brugia malayi* from human infections has IgG on its surface. *Parasitol. Res.* 82, 382-384
98. Bardehle, G., Jepp-Libutzki, A., Linder, D., Moehnle, K., Schott, H. H., Zahner, H., Zahringer, U., and Stirm, S. (1992) Chemical composition of *Litomosoides carinii* microfilarial sheaths. *Acta Trop.* 50, 237-247
99. Halliwell, B., and Gutteridge, J. M. (1990) The antioxidants of human extracellular fluids. *Arch. Biochem. Biophys.* 280, 1-8
100. Lal, R. B. (1991) Monoclonal antibodies to secreted antigens of *Brugia malayi* define a cross-reactive non-phosphocholine determinant on helminth parasites. *Immunol. Cell Biol.* 69 (Pt 2), 127-133
101. Olson, S. K., Greenan, G., Desai, A., Muller-Reichert, T., and Oegema, K. (2012) Hierarchical assembly of the eggshell and permeability barrier in *C. elegans*. *J. Cell Biol.* 198, 731-748
102. Johnston, W. L., Krizus, A., and Dennis, J. W. (2010) Eggshell chitin and chitin-interacting proteins prevent polyspermy in *C. elegans*. *Curr. Biol.* 20, 1932-1937
103. Schraermeyer, U., Peters, W., and Zahner, H. (1987) Lectin binding studies on adult filariae, intrauterine developing stages and microfilariae of *Brugia malayi* and *Litomosoides carinii*. *Parasitol. Res.* 73, 550-556
104. Jones, M. R., Rose, A. M., and Baillie, D. L. (2013) The ortholog of the human proto-oncogene ROS1 is required for epithelial development in *C. elegans*. *Genesis*. 51, 545-561
105. Gotenstein, J. R., Swale, R. E., Fukuda, T., Wu, Z., Giurumescu, C. A., Goncharov, A., Jin, Y., and Chisholm, A. D. (2010) The *C. elegans* peroxidasin PXN-2 is essential for embryonic morphogenesis and inhibits adult axon regeneration. *Development* 137, 3603-3613
106. Bi, M., Hickox, J. R., Winfrey, V. P., Olson, G. E., and Hardy, D. M. (2003) Processing, localization and binding activity of zonadhesin suggest a function in sperm adhesion to the zona pellucida during exocytosis of the acrosome. *Biochem. J.* 375, 477-488
107. Heiman, M. G., and Shaham, S. (2009) DEX-1 and DYF-7 establish sensory dendrite length by anchoring dendritic tips during cell migration. *Cell* 137, 344-355
108. Matyash, V., Geier, C., Henske, A., Mukherjee, S., Hirsh, D., Thiele, C., Grant, B., Maxfield, F. R., and Kurzchalia, T. V. (2001) Distribution and transport of cholesterol in *Caenorhabditis elegans*. *Mol. Biol. Cell* 12, 1725-1736
109. Moreno, Y., Gros, P. P., Tam, M., Segura, M., Valanparambil, R., Geary, T. G., and Stevenson, M. M. (2011) Proteomic analysis of excretory-secretory products of *Heligmosomoides polygyrus* assessed with next-generation sequencing transcriptomic information. *PLoS Negl. Trop. Dis.* 5, e1370
110. Nagaraj, S. H., Gasser, R. B., and Ranganathan, S. (2008) Needles in the EST haystack: large-scale identification and analysis of excretory-secretory (ES) proteins in parasitic nematodes using expressed sequence tags (ESTs). *PLoS Negl. Trop. Dis.* 2, e301
111. Kang, Y., Zhao, D., Liang, H., Liu, B., Zhang, Y., Liu, Q., Wang, X., and Liu, Y. (2012) Structural study of TTR-52 reveals the mechanism by which a bridging molecule mediates apoptotic cell engulfment. *Genes Dev.* 26, 1339-1350
112. Jacob, J., Vanholme, B., Haegeman, A., and Gheysen, G. (2007) Four transthyretin-like genes of the migratory plant-parasitic nematode *Radopholus similis*: members of an extensive nematode-specific family. *Gene* 402, 9-19
113. Saverwyns, H., Visser, A., Van, D. J., Power, D., Morgado, I., Kennedy, M. W., Knox, D. P., Schymkowitz, J., Rousseau, F., Gevaert, K., Vercruysse, J., Claerebout, E., and Geldhof, P. (2008) Analysis of the transthyretin-like (TTL) gene family in *Ostertagia ostertagi*—comparison with other strongylid nematodes and *Caenorhabditis elegans*. *Int. J. Parasitol.* 38, 1545-1556
114. Wergin, W. P., and Endo, B. Y. (1976) Ultrastructure of a neurosensory organ in a root-knot nematode. *J. Ultrastruct. Res.* 56, 258-276
115. Madathiparambil, M. G., Kaleysa, K. N., and Raghavan, K. (2009) A diagnostically useful 200-kDa protein is secreted through the surface pores of the filarial parasite *Setaria digitata*. *Parasitol. Res.* 105, 1099-1104
116. Kolotuev, I., Apaydin, A., and Labouesse, M. (2009) Secretion of Hedgehog-related peptides and WNT during *Caenorhabditis elegans* development. *Traffic*. 10, 803-810
117. Prusse, A., Vollmer, S., and Diesfeld, H. J. (1983) Immunocytochemical and ultrastructural studies on *Dipetalonema viteae* (Filarioidea). *J. Helminthol.* 57, 127-142
118. Kozek, W. J. (2005) What is new in the *Wolbachia/Dirofilaria* interaction? *Vet. Parasitol.* 133, 127-132
119. Brattig, N. W., Bazzocchi, C., Kirschning, C. J., Reiling, N., Buttner, D. W., Ceciliani, F., Geisinger, F., Hochrein, H., Ernst, M., Wagner, H., Bandi, C., and Hoerauf, A. (2004) The major surface protein of *Wolbachia* endosymbionts in filarial nematodes elicits immune responses through TLR2 and TLR4. *J. Immunol.* 173, 437-445
120. Landmann, F., Foster, J. M., Slatko, B., and Sullivan, W. (2010) Asymmetric *Wolbachia* segregation during early *Brugia malayi* embryogenesis determines its distribution in adult host tissues. *PLoS Negl. Trop. Dis.* 4, e758
121. Melnikow, E., Xu, S., Liu, J., Li, L., Oksov, Y., Ghedin, E., Unnasch, T. R., and Lustigman, S. (2011) Interaction of a *Wolbachia* WSP-like protein with a nuclear-encoded protein of *Brugia malayi*. *Int. J. Parasitol.* 41, 1053-1061
122. Henderson, B., and Martin, A. (2011) Bacterial virulence in the moonlight: multitasking bacterial moonlighting proteins are virulence determinants in infectious disease. *Infect. Immun.* 79, 3476-3491
123. Hansen, R. D., Trees, A. J., Bah, G. S., Hetzel, U., Martin, C., Bain, O., Tanya, V. N., and Makepeace, B. L. (2011) A worm's best friend: recruitment of neutrophils by *Wolbachia* confounds eosinophil degranulation against the filarial nematode *Onchocerca ochengi*. *Proc. Biol. Sci.* 278, 2293-2302
124. Argueta, J. G., Shiota, S., Yamaguchi, N., Masuhiro, Y., and Hanazawa, S. (2006) Induction of *Porphyromonas* gingivalis GroEL signaling via binding to Toll-like receptors 2 and 4. Oral Microbiol. Immunol. 21, 245-251
125. Suba, N., Shiny, C., Taylor, M. J., and Narayanan, R. B. (2007) Brugia malayi Wolbachia hsp60 IgG antibody and isotype reactivity in different clinical groups infected or exposed to human bancroftian lymphatic filariasis. Exp. Parasitol. 116, 291-295
126. Storey, D. M., and AI-Mukhtar, A. S. (1982) Vaccination of Jirds, Meriones unguiculatus, against Litomosoides carinii and Brugia pahangi using irradiate larvae of L. carinii. Tropenmed. Parasitol. 33, 23-24
127. Allen, J. E., Daub, J., Guiliano, D., McDonnell, A., Lizotte-Waniewski, M., Taylor, D. W., and Blaxter, M. (2000) Analysis of genes expressed at the infective larval stage validates utility of Litomosoides sigmodontis as a murine model for filarial vaccine development. Infect. Immun. 68, 5454-5458
128. Makepeace, B. L., Jensen, S. A., Laney, S. J., Nfon, C. K., Njongmeta, L. M., Tanya, V. N., Williams, S. A., Bianco, A. E., and Trees, A. J. (2009) Immunisation with a multivalent, subunit vaccine reduces patent infection in a natural bovine model of onchocerciasis during intense field exposure. PLoS Negl. Trop. Dis. 3, e544
129. Ziewer, S., Hubner, M. P., Dubben, B., Hoffmann, W. H., Bain, O., Martin, C., Hoerauf, A., and Specht, S. (2012) Immunization with L. sigmodontis microfilariae reduces peripheral microfilaraemia after challenge infection by inhibition of filarial embryogenesis. PLoS Negl. Trop. Dis. 6, e1558
130. Townson, S., and Bianco, A. E. (1982) Immunization of calves against the microfilariae of Onchocerca lienalis. J. Helminthol. 56, 297-303
131. Hoffmann, W. H., Pfaff, A. W., Schulz-Key, H., and Soboslay, P. T. (2001) Determinants for resistance and susceptibility to microfilaraemia in Litomosoides sigmodontis filariasis. Parasitology 122, 641-649
132. Hashmi, S., Zhang, J., Oksov, Y., Ji, Q., and Lustigman, S. (2006) The Caenorhabditis elegans CPI-2a cystatin-like inhibitor has an essential regulatory role during oogenesis and fertilization. J. Biol. Chem. 281, 28415-28429

Sequence Information and Comparisons

```
MSPFILLALLINAPANCRPDNGISRSRDASSA

CYDKDPDCSSDICKNYPYTAKERCPKFCGLC

SDTVSGSSARPSSQFLPSSSQRQSLALTSGAVE

KERKSLTS CTDKDSDCTAEICRNYPFTARERCAKTCGRC

SDDVAIGSGSTTAAHRSTAFGVEKFKGGSASSS

LSPRIGNALISGSL CFDRKFDCSREICRDFPFTARQ

ECAKTCGFC

SVDTSISSSSSNATLRVMSPSV

EIGGSSGGTSSHRTAKQDSYEANHNIPAYPRLS

RGEELE CVDVNIDCTQQTCKDYPFTARERCAKTCGFC

RKGSVVEERHSSLPAAQGNKATAITKE CKDEDSQC

SERSCLEHPYKASRKCAKTCGFC

GEKSSYGSVI

ELESPIAASSDEGSVIALDSDGNDGSSTRSTMTSE

RRLTSGSGDTMSMQKPKHSSIRGRTDPIRSSSSAS

TAHIQQPTNKQYLGTQRYPGRTGP CTDANQLCE

KADCYKYPNFSQKYCEKTCNYC
```

Above is domain organisation of the ShK domain-containing protein nLs_04059 from Litomosoides sigmodontis. Linear representation of the amino-acid sequence (SEQ ID NO: 1), showing the signal peptide (in italics), six ShK toxin-like domains (open rectangles) containing six cysteine residues each (highlighted), and a predicted propeptide cleavage site (underlined). Domain six at the C-terminus is unique in containing two lysyltyrosine dyads (bold).

```
Diro.  MGKYKGEIXCCGTGTSCKNICLKFSEFACNSCAKTCGILQSSGRSGVCYDKDPDCSDDVC
Lito.  ---------------MSPFILLALLINAPANCRPDNGISRSRDASSACYDKDPDCSSDIC
              .  * * :    *  .*    ** :*   *..********.*:*

Diro.  RNYPYTAKERCPKYCGLCHDSSLRSGNRLSSGLSSSYQQSSSSSLPSLKSGITGSTIIKK
Lito.  KNYPYTAKERCPKFCGLCSDTVSGSSARPSSQFLPSSSQRQSL---------ALTSGAVE
       :************:**** *:   *.  * ** :   * .* .*          :  ::    :

Diro.  DERKSSLPCIDKDSDCNMEICRNFPYTAKERCAKTCGLCSGETSSS-GIT--SGHHTIAG
Lito.  KERKSLTSCTDKDSDCTAEICRNYPFTARERCAKTCGRCSDDVAIGSGSTTAAHRSTAFG
       .****  * ******..*****:*:**:********.*   *:..  * * :   * *

Diro.  IDKSRGGT-TSLLSSARGNEPFSSGLCFDKKLDCRKEICRDFPPTAKEECAKTCGFCSSD
Lito.  VEKFKGGSASSSLSPRIGNALISGSLCFDRKFDCSREICRDFPPTARQECAKTCGFCSVD
       :.*  :**:  :* ** * **    :*..****:*:**  :*********.:********* *

Diro.  KGMSSSSSSGTAFGTMSPSRHAS--------IRINERDGITGIRSTSPHSILSKEKDLEC
Lito.  TSISSSSSNA-TLRVMSPSVEIGGSSGGTSSHRTAKQDSYEANHNIPAYPRLSRGEELEC
       ..:*****.. ::  .****  . .       *  ::*.  . :.    :   **: ::***

Diro.  TDLNTDCTQQICKDYPYTAKERCAKTCGFCRREMTEGDKTSVGGRHSSFTDKQRSRISEL
Lito.  VDVNIDCTQQTCKDYPFTARERCAKTCGFCRKGSVVEE------RHSSL-----------
       .*:* ***** *****:**:**********:   .  :       ****:

Diro.  DSRDSSLRGIKSSPTTEDCRDEDSQCSEKSCLDRPYTARTKCAKTCGFCGS------TVD
Lito.  ----PAAQGNKATAITKECKDEDSQCSERSCLEHPYKASRKCAKTCGFCGEKSSYGSVIE
           :  *  *::    *: *:*********:***** **:* .***********.       .::
```

```
                        -continued
Diro.  LEPPLVDSLDKGNIITLDDDVTT----RSTATFDRHSTSGIGTP--TQSSRHLSVGSRTD
Lito.  LESPIAASSDEGSVIALDSDGNDGSSTRSTMTSERRLTSGSGDTMSMQKPKHSSIRGRTD
       ** *:.. *  *:*:.:**.*        *** * :*: *** *     *. :* *: .***

Diro.  SSRK--PSLSTHIQQPTRRPFQGVLGRYPGRTGLCADENAYCQKEDCYKYPRFGQRYCEK
Lito.  PIRSSSSASTAHIQQPTNKQYLGT-QRYPGRTGPCTDANQLCEKADCYKYPNFSQKYCEK
        *.    : ::******.: : *.  ******* *:* *  *:* ******.*.*:****

Diro.  TCNYC
Lito.  TCNYC
```

Above is a sequence alignment comparison between ShK domain-containing proteins nLs.2.1.2.t04059-RA (from *Litomosoides sigmodontis*) of SEQ ID NO: 1 and nDi.2.2.2.t03402-RA (from *Dirofilaria immitis*) of SEQ ID NO: 2.

While overall identity between the two sequences is only 52.8%, it can be seen that the identity shared between the ShK domains (highlighted) of these two filarial nematode proteins is considerably higher.

The invention claimed is:

1. A polypeptide comprising:
   at least one ShK domain of *L. sigmoidontis* protein nLs_04059 according to SEQ ID NO:1; and/or
   at least one polypeptide sharing at least 70 percent identity with said at least one ShK domain, wherein the at least one polypeptide retains 6 cysteine residues with characteristic spacing of an ShK domain;
   wherein the polypeptide is artificial.

2. The polypeptide according to claim 1, wherein the polypeptide is a chimeric polypeptide.

3. The polypeptide according to claim 1, wherein the at least one polypeptide sharing at least 70 percent identity with said ShK domain is from a filarial nematode selected from group consisting of: *L. sigmodontis, D. immitis, Wuchereria bancrofti, Brugia malayi, Brugia timori, Onchocerca volvulus, Loa loa*.

4. A nucleic acid molecule, comprising:
   at least one nucleic acid sequence encoding at least one polypeptide comprising at least one ShK domain of *L. sigmoidontis* protein nLs_04059 according to SEQ ID NO:1; and/or
   at least one nucleic acid encoding at least one polypeptide sharing at least 70 percent identity with said at least one Shk domain wherein the at least one polypeptide retains 6 cysteine residues with characteristic spacing of an ShK domain;
   wherein the nucleic acid molecule is artificial.

5. An expression vector comprising the nucleic acid molecule according to claim 4, optionally wherein said expression vector is for expression in *E. coli*.

6. The nucleic acid according to claim 4, wherein the at least one polypeptide sharing at least 70 percent identity with said at least one ShK domain is from a filarial nematode selected from group consisting of: *L. sigmodontis, D. immitis, Wuchereria bancrofti, Brugia malayi, Brugia timori, Onchocerca volvulus, Loa loa*.

7. A method of treating or preventing a filarial nematode infection, comprising the steps of:
   providing to a subject a therapeutically effective amount of at least one polypeptide comprising at least one ShK domain of *L. sigmoidontis* protein nLs_04059 according to SEQ ID NO:1 and/or at least one polypeptide sharing at least 70 percent identity with at least one Shk domain wherein the at least one polypeptide retains 6 cysteine residues with characteristic spacing of an ShK domain.

8. The method according to claim 7, wherein the subject is a human or an animal.

9. The method according to claim 7, wherein the filarial nematode infection includes a disease selected from the group consisting of: lymphatic filariasis, onchocerciasis, and loiasis.

10. The method according to claim 7, wherein the subject is an animal and the filarial nematode infection is heartworm.

11. The method according to claim 7, wherein the at least one polypeptide sharing at least 70 percent identity with at least one Shk domain of a filarial nematode protein is from a filarial nematode selected from a group consisting of: *L. sigmodontis, D. immitis, Wuchereria bancrofti, Brugia malayi, Brugia timori, Onchocerca volvulus*, and *Loa loa*.

12. The method according to claim 7, wherein the at least one ShK domain and/or the at least one polypeptide sharing at least 70 percent identity with said at least one Shk domain is formulated as a pharmaceutical composition.

13. The method according to claim 10, further comprising the step of:
   administering a nucleic acid molecule encoding the therapeutically effective amount of the at least one polypeptide.

14. The method according to claim 10, wherein the at least one polypeptide comprises a plurality of the same or different ShK domains.

15. The method according to claim 10, wherein the at least one polypeptide is a chimeric polypeptide, optionally wherein the at least one polypeptide further comprises an artificial spacer separating the ShK domains.

16. The method according to claim 10, wherein the at least one polypeptide further comprises an additional vaccine antigen.

* * * * *

```
                        SEQUENCE LISTING

<160> NUMBER OF SEQ ID NOS: 14

<210> SEQ ID NO 1
<211> LENGTH: 498
<212> TYPE: PRT
<213> ORGANISM: Litomosoides sigmodontis

<400> SEQUENCE: 1

Met Ser Pro Phe Ile Leu Leu Ala Leu Leu Ile Asn Ala Pro Ala Asn
1               5                   10                  15

Cys Arg Pro Asp Asn Gly Ile Ser Arg Ser Arg Asp Ala Ser Ser Ala
            20                  25                  30

Cys Tyr Asp Lys Asp Pro Asp Cys Ser Ser Asp Ile Cys Lys Asn Tyr
        35                  40                  45

Pro Tyr Thr Ala Lys Glu Arg Cys Pro Lys Phe Cys Gly Leu Cys Ser
    50                  55                  60

Asp Thr Val Ser Gly Ser Ser Ala Arg Pro Ser Ser Gln Phe Leu Pro
65                  70                  75                  80

Ser Ser Ser Gln Arg Gln Ser Leu Ala Leu Thr Ser Gly Ala Val Glu
                85                  90                  95

Lys Glu Arg Lys Ser Leu Thr Ser Cys Thr Asp Lys Asp Ser Asp Cys
            100                 105                 110

Thr Ala Glu Ile Cys Arg Asn Tyr Pro Phe Thr Ala Arg Glu Arg Cys
        115                 120                 125

Ala Lys Thr Cys Gly Arg Cys Ser Asp Asp Val Ala Ile Gly Ser Gly
    130                 135                 140

Ser Thr Thr Ala Ala His Arg Ser Thr Ala Phe Gly Val Glu Lys Phe
145                 150                 155                 160

Lys Gly Gly Ser Ala Ser Ser Ser Leu Ser Pro Arg Ile Gly Asn Ala
                165                 170                 175

Leu Ile Ser Gly Ser Leu Cys Phe Asp Arg Lys Phe Asp Cys Ser Arg
            180                 185                 190

Glu Ile Cys Arg Asp Phe Pro Phe Thr Ala Arg Gln Glu Cys Ala Lys
        195                 200                 205

Thr Cys Gly Phe Cys Ser Val Asp Thr Ser Ile Ser Ser Ser Ser Ser
    210                 215                 220

Asn Ala Thr Leu Arg Val Met Ser Pro Ser Val Glu Ile Gly Gly Ser
225                 230                 235                 240

Ser Gly Gly Thr Ser Ser His Arg Thr Ala Lys Gln Asp Ser Tyr Glu
                245                 250                 255

Ala Asn His Asn Ile Pro Ala Tyr Pro Arg Leu Ser Arg Gly Glu Glu
```

```
                260               265               270
Leu Glu Cys Val Asp Val Asn Ile Asp Cys Thr Gln Gln Thr Cys Lys
                275               280               285

Asp Tyr Pro Phe Thr Ala Arg Glu Arg Cys Ala Lys Thr Cys Gly Phe
                290               295               300

Cys Arg Lys Gly Ser Val Val Glu Glu Arg His Ser Ser Leu Pro Ala
305               310               315               320

Ala Gln Gly Asn Lys Ala Thr Ala Ile Thr Lys Glu Cys Lys Asp Glu
                325               330               335

Asp Ser Gln Cys Ser Glu Arg Ser Cys Leu Glu His Pro Tyr Lys Ala
                340               345               350

Ser Arg Lys Cys Ala Lys Thr Cys Gly Phe Cys Gly Glu Lys Ser Ser
                355               360               365

Tyr Gly Ser Val Ile Glu Leu Glu Ser Pro Ile Ala Ala Ser Ser Asp
                370               375               380

Glu Gly Ser Val Ile Ala Leu Asp Ser Asp Gly Asn Asp Gly Ser Ser
385               390               395               400

Thr Arg Ser Thr Met Thr Ser Glu Arg Arg Leu Thr Ser Gly Ser Gly
                405               410               415

Asp Thr Met Ser Met Gln Lys Pro Lys His Ser Ser Ile Arg Gly Arg
                420               425               430

Thr Asp Pro Ile Arg Ser Ser Ser Ala Ser Thr Ala His Ile Gln
                435               440               445

Gln Pro Thr Asn Lys Gln Tyr Leu Gly Thr Gln Arg Tyr Pro Gly Arg
                450               455               460

Thr Gly Pro Cys Thr Asp Ala Asn Gln Leu Cys Glu Lys Ala Asp Cys
465               470               475               480

Tyr Lys Tyr Pro Asn Phe Ser Gln Lys Tyr Cys Glu Lys Thr Cys Asn
                485               490               495

Tyr Cys

<210> SEQ ID NO 2
<211> LENGTH: 519
<212> TYPE: PRT
<213> ORGANISM: Dirofilaria immitis
<220> FEATURE:
<221> NAME/KEY: MISC_FEATURE
<222> LOCATION: (9)..(9)
<223> OTHER INFORMATION: Xaa can be any naturally occurring amino acid

<400> SEQUENCE: 2

Met Gly Lys Tyr Lys Gly Glu Ile Xaa Cys Cys Gly Thr Gly Thr Ser
1               5                  10                15

Cys Lys Asn Ile Cys Leu Lys Phe Ser Glu Phe Ala Cys Asn Ser Cys
                20                 25                30

Ala Lys Thr Cys Gly Ile Leu Gln Ser Gly Arg Ser Gly Val Cys
                35                 40                45

Tyr Asp Lys Asp Pro Asp Cys Ser Asp Val Cys Arg Asn Tyr Pro
        50                 55                 60

Tyr Thr Ala Lys Glu Arg Cys Pro Lys Tyr Cys Gly Leu Cys His Asp
65                 70                 75                80

Ser Ser Leu Arg Ser Gly Asn Arg Leu Ser Ser Gly Leu Ser Ser Ser
                85                 90                95

Tyr Gln Gln Ser Ser Ser Ser Ser Leu Pro Ser Leu Lys Ser Gly Ile
                100                105               110
```

-continued

```
Thr Gly Ser Thr Ile Ile Lys Lys Asp Glu Arg Lys Ser Ser Leu Pro
            115                 120                 125
Cys Ile Asp Lys Asp Ser Asp Cys Asn Met Glu Ile Cys Arg Asn Phe
130                 135                 140
Pro Tyr Thr Ala Lys Glu Arg Cys Ala Lys Thr Cys Gly Leu Cys Ser
145                 150                 155                 160
Gly Glu Thr Ser Ser Ser Gly Ile Thr Ser Gly His His Thr Ile Ala
                165                 170                 175
Gly Ile Asp Lys Ser Arg Gly Gly Thr Thr Ser Leu Leu Ser Ser Arg
            180                 185                 190
Arg Gly Asn Glu Pro Phe Ser Ser Gly Leu Cys Phe Asp Lys Lys Leu
            195                 200                 205
Asp Cys Arg Lys Glu Ile Cys Arg Asp Phe Pro Phe Thr Ala Lys Glu
210                 215                 220
Glu Cys Ala Lys Thr Cys Gly Phe Cys Ser Ser Asp Lys Gly Met Ser
225                 230                 235                 240
Ser Ser Ser Ser Gly Thr Ala Phe Gly Thr Met Ser Pro Ser Arg
                245                 250                 255
His Ala Ser Ile Arg Ile Asn Glu Arg Asp Gly Ile Thr Gly Ile Arg
            260                 265                 270
Ser Thr Ser Pro His Ser Ile Leu Ser Lys Glu Lys Asp Leu Glu Cys
            275                 280                 285
Thr Asp Leu Asn Thr Asp Cys Thr Gln Gln Ile Cys Lys Asp Tyr Pro
            290                 295                 300
Tyr Thr Ala Lys Glu Arg Cys Ala Lys Thr Cys Gly Phe Cys Arg Arg
305                 310                 315                 320
Glu Met Thr Glu Gly Asp Lys Thr Ser Val Gly Gly Arg His Ser Ser
                325                 330                 335
Phe Thr Asp Lys Gln Arg Ser Arg Ile Ser Glu Leu Asp Ser Arg Asp
            340                 345                 350
Ser Ser Leu Arg Gly Ile Lys Ser Ser Pro Thr Thr Glu Asp Cys Arg
            355                 360                 365
Asp Glu Asp Ser Gln Cys Ser Glu Lys Ser Cys Leu Asp Arg Pro Tyr
            370                 375                 380
Thr Ala Arg Thr Lys Cys Ala Lys Thr Cys Gly Phe Cys Gly Ser Thr
385                 390                 395                 400
Val Asp Leu Glu Pro Pro Leu Val Asp Ser Leu Asp Lys Gly Asn Ile
                405                 410                 415
Ile Thr Leu Asp Asp Val Thr Thr Arg Ser Thr Ala Thr Phe Asp
            420                 425                 430
Arg His Ser Thr Ser Gly Ile Gly Thr Pro Thr Gln Ser Ser Arg His
            435                 440                 445
Leu Ser Val Gly Ser Arg Thr Asp Ser Ser Arg Lys Pro Ser Leu Ser
            450                 455                 460
Thr His Ile Gln Gln Pro Thr Arg Arg Pro Phe Gln Gly Val Leu Gly
465                 470                 475                 480
Arg Tyr Pro Gly Arg Thr Gly Leu Cys Ala Asp Glu Asn Ala Tyr Cys
                485                 490                 495
Gln Lys Glu Asp Cys Tyr Lys Tyr Pro Arg Phe Gly Asn Arg Tyr Cys
            500                 505                 510
Glu Lys Thr Cys Asn Tyr Cys
            515
```

<210> SEQ ID NO 3
<211> LENGTH: 237
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (164)..(164)
<223> OTHER INFORMATION: Xaa can be any naturally occurring amino acid
<220> FEATURE:
<221> NAME/KEY: MISC_FEATURE
<222> LOCATION: (175)..(175)
<223> OTHER INFORMATION: Xaa can be any naturally occurring amino acid
<220> FEATURE:
<221> NAME/KEY: MISC_FEATURE
<222> LOCATION: (208)..(208)
<223> OTHER INFORMATION: Xaa can be any naturally occurring amino acid
<220> FEATURE:
<221> NAME/KEY: MISC_FEATURE
<222> LOCATION: (212)..(212)
<223> OTHER INFORMATION: Xaa can be any naturally occurring amino acid
<220> FEATURE:
<221> NAME/KEY: MISC_FEATURE
<222> LOCATION: (223)..(223)
<223> OTHER INFORMATION: Xaa can be any naturally occurring amino acid

<400> SEQUENCE: 3

Met Thr Thr Gln Arg Leu Gln Met Val Phe Ile Val Ala Val Val Leu
1               5                   10                  15

Thr Cys Leu Ala Leu Asn Asp Ile Gln Ala Met Arg Ile Lys Arg Asp
            20                  25                  30

Asp Ala Gly Gln Glu Asp His Lys Asn Gln Thr Asp Val Asn His Asp
        35                  40                  45

Glu His Gln Glu His Gly Glu His Gln Asn Asp Ser Ser His Glu
    50                  55                  60

Lys His Glu His His Asn Cys Ser Gly Ser His Glu Ser His Ser Lys
65                  70                  75                  80

Glu His His Asp Glu Asp His His Glu Lys Lys Met His Tyr Tyr
                85                  90                  95

Cys Lys Cys Arg His His His Asp Asn Asp Thr Glu Ser His Glu His
            100                 105                 110

Glu His Glu His Ala His Glu Asn Asp Thr Glu Thr His Gly Asp Tyr
        115                 120                 125

His His Lys Gly Ile His Glu His Leu Gly Asn His Ser Asp Ser Ser
    130                 135                 140

Glu Tyr Asn His Glx Glu Cys Arg Cys His Cys His Cys Pro Lys His
145                 150                 155                 160

Lys Gly Ser Xaa Asn Gln Glu Gln Glu Arg Lys Lys His Lys Xaa Lys
                165                 170                 175

Gly Ser Gly Glu His Cys His Cys Phe Cys His His Gly Asp Glu
            180                 185                 190

Glu His Lys Gly Ser Asp Gln Lys Glu Arg His Asp Lys Glu His Xaa
        195                 200                 205

Asp Lys Glu Xaa Glu His Lys Lys Glu Ser Glu Glu Lys Glu Xaa Lys
    210                 215                 220

Glu Glu Lys Asn Gln Asp Gln Val Met Lys Leu Leu Phe
225                 230                 235

<210> SEQ ID NO 4
<211> LENGTH: 234
<212> TYPE: PRT
<213> ORGANISM: Unknown

```
<220> FEATURE:
<223> OTHER INFORMATION: Setaria labiatopopillosa

<400> SEQUENCE: 4
```

| | | | | | | | | | | | | | | |
|---|---|---|---|---|---|---|---|---|---|---|---|---|---|---|
| Met | Met | Asn | Gln | Lys | Leu | His | Val | Val | Phe | Ile | Val | Thr | Met | Val | Leu |
| 1 | | | | 5 | | | | | 10 | | | | | 15 | |

| Thr | Cys | Leu | Thr | Leu | Asn | Glu | Ile | Gln | Ala | Met | Arg | Ile | Lys | Arg | Asn |
|---|---|---|---|---|---|---|---|---|---|---|---|---|---|---|---|
| | | | 20 | | | | | 25 | | | | | 30 | | |

| Asp | Ala | Arg | Pro | Glu | Asp | Leu | Lys | Asn | Gln | Thr | Glu | Leu | Ile | Gln | Asp |
|---|---|---|---|---|---|---|---|---|---|---|---|---|---|---|---|
| | | 35 | | | | | 40 | | | | | 45 | | | |

| Gln | His | Gln | Glu | Arg | Gln | Asn | Asp | Ser | Ser | His | Glu | Arg | His | Glu | His |
|---|---|---|---|---|---|---|---|---|---|---|---|---|---|---|---|
| | 50 | | | | | 55 | | | | | 60 | | | | |

| His | Ser | Asn | Cys | Ser | Gly | Asn | His | Glu | Ile | His | Asn | Lys | Glu | His | Ser |
|---|---|---|---|---|---|---|---|---|---|---|---|---|---|---|---|
| 65 | | | | | 70 | | | | | 75 | | | | | 80 |

| Asp | Glu | Glu | Arg | His | His | Gly | Lys | Lys | Val | His | Tyr | Tyr | Cys | Lys | Cys |
|---|---|---|---|---|---|---|---|---|---|---|---|---|---|---|---|
| | | | | 85 | | | | | 90 | | | | | 95 | |

| His | Arg | His | His | Asp | Asn | Asp | Thr | Asp | Ser | His | Glu | His | His | Val | His |
|---|---|---|---|---|---|---|---|---|---|---|---|---|---|---|---|
| | | | 100 | | | | | 105 | | | | | 110 | | |

| Glu | Asn | Asp | Thr | Glu | Ala | Asp | Gly | Asp | Asn | Tyr | His | His | His | Phe | Asp |
|---|---|---|---|---|---|---|---|---|---|---|---|---|---|---|---|
| | | 115 | | | | | 120 | | | | | 125 | | | |

| His | Lys | Val | Val | Gln | Glu | Tyr | Gln | Cys | Asn | His | Ser | Asp | Ile | Ser | Glu |
|---|---|---|---|---|---|---|---|---|---|---|---|---|---|---|---|
| | 130 | | | | | 135 | | | | | 140 | | | | |

| His | Asp | Arg | Asn | Glu | Cys | His | Cys | His | Cys | His | Cys | Pro | Lys | His | Glu |
|---|---|---|---|---|---|---|---|---|---|---|---|---|---|---|---|
| 145 | | | | | 150 | | | | | 155 | | | | | 160 |

| Arg | Asn | Asn | Gln | Arg | Lys | Glu | Arg | Lys | Lys | Asn | Lys | His | His | Glu | Thr |
|---|---|---|---|---|---|---|---|---|---|---|---|---|---|---|---|
| | | | | 165 | | | | | 170 | | | | | 175 | |

| Asn | Glu | His | Cys | His | Cys | Phe | Cys | His | Ser | His | Gly | Asn | Glu | Glu | Ile |
|---|---|---|---|---|---|---|---|---|---|---|---|---|---|---|---|
| | | | 180 | | | | | 185 | | | | | 190 | | |

| Lys | Gly | Ser | Ser | Gln | Lys | Glu | His | His | Asp | Ser | Asp | Lys | Glu | Gln | Ser |
|---|---|---|---|---|---|---|---|---|---|---|---|---|---|---|---|
| | | 195 | | | | | 200 | | | | | 205 | | | |

| Lys | Glu | Asn | Lys | Lys | Glu | Ser | Glu | Glu | Lys | Glu | Gln | Gly | Glu | Glu | Lys |
|---|---|---|---|---|---|---|---|---|---|---|---|---|---|---|---|
| | 210 | | | | | 215 | | | | | 220 | | | | |

| His | Gln | Asp | Gln | Val | Met | Lys | Leu | Leu | Phe |
|---|---|---|---|---|---|---|---|---|---|
| 225 | | | | 230 | | | | | |

```
<210> SEQ ID NO 5
<211> LENGTH: 240
<212> TYPE: PRT
<213> ORGANISM: Litomosoides sigmodontis

<400> SEQUENCE: 5
```

| Met | Thr | Thr | Gln | Arg | Leu | Pro | Met | Ala | Phe | Ile | Val | Thr | Val | Val |
|---|---|---|---|---|---|---|---|---|---|---|---|---|---|---|
| 1 | | | | 5 | | | | | 10 | | | | | 15 |

| Thr | Cys | Leu | Val | Leu | Asn | Asp | Ile | Gln | Ala | Met | Arg | Ile | Lys | Arg | Asp |
|---|---|---|---|---|---|---|---|---|---|---|---|---|---|---|---|
| | | | 20 | | | | | 25 | | | | | 30 | | |

| Asp | Ala | Gly | Asn | Glu | Asp | Gln | Thr | Asn | Gly | Thr | Asp | Val | Asn | Arg | Asp |
|---|---|---|---|---|---|---|---|---|---|---|---|---|---|---|---|
| | | 35 | | | | | 40 | | | | | 45 | | | |

| Glu | His | Gln | Glu | His | Gly | Asp | Glu | Arg | Arg | Asn | Asp | Ser | Thr | His | Glu |
|---|---|---|---|---|---|---|---|---|---|---|---|---|---|---|---|
| | 50 | | | | | 55 | | | | | 60 | | | | |

| Lys | His | Gly | His | His | Asn | Cys | Ser | Glu | Asn | His | Asn | Lys | Glu | His | His |
|---|---|---|---|---|---|---|---|---|---|---|---|---|---|---|---|
| 65 | | | | | 70 | | | | | 75 | | | | | 80 |

| Asp | Glu | Asp | Asn | His | Gln | Leu | Lys | Lys | Met | His | Tyr | Tyr | Cys | Lys | Cys |
|---|---|---|---|---|---|---|---|---|---|---|---|---|---|---|---|
| | | | | 85 | | | | | 90 | | | | | 95 | |

| Arg | Gly | Gly | His | Glu | Asn | Asp | Thr | Glu | Ser | His | Glu | Gln | Glu | Glu | His |
|---|---|---|---|---|---|---|---|---|---|---|---|---|---|---|---|
| | | | 100 | | | | | 105 | | | | | 110 | | |

Glu His Ser His Gly Asn Glu Thr Glu Ile His Gly Asp Asn Tyr His
    115                 120                 125

His His His Lys Asp Ile His Lys His Leu Ser Asn His Ser Asp Thr
130                 135                 140

Ser Glu Arg Asp Gly Asp Glu Cys Arg Cys His Cys His Cys Pro Arg
145                 150                 155                 160

His Lys Gly Arg Gln Asp Lys Gln Glu Arg Lys Glu Gln Lys Lys
                165                 170                 175

Lys Gly Ser Gly Lys His Cys His Cys Phe Cys His Glu His Gly Asp
                180                 185                 190

Glu Glu Glu Lys Gly Pro Gly Gln Lys Glu Arg Asn His Glu Gly Tyr
            195                 200                 205

His Asp Lys Glu Asp Arg Gln Glu His Lys Lys Glu Ser Asp Glu Lys
        210                 215                 220

Glu His Asp Glu Glu Lys Asn Gln Asp Gln Ile Thr Lys Leu Leu Phe
225                 230                 235                 240

<210> SEQ ID NO 6
<211> LENGTH: 237
<212> TYPE: PRT
<213> ORGANISM: Acanthocheilonema viteae

<400> SEQUENCE: 6

Met Thr Thr Arg Arg Leu Gln Met Met Phe Phe Val Ala Val Val Leu
1               5                   10                  15

Ile Cys Leu Ala Leu Asn Asp Ile Gln Ala Met Arg Ile Lys Arg Asp
            20                  25                  30

Asp Ala Gly Gln Glu Asp His Arg Asn Glu Thr Asp Val Asn His Asp
        35                  40                  45

Lys His Gln Glu His Gly His Glu His Gln Asn Asp Ser Asn His Glu
    50                  55                  60

His His Asn Cys Ser Gly Ser His Glu Ser His Ser Lys Glu His His
65                  70                  75                  80

Asp Glu Asp His His His Glu Lys Lys Ile His Tyr Tyr Cys Lys Cys
                85                  90                  95

His Ser His His Asp Asn Asp Thr Glu Ser His Glu His Glu His Glu
            100                 105                 110

His Thr His Lys Asn Asp Thr Glu Ile His Gly Asp Asn Tyr His His
        115                 120                 125

His Lys Gly Thr His Glu His Leu Gly Asn Arg Ser Asp Ser Ser Glu
    130                 135                 140

His Asn His Asp Cys Gln Cys His Cys Gln Cys Pro Lys His Lys Gly
145                 150                 155                 160

Ser Tyr Asp Lys Glu Gln Glu Asp Lys Glu His Lys Lys Lys Gly Ser
                165                 170                 175

Gly Glu His Cys His Cys Phe Cys His His Gly Asp Glu Glu Gln
            180                 185                 190

Met Glu Ser Asp Gln Lys Glu Gln His Asp Lys Asp Gln His Val Asn
        195                 200                 205

Glu Asp Ser Lys Glu His Lys Ile Lys Phe Gln Ala Lys Leu Glu Ile
    210                 215                 220

Ile Val Thr Asn Leu Pro Met Thr Leu Phe Cys Phe Ser
225                 230                 235

<210> SEQ ID NO 7

<211> LENGTH: 209
<212> TYPE: PRT
<213> ORGANISM: Wuchereria bancrofti

<400> SEQUENCE: 7

```
Met Thr Thr His Arg Ser Gln Met Val Phe Ile Val Ala Val Val Leu
1               5                   10                  15

Thr Cys Leu Ala Leu His His Ile Gln Ala Met Arg Ile Lys Arg Asp
            20                  25                  30

His Ser Glu Gln Glu Asn Arg Lys Asn Glu Thr Asp Ile Asn His Gly
        35                  40                  45

Glu His Gln Glu His Gly His Glu His Gln Asn Asp Ser Ser His Glu
    50                  55                  60

Lys His Glu His His Asn Cys Ser Gly Ser His Glu Ser His Ser Lys
65                  70                  75                  80

Glu His Ser Asp Glu Asp Leu His Glu Lys Lys Thr His Tyr Tyr Cys
                85                  90                  95

Lys Cys Arg Gly His His Asp Asn Asp Ser Glu Ser His Glu His Asp
            100                 105                 110

Glu His Glu Arg Val Gly Glu Asn Asp Thr Glu Thr His Val His Lys
        115                 120                 125

Gly Ile His Glu His Val Gly Asn Asn Ser Asp Ser Ser Glu His Asn
    130                 135                 140

His Gln Asp Cys Arg Cys His Cys His Cys Pro Lys His Lys Glu Ser
145                 150                 155                 160

Asn Asn Gln Glu Gln Lys Arg Arg Gly His Arg Lys Gly Ser Arg Glu
                165                 170                 175

His Cys His Cys Phe Cys His His Arg Asp Glu Gln His Lys Gly
            180                 185                 190

Ser Asp Gln Thr Glu Arg His Asp Lys Glu His Ser Glu Glu His Lys
        195                 200                 205

Ser
```

<210> SEQ ID NO 8
<211> LENGTH: 230
<212> TYPE: PRT
<213> ORGANISM: Unknown
<220> FEATURE:
<223> OTHER INFORMATION: Brugia malayi (isoform b)

<400> SEQUENCE: 8

```
Met Thr Thr His Arg Ser Gln Met Val Tyr Ile Val Ala Val Val Leu
1               5                   10                  15

Thr Cys Leu Ala Leu Asn Asp Ile Gln Ala Met Arg Ile Lys Arg Asp
            20                  25                  30

His Ser Glu Gln Glu Asn Arg Lys Asn Glu Thr Asp Ile Asn Gln Gly
        35                  40                  45

Lys His Gln Glu His Gly Tyr Glu His Gln Asn Asp Ser Gly His Glu
    50                  55                  60

Lys His Glu His His Asn Cys Ser Glu Asn His Glu Ser His Ser Lys
65                  70                  75                  80

Glu His Ser Asp Glu Asp His Glu Lys Lys Thr His Tyr Tyr Cys
                85                  90                  95

Lys Cys Arg Asp His His Asp Asn Asp Ser Glu Ser His Glu His Asp
            100                 105                 110

Glu His Asp Arg Ala Gly Glu Asn Asp Thr Glu Thr His Val His Lys
```

```
                115                 120                 125
Gly Ile His Glu His Val Gly Asn Asn Ser Asp Ser Ser Glu Tyr Asn
    130                 135                 140

His Gln Asp Cys Arg Cys His Cys His Cys Pro Lys His Lys Gly Asn
145                 150                 155                 160

Asn Asn Gln Glu Gln Lys Arg Arg Gly His Lys Lys Gly Ser Gly Glu
                165                 170                 175

His Cys His Cys Phe Cys His His Gly Asp Glu Glu His Lys Gly
            180                 185                 190

Ser Asp Gln Thr Glu Arg His Asp Lys Glu His Ser Glu Glu His Lys
                195                 200                 205

Lys Glu Pro Glu Glu Lys Glu His Lys Glu Asp Lys Asp Gln Asp Gln
    210                 215                 220

Val Met Lys Leu Leu Phe
225                 230

<210> SEQ ID NO 9
<211> LENGTH: 234
<212> TYPE: PRT
<213> ORGANISM: Unknown
<220> FEATURE:
<223> OTHER INFORMATION: Brugia malayi (isoform c)

<400> SEQUENCE: 9

Met Thr Thr His Arg Ser Gln Met Val Tyr Ile Val Ala Val Val Leu
1               5                   10                  15

Thr Cys Leu Ala Leu Asn Asp Ile Gln Ala Met Arg Ile Lys Arg Asp
            20                  25                  30

His Ser Glu Gln Glu Asn Arg Lys Asn Glu Thr Asp Ile Asn Gln Gly
        35                  40                  45

Lys His Gln Glu His Gly Tyr Glu His Gln Asn Asp Ser Gly His Glu
    50                  55                  60

Lys His Glu His His Asn Cys Ser Glu Asn His Glu Ser His Ser Lys
65                  70                  75                  80

Glu His Ser Asp Glu Asp His His Glu Lys Lys Thr His Tyr Tyr Cys
                85                  90                  95

Lys Cys Arg Asp His His Asp Asn Asp Ser Glu Ser His Glu His Asp
            100                 105                 110

Glu His Asp Arg Ala Gly Glu Asn Asp Thr Glu Thr His Val His Lys
        115                 120                 125

Gly Ile His Glu His Val Gly Asn Asn Ser Asp Ser Ser Glu Tyr Asn
    130                 135                 140

His Gln Asp Cys Arg Cys His Cys His Cys Pro Lys His Lys Gly Asn
145                 150                 155                 160

Asn Asn Gln Glu Gln Lys Arg Arg Gly His Lys Lys Gly Ser Gly Glu
                165                 170                 175

His Cys His Cys Phe Cys His His Gly Asp Glu Glu His Lys Gly
            180                 185                 190

Ser Asp Gln Thr Glu Arg His Asp Lys Glu His Ser Glu Glu His Lys
                195                 200                 205

Arg Gly Gln Arg Ser Arg Ser Gly His Glu Thr Thr Val Leu Lys Phe
    210                 215                 220

Gln Ile Leu Cys Ser Met Ile Leu Ala Asn
225                 230
```

-continued

```
<210> SEQ ID NO 10
<211> LENGTH: 206
<212> TYPE: PRT
<213> ORGANISM: Loa loa

<400> SEQUENCE: 10
```

Met Thr Thr Gln Arg Leu Gln Met Val Phe Ile Leu Ala Val Val Leu
1               5                   10                  15

Thr Cys Leu Ala Leu Asn Asp Ile Arg Ala Met Arg Ile Lys Arg Asp
            20                  25                  30

Asp Pro Gly Gln Glu Asp His Lys Asn Gln Thr Asp Val Asn His Asp
        35                  40                  45

Glu Pro Gln Glu His Gly His Glu His Gln Asn Asp Ser Ser His Glu
    50                  55                  60

Lys His Gly His His Asn Phe Ser Gly Ser His Glu Ser Tyr Ser Lys
65                  70                  75                  80

Asp His Ser Asp Glu Asn His His Glu Lys Lys Thr Gln Tyr Tyr
                85                  90                  95

Cys Lys Cys His Ser His His Asp Asn Glu Thr Glu Ser Gln Glu His
            100                 105                 110

Glu His Glu His Lys His Ala His Glu Asn Asp Thr Glu Thr His Ser
        115                 120                 125

His Lys Asn Thr His Glu His Leu Gly Asn Tyr Ser Asp Ser Ser Glu
    130                 135                 140

His Ser Asp Gln Glu Cys Arg Cys His Cys His Cys Ser Lys His Lys
145                 150                 155                 160

Gly Ser His Ala His Lys Gln Lys Gly Ser Gly Glu His Cys His Cys
                165                 170                 175

Phe Cys His His His Gly Asp Glu Lys His Lys Gly Ser Asp Gln Met
            180                 185                 190

Glu Gln Gln Asp Lys Glu Asp His Asp Lys Glu His Lys Ser
        195                 200                 205

```
<210> SEQ ID NO 11
<211> LENGTH: 235
<212> TYPE: PRT
<213> ORGANISM: Dirofilaria immitis

<400> SEQUENCE: 11
```

Met Thr Thr Gln Arg Leu Gln Ile Val Phe Ile Val Ala Val Val Leu
1               5                   10                  15

Thr Cys Phe Ala Met Asn Asn Ile Lys Ala Met Arg Ile Lys Arg Asn
            20                  25                  30

Asp Ser Gly Gln Glu Asp His Arg Asn Gln Thr Glu Val Ser His Asp
        35                  40                  45

Glu His His Glu His Asp His Glu Tyr His Asn Asp Ser Ser His Glu
    50                  55                  60

Lys Arg Glu His His Asn Cys Ser Gly Ser Asn Glu Ser His Ser Lys
65                  70                  75                  80

Glu Tyr His Asp Glu Asp Asn His His Glu Lys Lys Met His Tyr Tyr
                85                  90                  95

Cys Lys Cys His Arg His His Asp Asn Asn Thr Asp Asn His Asp Tyr
            100                 105                 110

Glu His Ala His Glu Asn Asp Thr Glu Thr His Gly His Asn Gly His
        115                 120                 125

His Thr Gly Asn His Ser Asp Ser Val Glu Tyr Asn His Glu Glu Cys

```
                130                 135                 140
Arg Cys His Cys His Cys Pro Lys His Lys Gly Thr Tyr Asp Gln Lys
145                 150                 155                 160

Gln Glu His Lys Glu Arg Lys Asn Glu Lys His Lys Gly Ser Gly Glu
                165                 170                 175

His Cys His Cys Phe Cys His His Gly Asn Asp Glu His Lys Glu
                180                 185                 190

Ser Asn Gln Lys Glu Tyr His Asp Lys Glu Gln Asp Lys Glu His
                195                 200                 205

Asp Asn Asp Tyr Lys Lys Glu Ser Glu Glu Lys Glu Gln Lys Glu Glu
                210                 215                 220

Lys His Gln Asp Leu Val Met Lys Leu Leu Phe
225                 230                 235

<210> SEQ ID NO 12
<211> LENGTH: 233
<212> TYPE: PRT
<213> ORGANISM: Onchocerca ochengi

<400> SEQUENCE: 12

Met Thr Thr Gln Arg Leu Arg Met Met Phe Val Val Ala Val Ile Leu
1               5                   10                  15

Ser Cys Leu Ala Leu Asn Glu Ile Gln Ala Met Arg Ile Lys Arg Ser
                20                  25                  30

Asp Ala Gly Gln Glu Glu His Lys Asn Gln Thr Asp Val Asn His Asp
            35                  40                  45

Glu His Asp Glu His Ser Glu His Gln Asn Asp Ser Ser His Glu
        50                  55                  60

Lys His Glu His His Asn Cys Ser Glu Ser His Glu Ser His Ser Lys
65                  70                  75                  80

Glu His His Asp Asp Asp His Gln His Gly Lys Lys Met His Phe His
                85                  90                  95

Cys Lys Cys Arg His His Asp Asn Asp Thr Asp Ser His Glu His
                100                 105                 110

Glu His Glu His Ala Pro Glu Asn Gly Thr Glu Thr His Gly Asp Tyr
            115                 120                 125

His Glu His Lys Asp Ile His Glu His Leu Gly Asn His Ser Glu Tyr
130                 135                 140

Asn Ser Glu Glu Cys Arg Cys His Cys His Cys Pro Lys His Lys Gly
145                 150                 155                 160

Ser His Asn His Asp Gln Glu His Met Lys His Arg Lys Asn Asp Arg
                165                 170                 175

Lys Val Ser Gly Glu His Cys His Cys Phe Cys His Gln His Asp Asp
                180                 185                 190

Asp Asp Glu His Thr Gly Ser Lys Gln Lys Glu His His Asp Lys Lys
            195                 200                 205

His Gly Asp Ile Lys Lys Glu Ser Glu Glu Lys Glu Leu Lys Glu Glu
            210                 215                 220

Lys Val Ile Phe Leu Leu Asn Asn Phe
225                 230

<210> SEQ ID NO 13
<211> LENGTH: 203
<212> TYPE: PRT
<213> ORGANISM: Onchocerca gutturosa
```

```
<400> SEQUENCE: 13

Met Thr Thr Gln Arg Leu Arg Met Met Phe Val Val Ala Val Ile Leu
1               5                   10                  15

Ser Cys Leu Ala Leu Asn Glu Ile Gln Ala Met Arg Ile Lys Arg Ser
                20                  25                  30

Asp Ala Gly Gln Glu Glu His Lys Asn Gln Thr Asp Val Asn His Asp
            35                  40                  45

Glu His Asp Glu His Ser His Glu His Gln Asn Asp Ser Ser His Glu
        50                  55                  60

Lys His Glu Tyr His Asn Cys Ser Gly Ser His Glu Ser His Ser Lys
65                  70                  75                  80

Glu His His Asp Asp Asp His Gln His Gly Lys Lys Met His Phe His
                85                  90                  95

Cys Lys Cys Arg His His His Asp Asn Asp Thr Asp Ser His Glu Tyr
                100                 105                 110

Glu His Glu His Ala Pro Glu Asn Gly Thr Glu Thr His Gly Asp Tyr
            115                 120                 125

His Glu His Glu Asp Ile His Glu His Leu Gly Asn His Ser Glu Tyr
    130                 135                 140

Asn Tyr Glu Glu Cys Arg Cys His Cys His Cys Pro Lys His Lys Gly
145                 150                 155                 160

Ser His Asp His Asp Gln Glu His Val Lys His Arg Lys Asn Tyr His
                165                 170                 175

Lys Met Ser Gly Glu His Cys His Cys Phe Cys His Gln His Asp Asp
                180                 185                 190

Asp Asp Glu His Thr Gly Ser Lys Gln Lys Glu
            195                 200

<210> SEQ ID NO 14
<211> LENGTH: 236
<212> TYPE: PRT
<213> ORGANISM: Onchocerca volvulus

<400> SEQUENCE: 14

Met Thr

-continued

```
Ser His Asn His Asp Gln Glu His Met Lys His Arg Lys Asn Asp Arg
            165                 170                 175

Lys Val Ser Gly Glu His Cys His Cys Phe Cys His Gln His Asp Asp
            180                 185                 190

Asp Asp Glu His Thr Gly Ser Lys Gln Lys Glu His His Asp Lys Lys
        195                 200                 205

His Gly Asp Ile Lys Lys Glu Ser Glu Glu Lys Glu Leu Lys Glu Glu
    210                 215                 220

Lys Gln Ala Thr Thr Leu Leu Arg Asn Val Gln Leu
225                 230                 235
```